US012761149B2

(12) United States Patent
Zheng et al.

(10) Patent No.: US 12,761,149 B2
(45) Date of Patent: Oct. 13, 2026

(54) DEVICES, SYSTEMS, AND METHODS FOR CHIRAL SENSING

(71) Applicant: BOARD OF REGENTS, THE UNIVERSITY OF TEXAS SYSTEM, Austin, TX (US)

(72) Inventors: Yuebing Zheng, Austin, TX (US); Kumar Sharma, San Antonio, TX (US); Yaoran Liu, Austin, TX (US); Zilong Wu, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 946 days.

(21) Appl. No.: 18/015,768

(22) PCT Filed: Jul. 12, 2021

(86) PCT No.: PCT/US2021/041219
§ 371 (c)(1),
(2) Date: Jan. 12, 2023

(87) PCT Pub. No.: WO2022/015621
PCT Pub. Date: Jan. 20, 2022

(65) Prior Publication Data

US 2026/0251568 A1 Aug. 27, 2026

Related U.S. Application Data

(60) Provisional application No. 63/051,120, filed on Jul. 13, 2020.

(51) Int. Cl.
*G01N 21/552* (2014.01)
*G01N 21/17* (2006.01)
(Continued)

(52) U.S. Cl.
CPC .......... *G01N 21/554* (2013.01); *G01N 21/17* (2013.01); *G01N 21/19* (2013.01); *G01N 21/21* (2013.01);
(Continued)

(58) Field of Classification Search
CPC ...... G01N 21/554; G01N 21/17; G01N 21/19; G01N 21/21; G01N 33/48; G01N 33/6893; G01N 2021/216
See application file for complete search history.

(56) References Cited

U.S. PATENT DOCUMENTS 7,123,359 B2 * 10/2006 Armstrong ............. B82Y 10/00
7,709,810 B2 5/2010 Misawa et al.
(Continued)

FOREIGN PATENT DOCUMENTS

KR 20140033596 3/2014
WO 2016064859 4/2016
(Continued)

OTHER PUBLICATIONS

Extended European Search Report received in corresponding EP Application No. 21841317.7 dated Jul. 15, 2024.
(Continued)

*Primary Examiner* — Tarifur R Chowdhury
*Assistant Examiner* — Carlos Perez-Guzman
(74) *Attorney, Agent, or Firm* — Meunier Carlin & Curfman LLC

(57) ABSTRACT

Disclosed herein is a device for chiral sensing comprising a chiral plasmonic substrate, wherein when the device is assembled together with a first light source, a liquid sample comprising a plurality of chiral analytes, a second light source, and an instrument, the first light source is configured to illuminate the chiral plasmonic substrate with electromagnetic radiation; and the second light source is configured
(Continued)

to illuminate the chiral plasmonic substrate with circularly polarized electromagnetic radiation. The instrument is configured to process electromagnetic signal from the first light source and the second light source to determine a property of the liquid sample.

21 Claims, 47 Drawing Sheets

(51) Int. Cl.

| | |
|---|---|
| ***G01N 21/19*** | (2006.01) |
| ***G01N 21/21*** | (2006.01) |
| ***G01N 33/48*** | (2006.01) |
| ***G01N 33/68*** | (2006.01) |

(52) U.S. Cl.
CPC ......... *G01N 33/48* (2013.01); *G01N 33/6893* (2013.01); *G01N 2021/216* (2013.01)

(56) References Cited

U.S. PATENT DOCUMENTS

| | | | |
|---|---|---|---|
| 8,734,679 | B2 | 5/2014 | Marguerettaz et al. |
| 8,765,231 | B2 | 7/2014 | Vuong et al. |
| 10,540,571 | B2 | 1/2020 | Hoover et al. |
| 10,736,551 | B2 | 8/2020 | Rogers |
| 2006/0034729 | A1 | 2/2006 | Poponin |
| 2009/0032735 | A1 | 2/2009 | Misawa et al. |
| 2010/0133488 | A1 | 6/2010 | Giakos |
| 2010/0232017 | A1 | 9/2010 | McCarthy et al. |
| 2011/0269364 | A1 | 11/2011 | Yoon |
| 2012/0262500 | A1 | 10/2012 | Kitazawa et al. |
| 2013/0100454 | A1 | 4/2013 | Walters |
| 2013/0252016 | A1 | 9/2013 | Glembocki et al. |
| 2015/0017433 | A1 | 1/2015 | Alisafaee et al. |
| 2015/0070693 | A1 | 3/2015 | Sugimoto et al. |
| 2016/0118249 | A1 | 4/2016 | Sreenivasan et al. |
| 2016/0236373 | A1 | 8/2016 | Sonoda et al. |
| 2017/0315102 | A1 | 11/2017 | Sun et al. |
| 2017/0356843 | A1 | 12/2017 | Alu et al. |
| 2018/0236486 | A1 | 8/2018 | Zheng et al. |
| 2018/0348128 | A1 | 12/2018 | Zheng et al. |
| 2019/0113453 | A1 | 4/2019 | Zheng et al. |
| 2019/0195805 | A1 | 6/2019 | Zheng et al. |
| 2019/0264327 | A1 | 8/2019 | Zheng et al. |
| 2020/0264101 | A1 | 8/2020 | Zheng et al. |
| 2021/0311397 | A1 | 10/2021 | Zheng et al. |

FOREIGN PATENT DOCUMENTS

| | | |
|---|---|---|
| WO | 2017106145 | 6/2017 |
| WO | 2019060280 | 3/2019 |

OTHER PUBLICATIONS

Liu et al., "Microbubble-Assisted Preconcentration and Ultrasensitive Detection of Biomolecules using Plasmonic Chiral Metamaterials", 2020 Conference On Lasers and Electrooptics (CLEO), OSA, May 10, 2020, pp. 1-2, XP033823007.
Baffou et al., "Super-Heating and Micro-Bubble Generation around Plasmonic Nanoparticles under cw Illumination", The Journal of Physical Chemistry C, vol. 118, No. 9, Jan. 21, 2014, pp. 4890-4898, XP055545471.
International Preliminary Report on Patentability issued for Application No. PCT/US2021/041219 dated Jan. 26, 2023.
Ariens, "Stereochemistry, a basis for sophisticated nonsense in pharmacokinetics and clinical-pharmacology", European Journal of Clinical Pharmacology 26, 663-668, (1984).
Barik A et al. Dielectrophoresis-enhanced plasmonic sensing with gold nanohole arrays. Nano letters 2014, 14 (4), 2006-2012.
Belushkin A et al. Nanoparticle-Enhanced Plasmonic Biosensor for Digital Biomarker Detection in a Microarray. ACS nano 2018, 12 (5), 4453-4461.
Ben-Moshe A et al. Chirality and chiroptical effects in inorganic nanocrystal systems with plasmon and exciton resonances. Chemical Society Reviews 42, 7028-7041 (2013).
Cahn RS et al. Specification of molecular chirality. Angewandte Chemie International Edition in English 5, 385-415 (1966).
Chen YH et al. Determination of the secondary structures of proteins by circular dichroism and optical rotatory dispersion. Biochemistry 1972, 11 (22), 4120-4131.
Decker, et al., "Strong optical activity from twisted-cross photonic metamaterials", Optics Letters 34, 2501-2503, (2009).
Droulias, et al., "Broad-band giant circular dichroism in metamaterials of twisted chains of metallic nanoparticles", Journal of Physical Chemistry C 117, 1130-1135, (2013).
Erb, "Single enantiomer drugs poised for further market growth", Pharmaceutical Technology 30, s14-s18, (2006).
Eriksson, et al., "Clinical pharmacology of thalidomide", European Journal of Clinical Pharmacology 57, 365-376, (2001).
García-Guirado J et al. Enantiomer-selective molecular sensing using racemic nanoplasmonic arrays. Nano letters 18, 6279-6285 (2018).
Garcia-Guirado J. et al. Overcoming diffusion-limited biosensing by electrothermoplasmonics. ACS Photonics 5, 3673-3679 (2018).
Govorov, et al., "Plasmon-induced circular dichroism of a chiral molecule in the vicinity of metal nanocrystals", Application to various geometries. Journal of Physical Chemistry C 115, 7914-7923, (2011).
Govorov, et al., "Theory of circular dichroism of nanomaterials comprising chiral molecules and nanocrystals: plasmon enhancement, dipole interactions, and dielectric effects", Nano Letters 10, 1374-1382, (2010).
Greenfield NJ et al. Computed circular dichroism spectra for the evaluation of protein conformation. Biochemistry 1969, 8 (10), 4108-4116.
Guerrero-Martinez, "Intense optical activity from three-dimensional chiral ordering of plasmonic nanoantennas", Angewandte Chemie-International Edition 50, 5499-5503, (2011).
Hamase K et al. D-Amino acids in mammals and their diagnostic value. Journal of chromatography B 781, 73-91 (2002).
Hendry E et al. Ultrasensitive detection and characterization of biomolecules using superchiral fields. Nature nanotechnology 5, 783 (2010).
Hentschel M et al. Chiral plasmonics. Science advances 3, e1602735 (2017).
Hoffman WS et al. A rapid photoelectric method for the determination of glucose in blood and urine. Journal of Biological Chemistry 1937, 120 (1), 51-55.
Hu et al. High Quality Factor Dielectric Metasurfaces for Ultraviolet Circular Dichroism Spectroscopy, ACS Photonics 2020, 7(1), 36-42.
Huang, "Broadband circular polarizer using stacked chiral polymer films", Optics Express 15, 6414-6419, (2007).
Hutt, et al., "Drug chirality and its clinical significance", Drugs 52, 1-12, (1996).
Kang Z et al. Surface-enhanced Raman scattering via entrapment of colloidal plasmonic nanocrystals by laser generated microbubbles on random gold nano-islands. Nanoscale 2016, 8 (19), 10266-10272.
Kelly C et al. Controlling metamaterial transparency with superchiral fields. ACS Photonics 5, 535-543 (2018).
Kelly, "How to study proteins by circular dichroism", Biochimica Et Biophysica Acta-Proteins and Proteomics, 2005, 1751, 119-139.
Lee S et al. Microscopic origin of surface-enhanced circular dichroism. ACS Photonics 4, 2047-2052 (2017).
Lin L et al. Bubble-pen lithography. Nano letters 2015, 16 (1), 701-708.
Lorenzo MP et al. Optimization and validation of a chiral GC-MS method for the determination of free d-amino acids ratio in human urine: application to a gestational diabetes mellitus study. Journal of pharmaceutical and biomedical analysis 107, 480-487 (2015).

(56) References Cited

OTHER PUBLICATIONS

Lussier F et al. Dynamic-SERS optophysiology: a nanosensor for monitoring cell secretion events. Nano letters 2016, 16 (6), 3866-3871.
Mcanally MO et al. Quantitative determination of the differential raman scattering cross sections of glucose by femtosecond stimulated raman scattering. Analytical chemistry 2017, 89 (13), 6931-6935.
Meierhenrich UJ et al. Circular dichroism of amino acids in the vacuum-ultraviolet region. Angewandte Chemie International Edition 2010, 49 (42), 7799-7802.
Meinzer, et al., "Probing the chiral nature of electromagnetic fields surrounding plasmonic nanostructures", Physical Review B, 2013, 88, 041407.
Micsonai A et al. Accurate secondary structure prediction and fold recognition for circular dichroism spectroscopy. Proceedings of the National Academy of Sciences 112, E3095-E3103 (2015).
Min JZ et al. Determination of dl-amino acids, derivatized with R (-)-4-(3-isothiocyanatopyrrolidin-1-yl)-7-(N, N-dimethylaminosulfonyl)-2, 1, 3-benzoxadiazole, in nail of diabetic patients by UPLC-ESI-TOF-MS. Journal of Chromatography B 879, 3220-3228 (2011).
Moffitt W. Optical Rotatory Dispersion of Helical Polymers. J Chem Phys 1956, 25 (3), 467-478.
Morasch M et al. Heated gas bubbles enrich, crystallize, dry, phosphorylate and encapsulate prebiotic molecules. Nature chemistry 11, 779-788 (2019).
Ndukaife JC et al. Long-range and rapid transport of individual nano-objects by a hybrid electrothermoplasmonic nanotweezer. Nature nanotechnology 2016, 11 (1), 53.
Ohzono, "A liquid crystalline chirality balance for vapours", Nat Commun. 2014, 5, 3735.
Okamoto Y et al. Chiral HPLC for efficient resolution of enantiomers. Chemical Society Reviews 37, 2593-2608 (2008).
Pang et al. Optical Trapping of Individual Human Immunodeficiency Viruses in Culture Fluid Reveals Heterogeneity with Single-Molecule Resolution, Nat Nanotechol. 2014, 9(8), 624-630.
Patterson, et al., "Enantiomer-specific detection of chiral molecules via microwave spectroscopy", Nature, 2013, 497, 475-477.
Pirnstill CW et al. In vivo glucose monitoring using dual-wavelength polarimetry to overcome corneal birefringence in the presence of motion. Diabetes technology & therapeutics 14, 819-827 (2012).
Plum, et al., "Giant optical gyrotropy due to electromagnetic coupling", Applied Physics Letters, 2007, 90, 223113.
Purvinis G et al. Noninvasive polarimetric-based glucose monitoring: an in vivo study. Journal of diabetes science and technology 5, 380-387 (2011).
Rajeeva et al. Accumulation-Driven Unified Spatiotemporal Synthesis and Structuring of Immiscible Metallic Nanoalloys, Matter 2019, 1(6), 1606-1617.
Richardson, "Handedness of crossover connections in beta-sheets", Proceedings of the National Academy of Sciences of the United States of America, 1976, 73, 2619-2623.
Rogacheva, et al., "Giant gyrotropy due to electromagnetic-field coupling in a bilayered structure", Physical Review Letters, 2006, 97, 177401.
Roxworthy BJ et al. Understanding and controlling plasmon-induced convection. Nature communications 2014, 5, 3173.
Sasabe J et al. Distinctive roles of d-Amino acids in the homochiral world: Chirality of amino acids modulates mammalian physiology and pathology. The Keio journal of medicine (2018).
Schäferling M et al. Tailoring enhanced optical chirality: design principles for chiral plasmonic nanostructures. Physical Review X 2, 031010 (2012).
Schreiber, et al., "Chiral plasmonic DNA nanostructures with switchable circular dichroism", Nature Communications, 2013, 4, 2498.
Shah NC et al. Lactate and sequential lactate—glucose sensing using surface-enhanced Raman spectroscopy. Analytical chemistry 2007, 79 (18), 6927-6932.
Shalaev, "Optical negative-index metamaterials", Nature Photonics, 2007, 1, 41-48.
Soltani, et al., "Nanophotonic trapping for precise manipulation of biomolecular arrays", Nature Nanotech., 2014, 9, 448-452.
Talasniemi JP et al. Analytical investigation: assay of D-lactate in diabetic plasma and urine. Clinical biochemistry 41, 1099-1103 (2008).
Tang Y et al. Enhanced enantioselectivity in excitation of chiral molecules by superchiral light. Science 332, 333-336 (2011).
Tang, et al., "Optical chirality and its interaction with matter", Physical Review Letters, 2010, 104, 163901.
Tantussi F et al. Long-Range Capture and Delivery of Water-Dispersed Nano-objects by Microbubbles Generated on 3D Plasmonic Surfaces. ACS nano 2018, 12 (5), 4116-4122.
Teo, et al., "Clinical pharmacokinetics of thalidomide", Clinical Phamacokinetics, 2004, 43, 311-327.
Tokel et al. Advances in Plasmonic Technologies for Point of Care Applications, Chemical Reviews, 2014, 114, 5728-5752.
Tullius R et al. "Superchiral" Spectroscopy: Detection of Protein Higher Order Hierarchical Structure with Chiral Plasmonic Nanostructures. J. Am. Chem. Soc. 137, 8380-8383 (2015).
Valev VK et al. Chirality and chiroptical effects in plasmonic nanostructures: fundamentals, recent progress, and outlook. Advanced Materials 25, 2517-2534 (2013).
Wienken CJ et al. Protein-binding assays in biological liquids using microscale thermophoresis. Nature communications 1, 100 (2010).
Wu Z et al. Chiral metamaterials via Moiré stacking. Nanoscale 10, 18096-18112 (2018).
Wu Z et al. Moiré metamaterials and metasurfaces. Advanced Optical Materials 6, 1701057 (2018).
Wu Z et al. Room-Temperature Active Modulation of Valley Dynamics in a Monolayer Semiconductor through Chiral Purcell Effects. Advanced Materials 31, 1904132 (2019).
Wu Z et al. Y. Moiré chiral metamaterials. Advanced Optical Materials 5, 1700034 (2017).
Yang JT et al. The optical rotatory dispersion of polypeptides and proteins in relation to configuration1. Journal of the American Chemical Society 1957, 79 (4), 761-775.
Yu Q et al. Inverted size-dependence of surface-enhanced Raman scattering on gold nanohole and nanodisk arrays. Nano letters 2008, 8 (7), 1923-1928.
Zhang et al. Unraveling the origin of chirality from plasmonic nanoparticle-protein complexes, Science, 2019, 365(6460), 1475-1478.
Zhao et al. Theory and experiment on particle trapping and manipulation via optothermally generated bubbles, Lab on a Chip, 2014, 14, 384.
Zhao, et al., "Chirality detection of enantiomers using twisted optical metamaterials", Nature Communications, 2017, 8, 14180.
Zhao, et al., "Homogenization of plasmonic metasurfaces modeled as transmission-line loads", Metamaterials, 2011, 5, 90-96.
Zhao, et al., "Tailoring the Dispersion of Plasmonic Nanorods to Realize Broadband Optical Meta-Waveplates", Nano Letters 2013 13 (3), 1086-1091 DOI: 10.1021/nl304392b.
International Search Report and Written Opinion received in PCT/US2021/041219, mailed Oct. 26, 2021, 17 pages.

* cited by examiner

DEVICES, SYSTEMS, AND METHODS FOR CHIRAL SENSING

CROSS-REFERENCE TO RELATED APPLICATIONS

This application is a U.S. National Stage application filed under 35 U.S.C. § 371 of PCT/US2021/041219 filed Jul. 12, 2021, which claims the benefit of priority to U.S. Provisional Application No. 63/051,120 filed Jul. 13, 2020, each of which is hereby incorporated herein by reference in its entirety.

STATEMENT OF GOVERNMENT SUPPORT

This invention was made with government support under Grant No. GM128446 awarded by the National Institutes of Health, Grant No. CMMI1761743 awarded by the National Science Foundation, and Grant No. 80NSSC17K0520 awarded by the National Aeronautics and Space Administration. The government has certain rights in the invention.

BACKGROUND

As building blocks of life, chiral molecules in human bodies are usually dominated by one of the enantiomers, showing homochirality that is essential for proper biochemical processes. Abnormal concentration of chiral molecules has been observed in human bodies with increasing age and various chronic diseases, indicating the potential of applying chiral biomarkers as health indicators for diagnostic and prognostic applications. Therefore, it is can be important to monitor both chemical composition and chirality of biomarkers for clinical purposes. However, current methods to achieve such clinical detection are either time-consuming or require large amounts of body fluids. The complexity and high cost of existing devices also hinder point-of-care clinical monitoring. Further, it is challenging to achieve preconcentration for metabolites and small molecules using existing techniques due to their relatively small size and polar properties. Therefore, a need exists for devices and methods to overcome one or more of these limitations. The devices, systems, and methods discussed herein address these and other needs.

SUMMARY

In accordance with the purposes of the disclosed devices, systems, and methods as embodied and broadly described herein, the disclosed subject matter related to devices, systems, and methods for chiral sensing.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
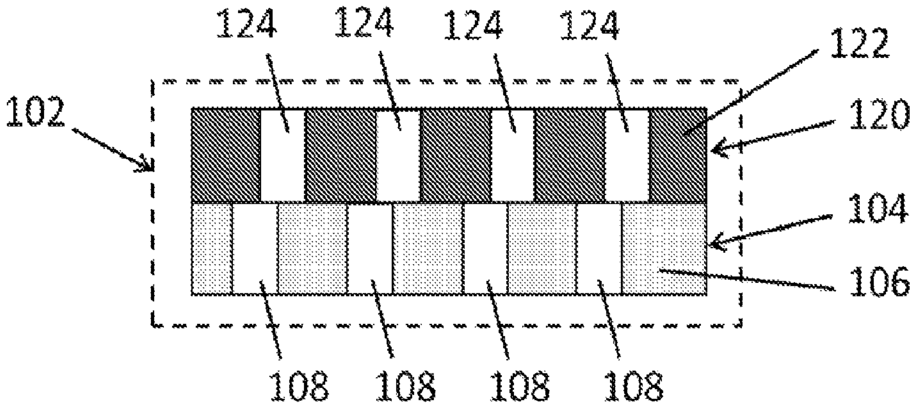
FIG. 1 is a schematic illustration of an example chiral plasmonic substrate as disclosed herein.

The devices, systems, and methods described herein may be understood more readily by reference to the following detailed description of specific aspects of the disclosed subject matter and the Examples included therein.

Before the present devices, systems, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient" refers to a subject under the treatment of a clinician, e.g., physician.

The term "inhibit" refers to a decrease in an activity, response, condition, disease, or other biological parameter. This can include but is not limited to the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms "prevent" or "suppress" can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Methods

Disclosed herein are methods comprising illuminating a first location of a chiral plasmonic substrate with electromagnetic radiation. As used herein, "a first location" and "the first location" are meant to include any number of locations in any arrangement on the chiral plasmonic substrate. Thus, for example "a first location" includes one or more first locations. In some embodiments, the first location can comprise a plurality of locations. In some embodiments, the first locations can comprise a plurality of locations arranged in an ordered array.

The electromagnetic radiation can, for example, have a power density of 0.5 mW/λm$^2$ or more (e.g., 0.6 mW/λm$^2$ or more, 0.7 mW/λm$^2$ or more, 0.8 mW/λm$^2$ or more, or 0.9 mW/λm$^2$ or more). In some examples, the electromagnetic radiation can have a power density of 1 mW/λm$^2$ or less (e.g., 0.9 mW/λm$^2$ or less, 0.8 mW/λm$^2$ or less, 0.7 mW/λm$^2$ or less, or 0.6 mW/λm$^2$ or less). The power density of the electromagnetic radiation can range from any of the minimum values described above to any of the maximum values described above. For example, the electromagnetic radiation can have a power density of from 0.5 mW/λm$^2$ to 1 mW/μm$^2$ (e.g., from 0.5 mW/λm$^2$ to 0.75 mW/μm$^2$, from 0.75 mW/λm$^2$ to 1 mW/μm$^2$, from 0.5 mW/λm$^2$ to 0.6 mW/μm$^2$, from 0.6 mW/λm$^2$ to 0.7 mW/μm$^2$, from 0.7 mW/λm$^2$ to 0.8 mW/μm$^2$, from 0.8 mW/μm$^2$ to 0.9 mW/μm$^2$, from 0.9 mW/λm$^2$ to 1 mW/μm$^2$, from 0.5 mW/λm$^2$ to 0.9 mW/μm$^2$, from 0.6 mW/λm$^2$ to 1 mW/μm$^2$, or from 0.6 mW/λm$^2$ to 0.9 mW/μm$^2$).

The electromagnetic radiation can, for example, be provided by a light source. The light source can be any type of light source. Examples of suitable light sources include natural light sources (e.g., sunlight) and artificial light sources (e.g., incandescent light bulbs, light emitting diodes, gas discharge lamps, arc lamps, lasers etc.). In some examples, the light source is a laser, such as a continuous wave laser.

In some examples, the light source is configured to illuminate a mirror and/or a beam splitter, the mirror and/or beam splitter being configured to reflect and/or redirect the electromagnetic radiation from the light source to illuminate the first location of the chiral plasmonic substrate. In some examples, the mirror can comprise a plurality of mirrors, such as an array of micromirrors (e.g., a digital micromirror device).

The electromagnetic radiation comprises a wavelength that overlaps with at least a portion of the plasmon resonance energy of the chiral plasmonic substrate such that the chiral plasmonic substrate converts at least a portion of the electromagnetic radiation into thermal energy.

As used herein, a chiral plasmonic substrate is any substrate that is both chiral and plasmonic. For example, the chiral plasmonic substrate can comprise a plurality of chiral structures comprising a plasmonic material; a film of a plasmonic material permeated by a plurality of chiral holes; a plurality of achiral plasmonic particles arranged to give a chiral superstructure; two or more films of a plasmonic material permeated by a plurality of achiral holes stacked to give a chiral superstructure; and the like. In some examples, the chiral plasmonic substrate can comprise any of those described in: Valev et al. *Advanced Materials,* 2013, 25 (18), 2517-2534; Zhao et al. *Nature Communications,* 2017, 8, 14180; US 2017/0356843; Hendry et al. *Nature Nanotechnology,* 2010, 5, 783-787; WO 2019/060280; Wu et al. *Adv. Optical Materials,* 2017, 5, 1700034; and Wu et al. *Nanoscale,* 2018, 10, 18096-18112; each of which are hereby incorporated herein for their description of chiral plasmonic substrates.

In some examples, the chiral plasmonic substrate comprises a first nanostructured layer. As used herein, "nanostructured" means any structure with one or more nanosized features. A nanosized feature can be any feature with at least one dimension less than 1 μm in size. For example, a nanosized feature can comprise a nanowire, nanotube, nanoparticle, nanopore, and the like, or combinations thereof. In some examples, the nanostructured layer can comprise a material that is not nanosized but has been modified with a nanowire, nanotube, nanoparticle, nanopore, or a combination thereof. The first nanostructured layer can comprise a first layer of a first plasmonic material permeated by a first plurality of spaced-apart holes.

Examples of plasmonic materials include, but are not limited to, plasmonic metals, plasmonic semiconductors (e.g., silicon carbide), doped semiconductors (e.g., aluminum-doped zinc oxide), transparent conducting oxides, perovskites, metal nitrides, metal oxides, silicides, germanides, two-dimensional plasmonic materials (e.g., graphene), and combinations thereof.

In some examples, the first plasmonic material can comprise a plasmonic metal. Examples of plasmonic metals include, but are not limited to Au, Ag, Pt, Pd, Cu, Cr, Al, and combinations thereof.

In some examples, the first plasmonic material can comprise a plasmonic oxide material, for example a metal oxide. In some examples, the plasmonic oxide material can comprise a transparent conducting oxide material. Examples of plasmonic oxide materials include, but are not limited to, tungsten oxide, indium oxide, molybdenum oxide, tin-doped indium oxide (e.g., indium tin oxide, ITO), fluorine-doped tin oxide (FTO), indium-doped cadmium oxide (ICO), aluminum-doped zinc oxide (AZO), antimony-doped tin oxide (ATO), cesium tungsten oxide ($Cs_xWO_3$), and combinations thereof. Plasmonic oxide materials are further described, for example by Lounis et al. in The Journal of Physical Chemistry Letters, 2014, 5, 1564-1574, which is hereby incorporated herein by reference for its discussion of plasmonic oxide materials.

In some examples, the thickness of the first layer of the first plasmonic material can be 15 nm or more (e.g., 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, or 180 nm or more). In some examples, the thickness of the first layer of the first plasmonic material can be 200 nm or less (e.g., 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 45 nm or less, 40 nm or less, 35 nm or less, 30 nm or less, or 25 nm or less). The thickness of the first layer of the first plasmonic material can range from any of the minimum values described above to any of the maximum values described above. For example, the thickness of the first layer of the first plasmonic material can be from 15 nm to 200 nm (e.g., from 15 nm to 100 nm, from 100 nm to 200 nm, from 15 nm to 50 nm, from 50 nm to 100 nm, from 100 nm to 150 nm, from 150 nm to 200 nm, or from 20 nm to 150 nm).

In some examples, the nanostructured plasmonic material can further comprise a substrate having a first surface, wherein the first nanostructured layer is disposed on the first surface. In some examples, the substrate can be transparent. As used herein, a "transparent substrate" is meant to include any substrate that is transparent at the wavelength or wavelength region of interest. Examples of substrates include, but are not limited to, glass, quartz, parylene, silicon dioxide, mica, poly(methyl methacrylate), polyamide, polycarbonate, polyester, polypropylene, polytetrafluoroethylene, polydimethylsiloxane (PDMS), hafnium oxide, hafnium silicate, tantalum pentoxide, zirconium dioxide, zirconium silicate, and combinations thereof. The substrate can, for example, comprise glass, quartz, silicon dioxide, silicon nitride, a polymer, or a combination thereof.

In some examples, the substrate can be substantially optically transparent. For example, the substrate can have an average transmittance of 75% or more at one or more wavelengths from 350 nm to 1000 nm (e.g., 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more). In some examples, the substrate can have an average transmittance of 100% or less at one or more wavelengths from 350 nm to 1000 nm (e.g., 99% or less, 98% or less, 97% or less, 96% or less, 95% or less, 94% or less, 93% or less, 92% or less, 91% or less, 90% or less, 89% or less, 88% or less, 87% or less, 86% or less, 85% or less, 84% or less, 83% or less, 82% or less, 81% or less, 80% or less, 79% or less, 78% or less, 77% or less, or 76% or less). The average transmittance of the substrate at one or more wavelengths from 350 nm to 1000 nm can range from any of the minimum values described above to any of the maximum valued described above. For example, the substrate can have an average transmittance of from 75% to 100% at one or more wavelengths from 350 nm to 1000 nm (e.g., from 75% to 87%, from 87% to 100%, from 75% to 80%, from 80% to 85%, from 85% to 90%, from 90% to 95%, from 95% to 100%, or from 80% to 95%).

Each of the holes in the first plurality of spaced-apart holes can have an average characteristic dimension. The term "characteristic dimension," as used herein, refers to the largest straight line distance spanning a hole in the plane of the layer (e.g., in the plane of the first layer that is substantially parallel to the first surface of the substrate). For example, in the case of a hole having a substantially circular shape in the plane of the layer, the characteristic dimension of the hole is the diameter of the hole. "Average characteristic dimension" and "mean characteristic dimension" are used interchangeably herein, and generally refer to the statistical mean characteristic dimension of the particles in a population of particles. The characteristic dimension can be measured using methods known in the art, such as evaluation by scanning electron microscopy, transmission electron microscopy, and/or atomic force microscopy.

For example, the first plurality of holes can have an average characteristic dimension of 20 nm or more (e.g., 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 550 nm or more, 600 nm or more, 650 nm or more, 700 nm or more, or 750 nm or more). In some examples, the first plurality of boles can have an average characteristic dimension of 800 nm or less (e.g., 750 nm or less, 700 nm or less, 650 nm or less, 600 nm or less, 550 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, or 30 nm or less). The average characteristic dimension of the first plurality of holes can range from any of the minimum values described above to any of the maximum values described above. For example, the first plurality of holes can have an average characteristic dimension of from 20 nm to 800 nm (e.g., from 20 nm to 400 nm, from 400 nm to 800 nm, from 20 nm to 200 nm, from 200 nm to 400 nm, from 400 nm to 600 nm, from 600 nm to 800 nm, or from 50 nm to 700 nm).

In some examples, the first plurality of spaced-apart holes can be substantially monodisperse. "Monodisperse" and "homogeneous size distribution," as used herein, and generally describe a population of holes where all of the holes have the same or nearly the same characteristic dimension. As used herein, a monodisperse distribution refers to hole distributions in which 80% of the distribution (e.g., 85% of the distribution, 90% of the distribution, or 95% of the distribution) lies within 25% of the mean characteristic dimension (e.g., within 20% of the mean characteristic dimension, within 15% of the mean characteristic dimension, within 10% of the mean characteristic dimension, or within 5% of the mean characteristic dimension).

The first plurality of spaced apart holes can comprise holes of any shape (e.g., a sphere, a rod, an ellipsoid, a triangular prism, a pyramid, a polygon, a cylinder, a rectangular prism, etc.). In some examples, the first plurality of spaced-apart holes can have an isotropic shape. In some examples, the first plurality of spaced-apart holes can have an anisotropic shape. In some examples, each of the holes in the first plurality of spaced-apart holes is substantially cylindrical in shape, such that the diameter of each cylinder is the average characteristic dimension of each of the holes.

The first plurality of spaced apart holes comprise a first array defined by a first unit cell. As used herein, a "unit cell" is the smallest group of holes in the array that constitutes the repeating pattern of the array. The first unit cell can have a first principle axis and a second principle axis with a first included angle between the first principle axis and the second principle axis. The first array is built up of repetitive translations of the first unit cell along its principle axes.

The first principle axis of the first unit cell has a length that is the distance separating each hole in the first array from its neighboring hole (edge to edge) along the first principle axis. In some examples, the length of the first principle axis in the first array can be 60 nm or more (e.g., 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 175 nm or more, 200 nm or more, 225 nm or more, 250 nm or more, 275 nm or more, 300 nm or more, 350 nm or more, 400 nm or more, 450 nm or more, 500 nm or more, 600 nm or more, 700 nm or more, 800 nm or more, or 900 nm or more). In some examples, the length of the first principle axis in the first array can be 1000 nm or less (e.g., 900 nm or less, 800 nm or less, 700 nm or less, 600 nm or less, 500 nm or less, 450 nm or less, 400 nm or less, 350 nm or less, 300 nm or less, 275 nm or less, 250 nm or less, 225 nm or less, 200 nm or less, 175 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, or 70 nm or less). The length of the first principle axis in the first array can range from any of the minimum values described above to any of the maximum values described above. For example, the length of the first principle axis in the first array can be from 60 nm to 1000 nm (e.g., from 60 nm to 500 nm, from 500 nm to 1000 nm, from 60 nm to 200 nm, from 200 nm to 400 nm, from 400 nm to 600 nm, from 600 nm to 800 nm, from 800 nm to 1000 nm, or from 100 nm to 900 nm).

In some examples, the first plurality of holes can have an average characteristic dimension that is 40% of the length of the first principle axis in the first array or more (e.g., 45% or more, 50% or more, 55% or more, 60% or more, 65% or more, or 70% or more). In some examples, the first plurality of holes can have an average characteristic dimension that is 80% of the length of the first principle axis in the first array or less (e.g., 75% or less, 70% or less, 65% or less, 60% or less, 55% or less, or 50% or less). The average characteristic dimension of the first plurality of holes can range from any of the minimum values described above to any of the maximum values described above. For example, the first plurality of holes can have an average characteristic dimension that is from 40% to 80% of the length of the first principle axis in the first array (e.g., from 40% to 60%, from 60% to 80%, from 40% to 50%, from 50% to 60%, from 60% to 70%, from 70% to 80%, or from 45% to 75%).

The second principle axis of the first unit cell has a length that is the distance separating each hole in the first array from its neighboring hole (edge to edge) along the second principle axis. In some examples, the length of the second principle axis in the first array can be 60 nm or more (e.g., 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 175 nm or more, 200 nm or more, 225 nm or more, 250 nm or more, 275 nm or more, 300 nm or more, 350 nm or more, 400 nm or more, 450 nm or more, 500 nm or more, 600 nm or more, 700 nm or more, 800 nm or more, or 900 nm or more). In some examples, the length of the second principle axis in the first array can be 1000 nm or less (e.g., 900 nm or less, 800 nm or less, 700 nm or less, 600 nm or less, 500 nm or less, 450 nm or less, 400 nm or less, 350 nm or less, 300 nm or less, 275 nm or less, 250 nm or less, 225 nm or less, 200 nm or less, 175 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, or 70 nm or less). The length of the second principle axis in the first array can range from any of the minimum values described above to any of the maximum values described above. For example, the length of the second principle axis in the first array can be from 60 nm to 1000 nm (e.g., from 60 nm to 500 nm, from 500 nm to 1000 nm, from 60 nm to 200 nm, from 200 nm to 400 nm, from 400 nm to 600 nm, from 600 nm to 800 nm, from 800 nm to 1000 nm, or from 100 nm to 900 nm). In some examples, the length of the first principle axis in the first array can be substantially the same as the length of the second principle axis in the first array.

In some examples, the first plurality of holes can have an average characteristic dimension that is 40% of the length of the second principle axis in the first array or more (e.g., 45% or more, 50% or more, 55% or more, 60% or more, 65% or more, or 70% or more). In some examples, the first plurality of holes can have an average characteristic dimension that is 80% of the length of the second principle axis in the first array or less (e.g., 75% or less, 70% or less, 65% or less, 60% or less, 55% or less, or 50% or less). The average characteristic dimension of the first plurality of holes can range from any of the minimum values described above to any of the maximum values described above. For example, the first plurality of holes can have an average characteristic dimension that is from 40% to 80% of the length of the second principle axis in the first array (e.g., from 40% to 60%, from 60% to 80%, from 40% to 50%, from 50% to 60%, from 60% to 70%, from 70% to 80%, or from 45% to 75%).

The first unit cell can be of any shape. In some examples, the first unit cell is in the shape of a triangle. In some examples, the first unit cell is in the shape of a quadrilateral (e.g., a rectangle, a parallelogram, or the like).

The first included angle between the first principle axis and the second principle axis of the first unit cell can, for example, be 45° or more (e.g., 50° or more, 55° or more, 60° or more, 65° or more, 70° or more, 75° or more, 80° or more, 85° or more, 90° or more, 95° or more, 100° or more, 105° or more, 110° or more, 115° or more, 120° or more, 125° or more, or 130° or more). In some examples, the first included angle between the first principle axis and the second principle axis of the first unit cell can be 135° or less (e.g., 130° or less, 125° or less, 120° or less, 115° or less, 110° or less, 105° or less, 100° or less, 95° or less, 90° or less, 85° or less, 80° or less, 75° or less, 70° or less, 65° or less, 60° or less, 55° or less, or 50° or less). The first included angle between the first principle axis and the second principle axis of the first unit cell can range from any of the minimum values described above to any of the maximum values described above. For example, the first included angle between the first principle axis and the second principle axis of the first unit cell can be from 45° to 135° (e.g., from 45° to 90°, from 90° to 135°, from 45° to 60°, from 60° to 75°, from 75° to 90°, from 90° to 105°, from 105° to 120°, from 120° to 135°, from 80° to 100°, or from 60° to) 120°. In some examples, the first included angle is 90°.

The nanostructured plasmonic materials can further comprise a second nanostructured layer. In some examples, the nanostructured layer can comprise a material that is not nanosized but has been modified with a nanowire, nanotube, nanoparticle, nanopore, or a combination thereof. The second nanostructured layer can comprise a second layer of a second plasmonic material permeated by a second plurality of spaced-apart holes.

Examples of plasmonic materials include, but are not limited to, plasmonic metals, plasmonic semiconductors (e.g., silicon carbide), doped semiconductors (e.g., aluminum-doped zinc oxide), transparent conducting oxides, perovskites, metal nitrides, silicides, germanides, two-dimensional plasmonic materials (e.g., graphene), and combinations thereof.

In some examples, the second plasmonic material can comprise a plasmonic metal. Examples of plasmonic metals include, but are not limited to Au, Ag, Pt, Pd, Cu, Cr, Al, and combinations thereof.

In some examples, the second plasmonic material can comprise a plasmonic oxide material, for example a metal oxide. In some examples, the plasmonic oxide material can comprise a transparent conducting oxide material. Examples of plasmonic oxide materials include, but are not limited to, tungsten oxide, indium oxide, molybdenum oxide, tin-doped indium oxide (e.g., indium tin oxide, ITO), fluorine-doped tin oxide (FTO), indium-doped cadmium oxide (ICO), aluminum-doped zinc oxide (AZO), antimony-doped tin oxide (ATO), cesium tungsten oxide ($CsxWO_3$), and combinations thereof. Plasmonic oxide materials are further described, for example by Lounis et al. in The Journal of Physical Chemistry Letters, 2014, 5, 1564-1574, which is hereby incorporated herein by reference for its discussion of plasmonic oxide materials.

In some examples, the thickness of the second layer of the second plasmonic material can be 15 nm or more (e.g., 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 110 nm or more, 120 nm or more, 130 nm or more, 140 nm or more, 150 nm or more, 160 nm or more, 170 nm or more, or 180 nm or more). In some examples, the thickness of the second layer of the second plasmonic material can be 200 nm or less (e.g., 190 nm or less, 180 nm or less, 170 nm or less, 160 nm or less, 150 nm or less, 140 nm or less, 130 nm or less, 120 nm or less, 110 nm or less, 100 nm or less, 90 nm or less, 80 nm or less, 70 nm or less, 60 nm or less, 50 nm or less, 45 nm or less, 40 nm or less, 35 nm or less, 30 nm or less, or 25 nm or less). The thickness of the second layer of the second plasmonic material can range from any of the minimum values described above to any of the maximum values described above. For example, the thickness of the second layer of the second plasmonic material can be from 15 nm to 200 nm (e.g., from 15 nm to 100 nm, from 100 nm to 200 nm, from 15 nm to 50 nm, from 50 nm to 100 nm, from 100 nm to 150 nm, from 150 nm to 200 nm, or from 20 nm to 150 nm).

Each of the holes in the second plurality of spaced-apart holes can have an average characteristic dimension. The term "characteristic dimension," as used herein, refers to the largest straight line distance spanning a hole in the plane of the layer (e.g., in the plane of the second layer that is substantially parallel to the first surface of the substrate). For example, in the case of a hole having a substantially circular shape in the plane of the layer, the characteristic dimension of the hole is the diameter of the hole. "Average characteristic dimension" and "mean characteristic dimension" are used interchangeably herein, and generally refer to the statistical mean characteristic dimension of the particles in a population of particles. The characteristic dimension can be measured using methods known in the art, such as evaluation by scanning electron microscopy, transmission electron microscopy, and/or atomic force microscopy.

For example, the second plurality of holes can have an average characteristic dimension of 20 nm or more (e.g., 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 550 nm or more, 600 nm or more, 650 nm or more, 700 nm or more, or 750 nm or more). In some examples, the second plurality of holes can have an average characteristic dimension of 800 nm or less (e.g., 750 nm or less, 700 nm or less, 650 nm or less, 600 nm or less, 550 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, or 30 nm or less). The average characteristic dimension of the second plurality of holes can range from any of the minimum values described above to any of the maximum values described above. For example, the second plurality of holes can have an average characteristic dimension of from 20 nm to 800 nm (e.g., from 20 nm to 400 nm, from 400 nm to 800 nm, from 20 nm to 200 nm, from 200 nm to 400 nm, from 400 nm to 600 nm, from 600 nm to 800 nm, or from 50 nm to 700 nm).

In some examples, the second plurality of spaced-apart holes can be substantially monodisperse. "Monodisperse" and "homogeneous size distribution," as used herein, and generally describe a population of holes where all of the holes have the same or nearly the same characteristic dimension. As used herein, a monodisperse distribution refers to hole distributions in which 80% of the distribution (e.g., 85% of the distribution, 90% of the distribution, or 95% of the distribution) lies within 25% of the mean characteristic dimension (e.g., within 20% of the mean characteristic dimension, within 15% of the mean characteristic dimension, within 10% of the mean characteristic dimension, or within 5% of the mean characteristic dimension).

The second plurality of spaced apart holes can comprise holes of any shape (e.g., a sphere, a rod, an ellipsoid, a triangular prism, a pyramid, a polygon, a cylinder, a rectangular prism, etc.). In some examples, the second plurality of spaced-apart holes can have an isotropic shape. In some examples, the second plurality of spaced-apart holes can have an anisotropic shape. In some examples, each of the holes in the second plurality of spaced-apart holes is substantially cylindrical in shape, such that the diameter of each cylinder is the average characteristic dimension of each of the holes.

The second plurality of spaced apart holes comprise a second array defined by a second unit cell. As used herein, a "unit cell" is the smallest group of holes in the array that constitutes the repeating pattern of the array. The second unit cell can have a first principle axis and a second principle axis with a second included angle between the first principle axis and the second principle axis. The second array is built up of repetitive translations of the second unit cell along its principle axes.

The first principle axis of the second unit cell has a length that is the distance separating each hole in the second array from its neighboring hole (edge to edge) along the first principle axis. In some examples, the length of the first principle axis in the second array can be 60 nm or more (e.g., 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 175 nm or more, 200 nm or more, 225 nm or more, 250 nm or more, 275 nm or more, 300 nm or more, 350 nm or more, 400 nm or more, 450 nm or more, 500 nm or more, 600 nm or more, 700 nm or more, 800 nm or more, or 900 nm or more).

In some examples, the length of the first principle axis in the second array can be 1000 nm or less (e.g., 900 nm or less, 800 nm or less, 700 nm or less, 600 nm or less, 500 nm or less, 450 nm or less, 400 nm or less, 350 nm or less, 300 nm or less, 275 nm or less, 250 nm or less, 225 nm or less, 200 nm or less, 175 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, or 70 nm or less). The length of the first principle axis in the second array can range from any of the minimum values described above to any of the maximum values described above. For example, the length of the first principle axis in the second array can be from 60 nm to 1000 nm (e.g., from 60 nm to 500 nm, from 500 nm to 1000 nm, from 60 nm to 200 nm, from 200 nm to 400 nm, from 400 nm to 600 nm, from 600 nm to 800 nm, from 800 nm to 1000 nm, or from 100 nm to 900 nm). In some examples, the length of the first principle axis in the first array can be substantially the same as the length of the first principle axis in the second array.

In some examples, the second plurality of holes can have an average characteristic dimension that is 40% of the length of the first principle axis in the second array or more (e.g., 45% or more, 50% or more, 55% or more, 60% or more, 65% or more, or 70% or more). In some examples, the second plurality of holes can have an average characteristic dimension that is 80% of the length of the first principle axis in the second array or less (e.g., 75% or less, 70% or less, 65% or less, 60% or less, 55% or less, or 50% or less). The average characteristic dimension of the second plurality of holes can range from any of the minimum values described above to any of the maximum values described above. For example, the second plurality of holes can have an average characteristic dimension that is from 40% to 80% of the length of the first principle axis in the second array (e.g., from 40% to 60%, from 60% to 80%, from 40% to 50%, from 50% to 60%, from 60% to 70%, from 70% to 80%, or from 45% to 75%).

The second principle axis of the second unit cell has a length that is the distance separating each hole in the second array from its neighboring hole (edge to edge) along the second principle axis. In some examples, the length of the second principle axis in the second array can be 60 nm or more (e.g., 65 nm or more, 70 nm or more, 75 nm or more, 80 nm or more, 85 nm or more, 90 nm or more, 95 nm or more, 100 nm or more, 110 nm or more, 120 nm or more, 130 nm or more, 140 nm or more, 150 nm or more, 175 nm or more, 200 nm or more, 225 nm or more, 250 nm or more, 275 nm or more, 300 nm or more, 350 nm or more, 400 nm or more, 450 nm or more, 500 nm or more, 600 nm or more, 700 nm or more, 800 nm or more, or 900 nm or more). In some examples, the length of the second principle axis in the second array can be 1000 nm or less (e.g., 900 nm or less, 800 nm or less, 700 nm or less, 600 nm or less, 500 nm or less, 450 nm or less, 400 nm or less, 350 nm or less, 300 nm or less, 275 nm or less, 250 nm or less, 225 nm or less, 200 nm or less, 175 nm or less, 150 nm or less, 140 nm or less, 130 nm or less, 120 nm or less, 110 nm or less, 100 nm or less, 95 nm or less, 90 nm or less, 85 nm or less, 80 nm or less, 75 nm or less, or 70 nm or less). The length of the second principle axis in the second array can range from any of the minimum values described above to any of the maximum values described above. For example, the length of the second principle axis in the second array can be from 60 nm to 1000 nm (e.g., from 60 nm to 500 nm, from 500 nm to 1000 nm, from 60 nm to 200 nm, from 200 nm to 400 nm, from 400 nm to 600 nm, from 600 nm to 800 nm, from 800 nm to 1000 nm, or from 100 nm to 900 nm). In some examples, the length of the second principle axis in the second array can be substantially the same as the length of the first principle axis in the second array. In some examples, the length of the second principle axis in the second array can be substantially the same as the length of the second principle axis in the first array. In some examples, the length of the first principle axis in the first array, the length of the second principle axis in the first array, the length of the first principle axis in the second array, and the length of the second principle axis in the second array are substantially the same.

In some examples, the second plurality of holes can have an average characteristic dimension that is 40% of the length of the second principle axis in the second array or more (e.g., 45% or more, 50% or more, 55% or more, 60% or more, 65% or more, or 70% or more). In some examples, the second plurality of holes can have an average characteristic dimension that is 80% of the length of the second principle axis in the second array or less (e.g., 75% or less, 70% or less, 65% or less, 60% or less, 55% or less, or 50% or less). The average characteristic dimension of the second plurality of holes can range from any of the minimum values described above to any of the maximum values described above. For example, the second plurality of holes can have an average characteristic dimension that is from 40% to 80% of the length of the second principle axis in the second array (e.g., from 40% to 60%, from 60% to 80%, from 40% to 50%, from 50% to 60%, from 60% to 70%, from 70% to 80%, or from 45% to 75%).

The second unit cell can be of any shape. In some examples, the second unit cell is in the shape of a triangle. In some examples, the second unit cell is in the shape of a quadrilateral (e.g., a rectangle, a parallelogram, or the like).

The second included angle between the first principle axis and the second principle axis of the second unit cell can, for example, be 45° or more (e.g., 50° or more, 55° or more, 60° or more, 65° or more, 70° or more, 75° or more, 80° or more, 85° or more, 90° or more, 95° or more, 100° or more, 105° or more, 110° or more, 115° or more, 120° or more, 125° or more, or 130° or more). In some examples, the second included angle between the first principle axis and the second principle axis of the second unit cell can be 135° or less (e.g., 130° or less, 125° or less, 120° or less, 115° or less, 110° or less, 105° or less, 100° or less, 95° or less, 90° or less, 85° or less, 80° or less, 75° or less, 70° or less, 65° or less, 60° or less, 55° or less, or 50° or less). The second included angle between the first principle axis and the second principle axis of the second unit cell can range from any of the minimum values described above to any of the maximum values described above. For example, the second included angle between the first principle axis and the second principle axis of the second unit cell can be from 45° to 135° (e.g., from 45° to 90°, from 90° to 135°, from 45° to 60°, from 60° to 75°, from 75° to 90°, from 90° to 105°, from 105° to 120°, from 120° to 135°, from 80° to 100°, or from 60° to) 120°. In some examples, the second included angle is 90°.

In some examples, the first nanostructured layer and the second nanostructured layer can be substantially the same.

The first nanostructured layer is located proximate the second nanostructured layer and the first principle axis of the first array is rotated at a rotation angle compared to the first principle axis of the second array. The rotation angle can, for example, be 1° or more (e.g., 2° or more, 3° or more, 4° or more, 5° or more, 6° or more, 7° or more, 8° or more, 9° or more, 10° or more, 15° or more, 20° or more, 25° or more, 30° or more, 35° or more, 40° or more, 45° or more, 50° or more, 55° or more, 60° or more, 65° or more, 70° or more, 75° or more, or 80° or more). In some examples, the rotation angle can be 90° or less (e.g., 85° or less, 80° or less, 75° or less, 70° or less, 65° or less, 60° or less, 55° or less, 50° or less, 45° or less, 40° or less, 35° or less, 30° or less, 25° or less, 20° or less, 15° or less, 10° or less, 9° or less, 8° or less, 7° or less, 6° or less, or 5° or less). The rotation angle can range from any of the minimum values described above to any of the maximum values described above. For example, the rotation angle can be from 1° to 90° (e.g., from 1° to 45°, from 45° to 90°, from 1° to 30°, from 30° to 60°, from 60° to 90°, or from 5° to 85°).

In some examples, the second nanostructured layer is disposed on (e.g., in contact with) the first nanostructured layer. In some examples, the nanostructured plasmonic material further comprises a third layer located between the first nanostructured layer and the second nanostructured layer and in contact with the first nanostructured layer and the second nanostructured layer. The third layer can, for example, comprise a dielectric material. In some examples, the third layer can comprise glass, quartz, silicon dioxide, silicon nitride, a polymer, a hydrogel, or a combination thereof.

The third layer can, for example, have a thickness of 1 nm or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 55 nm or more, 60 nm or more, 65 nm or more, 70 nm or more, 75 nm or more, 80 nm or more, 85 nm or more, or 90 nm or more). In some examples, the thickness of the third layer can be 100 nm or less (e.g., 95 nm or less, 90 nm or less, 85 nm or less, 80 nm or less, 75 nm or less, 70 nm or less, 65 nm or less, 60 nm or less, 55 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, or 5 nm or less). The thickness of the third layer can range from any of the minimum values described above to any of the maximum values described above. For example, the thickness of the third layer can be from 1 nm to 100 nm (e.g., from 1 nm to 50 nm, from 50 nm to 100 nm, from 1 nm to 20 nm, from 20 nm to 40 nm, from 40 nm to 60 nm, from 60 nm to 80 nm, from 80 nm to 100 nm, or from 5 nm to 90 nm).

The thickness of the first nanostructured layer, the thickness of the second nanostructured layer, the presence of the third layer, the thickness of the third layer (if present), the average characteristic dimension of the first plurality of holes and/or the second plurality of holes, the composition of the first layer of the first plasmonic material, the composition of the second layer of the second plasmonic material, the separation between each hole within the first array and/or the second array (e.g., the length of the first principle axis and/or the second principle axis in the first array and/or the second array), the first included angle, the second included angle, the rotation angle, or combination thereof can be selected in view of a variety of factors, for example to affect the optical properties of the nanostructured plasmonic material.

In some examples, the thickness of the first nanostructured layer, the thickness of the second nanostructured layer, the presence of the third layer, the thickness of the third layer (if present), the average characteristic dimension of the first plurality of holes and/or the second plurality of holes, the composition of the first layer of the first plasmonic material, the composition of the second layer of the second plasmonic material, the separation between each hole within the first array and/or the second array (e.g., the length of the first principle axis and/or the second principle axis in the first array and/or the second array), the first included angle, the second included angle, the rotation angle, or combination thereof can be selected such that the plasmon resonance energy of the chiral plasmonic substrate overlaps with at least a portion of the electromagnetic radiation used to illuminate the chiral plasmonic substrate.

Referring now to FIG. 1, the chiral plasmonic substrate 102 can comprise: a first nanostructured layer 104 comprising a first layer of a first plasmonic material 106 permeated by a first plurality of spaced-apart holes 108, and a second nanostructured layer 120 comprising a second layer of a second plasmonic material 122 permeated by a second plurality of spaced-apart holes 124.

Figure 2:
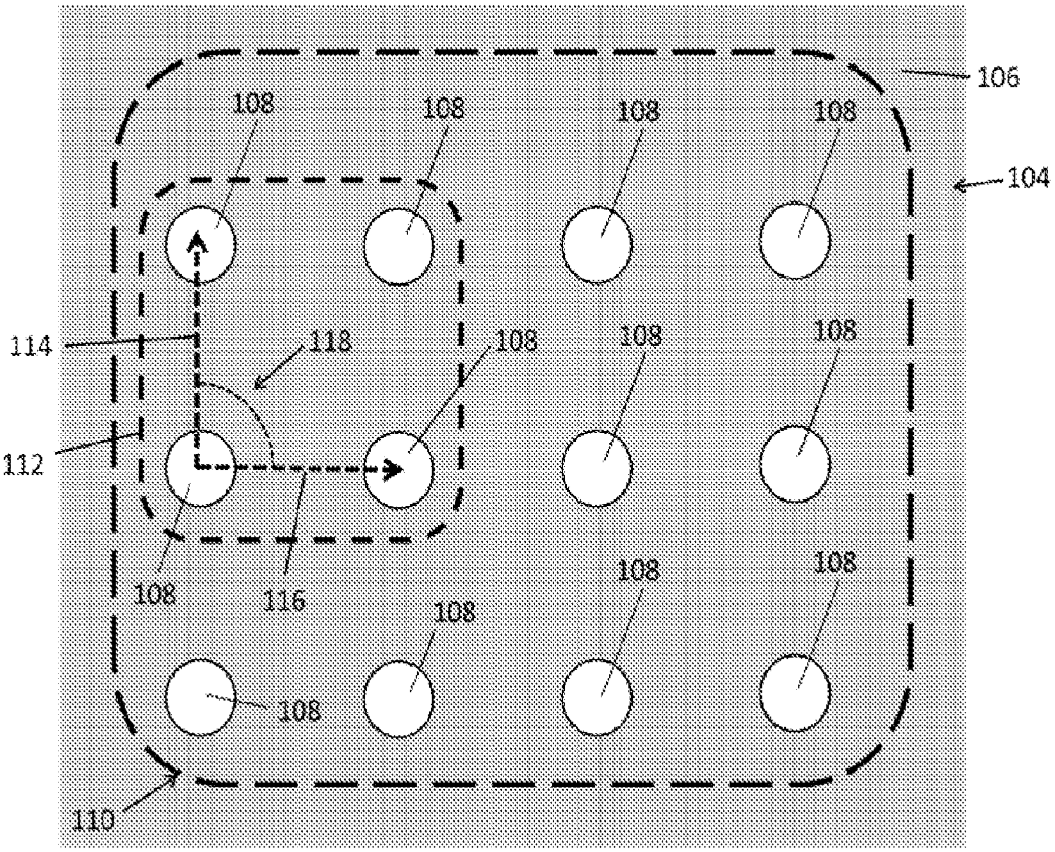
FIG. 2 is a schematic illustration of an example first nanostructured layer of an example chiral plasmonic substrate as disclosed herein.
Figure 3:
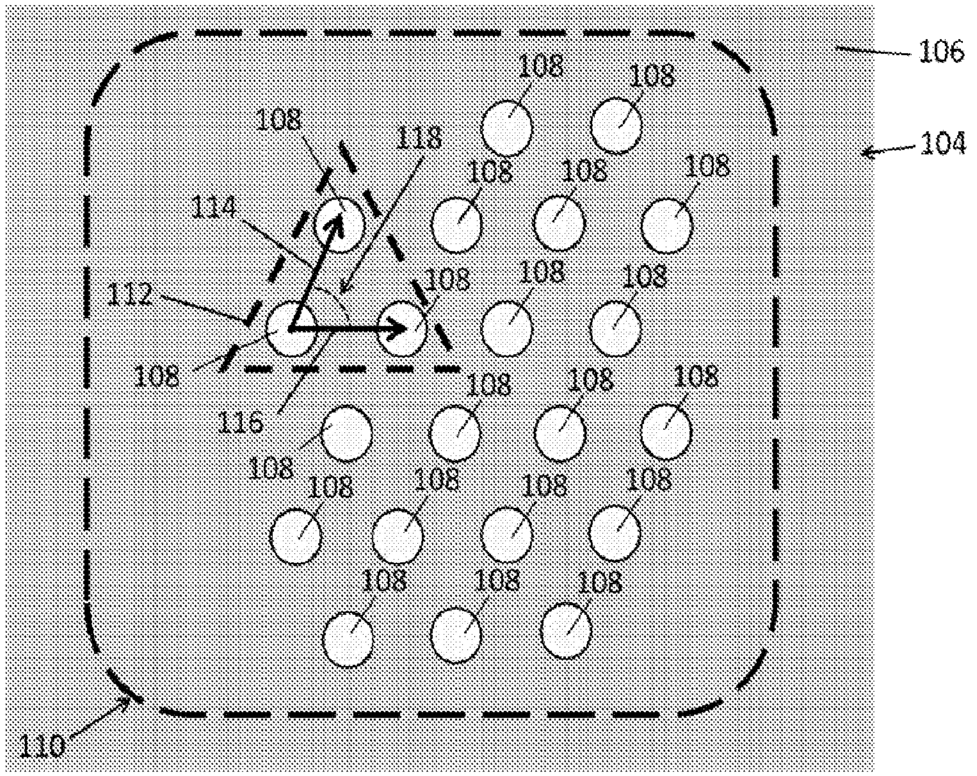
FIG. 3 is a schematic illustration of an example first nanostructured layer of an example chiral plasmonic substrate as disclosed herein.

Referring now to FIG. 2 and FIG. 3, the first plurality of spaced apart holes 108 comprise a first array 110 defined by a first unit cell 112, the first unit cell 112 having: a first principle axis 114 and a second principle axis 116 with a first included angle 118 between the first principle axis 114 and the second principle axis 116; wherein the first principle axis 114 has a length that is the distance separating each hole in the first array 110 from its neighboring hole (edge to edge) along the first principle axis 114; and wherein the second principle axis 116 has a length that is the distance separating each hole in the first array 110 from its neighboring hole (edge to edge) along the second principle axis 116. Referring now to FIG. 2, in some examples, the first unit cell 112 can be in the shape of a rectangle. Referring now to FIG. 3, in some examples, the first unit cell 112 can be in the shape of a triangle.

Figure 4:
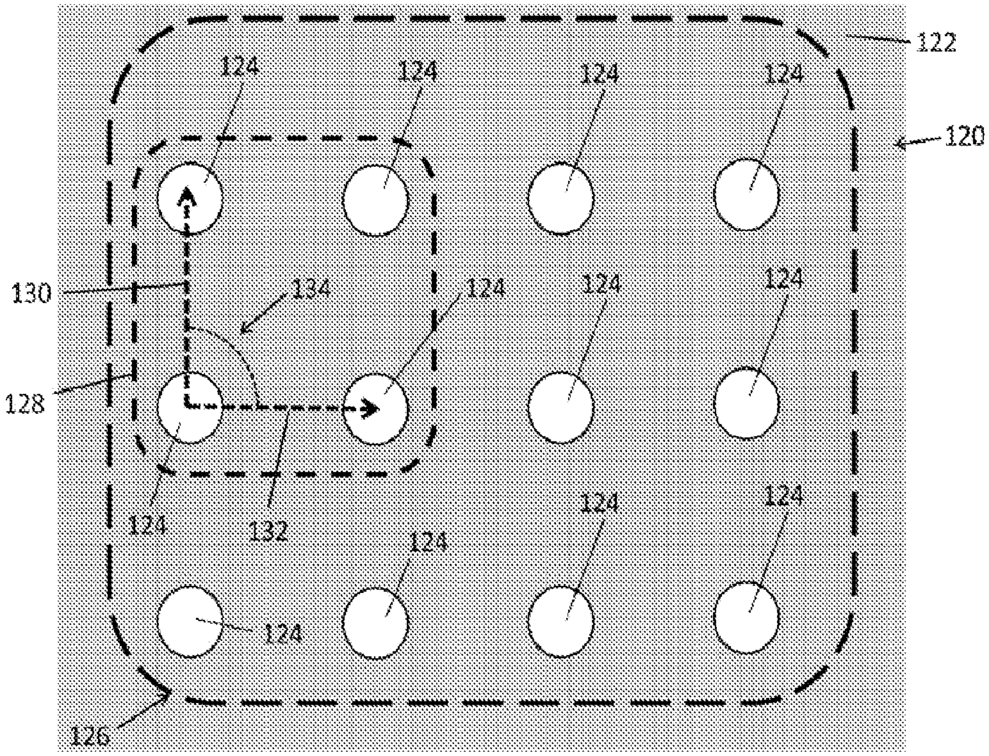
FIG. 4 is a schematic illustration of an example second nanostructured layer of an example chiral plasmonic substrate as disclosed herein.
Figure 5:
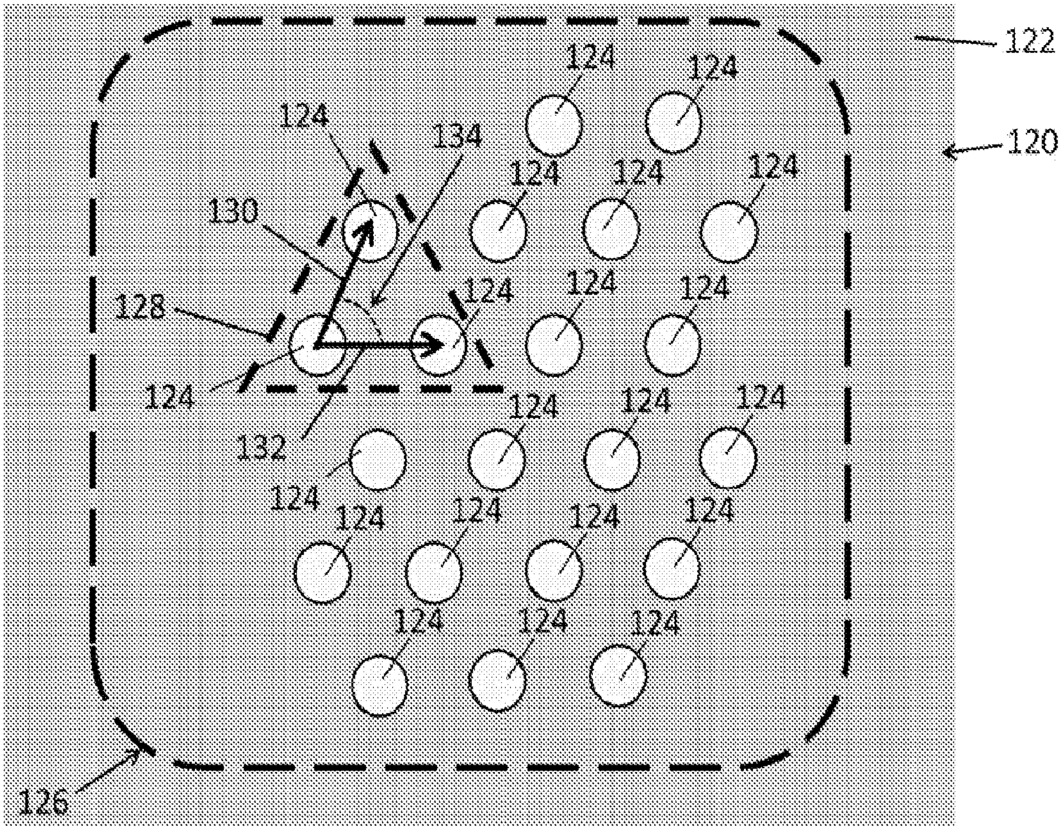
FIG. 5 is a schematic illustration of an example second nanostructured layer of an example chiral plasmonic substrate as disclosed herein.

Referring now to FIG. 4 and FIG. 5, the second plurality of spaced apart holes 124 comprise a second array 126 defined by a second unit cell 128, the second unit cell 128 having: a first principle axis 130 and a second principle axis 132 with a second included angle 134 between the first principle axis 130 and the second principle axis 132; wherein the first principle axis 130 has a length that is the distance separating each hole in the second array 126 from its neighboring hole (edge to edge) along the first principle axis 130; and wherein the second principle axis 132 has a length that is the distance separating each hole in the second array 126 from its neighboring hole (edge to edge) along the second principle axis 132. Referring now to FIG. 4, in some examples, the second unit cell 128 can be in the shape of a rectangle. Referring now to FIG. 5, in some examples, the second unit cell 128 can be in the shape of a triangle.

In some examples, the first nanostructured layer 104 and the second nanostructured layer 120 are substantially the same.

Figure 6:
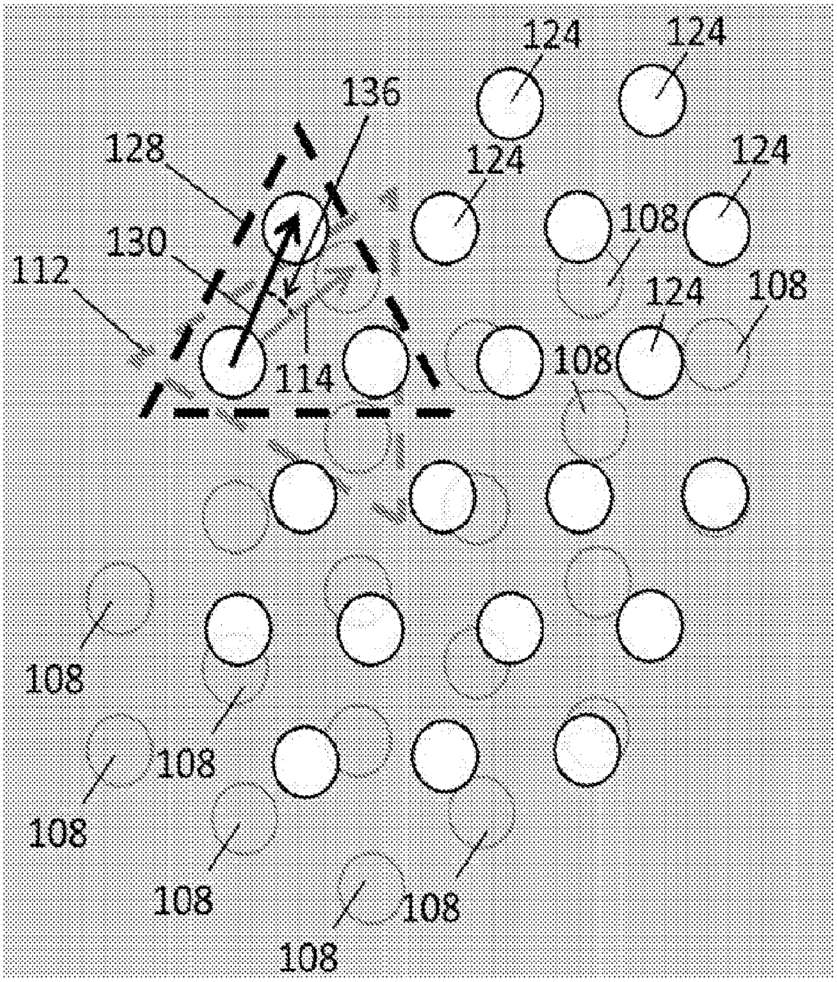
FIG. 6 is a schematic illustration of an example first nanostructured layer and an example second nanostructured layer of an example chiral plasmonic substrate as disclosed herein.

Referring now to FIG. 6, the second nanostructured layer 120 is located proximate the first nanostructured layer 104 and the first principle axis 114 of the first unit cell 112 is rotated at a rotation angle 136 compared to the first principle axis 130 of the second unit cell 128. In some examples, the second nanostructured layer 120 is disposed on the first nanostructured layer 104.

Figure 7:
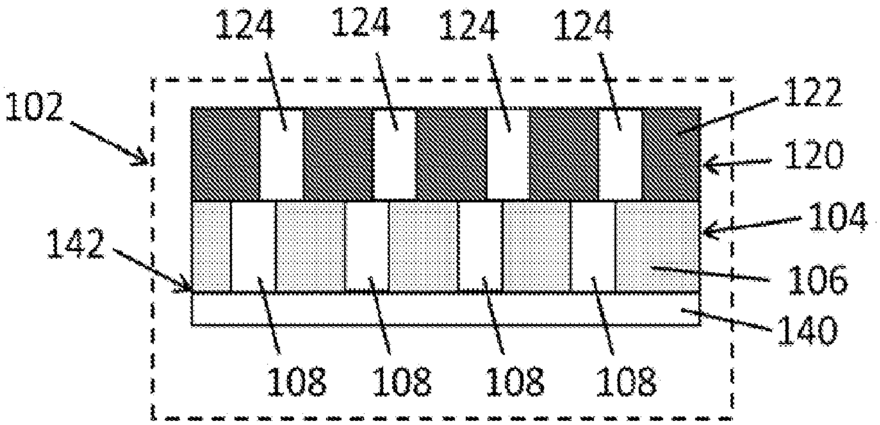
FIG. 7 is a schematic illustration of an example chiral plasmonic substrate as disclosed herein.

Referring now to FIG. 7, in some examples, the nanostructured plasmonic material can further comprise a substrate 140 having a first surface 142, wherein the first nanostructured layer 104 is disposed on the first surface 142.

Figure 8:
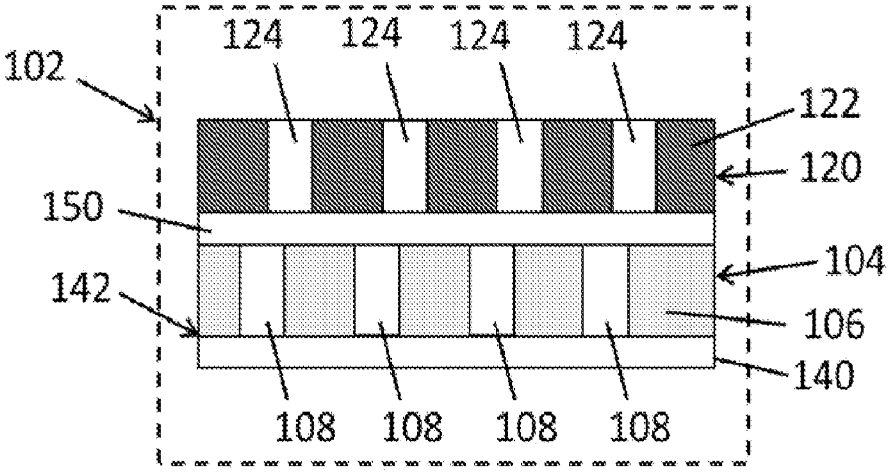
FIG. 8 is a schematic illustration of an example chiral plasmonic substrate as disclosed herein.

Referring now to FIG. 8, in some examples, the nanostructured plasmonic material 102 further comprises a third layer 150 located between the first nanostructured layer 104 and the second nanostructured layer 120 and in contact with the first nanostructured layer 104 and the second nanostructured layer 120.

In some examples, the methods disclosed herein can further comprise making the chiral plasmonic substrate. For example, the chiral plasmonic substrate can be made by methods comprising: forming the first nanostructured layer; forming the second nanostructured layer; and disposing the second nanostructured layer on the first nanostructured layer or on the third layer such that the first principle axis of the first array is rotated at a rotation angle compared to the first principle axis of the second array, thereby forming the chiral plasmonic substrate. Forming the first nanostructured layer and/or the second nanostructured layer can, for example, comprise electron beam lithography, nanoimprinting, nanosphere lithography, focused ion beam lithography, injection molding, block copolymer lithography, photolithography, or a combination thereof. Disposing the second nanostructured layer on the first nanostructured layer or on the third layer can, for example, comprise dip coating, spin coating, pick-up of floating layers, and combinations thereof.

The chiral plasmonic substrate is in thermal contact with a liquid sample comprising a plurality of chiral analytes. The liquid sample can, in some examples, further comprise a solvent. The solvent can, for example, comprise tetrahydrofuran (THF), N-methyl-2-pyrrolidone (NMP), dimethylformamide (DMF), N-methylformamide, formamide, dichloromethane ($CH_2Cl_2$), ethylene glycol, polyethylene glycol, glycerol, alkane diol, ethanol, methanol, propanol, isopropanol, water, acetonitrile, chloroform, toluene, methyl acetate, ethyl acetate, acetone, hexane, heptane, tetraglyme, propylene carbonate, diglyme, dimethyl sulfoxide (DMSO), dimethoxyethane, xylene, dimethylacetamide, or combinations thereof. In some examples, solvent comprises water, such that the liquid sample comprises an aqueous solution.

The liquid sample can comprise any liquid sample of interest. By way of example the liquid sample can comprise a bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningeal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples. In some examples, the bodily fluid comprises urine, plasma, blood, or a combination thereof. In some examples, the bodily fluid comprises urine.

As used herein, a chiral analyte is any molecule that has a non-superposable mirror image. The symmetry of a molecule (or any other object) determines whether it is chiral. The two mirror images of a chiral molecule are called enantiomers, or optical isomers.

The plurality of chiral analytes can, for example, comprise a biomolecule, a macromolecule, a pathogen (e.g., bacteria, virus, fungi, parasite, or protozoa), a drug, or a combination thereof. As used herein, a biomolecule can comprise, for example, a nucleotide, an enzyme, an amino acid, a protein (e.g., a glycoprotein, a lipoprotein, or a recombinant protein), a polysaccharide, a lipid, a nucleic acid, a vitamin, a hormone, a prohormone, a peptide (natural, modified, or chemically synthesized), a polypeptide, polynucleotide (e.g., DNA or RNA, an oligonucleotide, an aptamer, or a DNAzyme), or a combination thereof. In some examples, the plurality of chiral analytes can comprise a macromolecule, such as a cyclodextrins, calixarenes, cucurbiturils, crown ethers, cyclophanes, cryptands, nanotubes, fullerenes, and dendrimers.

In some embodiments, the plurality of chiral analytes can comprise a drug. Examples of chiral drugs include, but are not limited to, acebutolol, acenocoumarol, alprenolol, alacepril, albuterol, almeterol, alogliptin, amoxicillin, amphetamine, ampicillin, arformoterol, armodafinil, atamestane, atenolol, atorvastatin, azlocillin, aztreonam, benazepril, benoxaprophen,, benzylpenicillin, betaxolol, bupivacaine, calstran, captopril, carvedilol, cefalexin, cefaloglycin, cefamandole, cefapirin, cefazaflur, cefonicid, ceforanide, cefpimizole, cefradine, cefroxadine, ceftezole, cefuroximo, cetirizine, cilazapril, citalopram, cloxacillin, cyclophosphamide, delapril, deprenyl, dexbrompheniramine, dexchlorpheniramine, dexfenfluramine, dexibuprofen, dexketoprofen, dexlansoprazole, dexmedetomidine, dexmethylphenidate, dexpramipexole, dexrazoxane, dextroamphetamine, dextromethorphan, dextrorphan, dicloxacillin, diltiazem, disopyramide, drospirenone, enalapril, epicillin, escitalopram, escitazolam, esketamine, eslicarbazepine acetate, esmirtazapine, esomeprazole, esreboxetine, eszopiclone, ethambutol, ethosuximide, exemestane, felodipine, fenprofen, fimasartan, flecainide, flucloxacillin, fluoxetine, gestonorone, hexobarbitol, ibuprofen, idapril, imipenem, irinotecan hydrochloride, isoflurane, ketoprofen, ketamine, labetalol, lansoprazole, levacetylmethadol, levetiracetam, levoamphetamine, levobetaxolol, levobupivacaine, levalbuterol, levocetirizine, levofenfluramine, levofloxacin, levomethamphetamine, levomethorphan, levomilnacipran, levonorgestrel, levopropylhexedrine, levorphanol, levosalbutamol, levosulpiride, levoverbenone, lisinopril, loratadine, lorazepam, mandipine, mecillinam, mephenytoine, mephobarbital, meropenem, methadone, methamphetamine, methorphan, methylphenidate, metoprolol, mezlocillin, milnacipran, modafinil, moexipril, moxalactam, naproxen, nicardipine, nimodipine, nisoldipine, norpseudoephedrine, ofloxacin, omeprazole, oxacillin, oxazepam, pantoprazole, penbutolol, penicillamine, penicillin, perindopril, pentobarbital, phenoxymethylpenicillin, pindolol, piperacillin, prilocaine, propafenone, propanolol, quinapril, ramipril, rentiapril, salbutamol, secobarbital, selegiline, spirapril, sotalol, temazepam, terfenadine, terbutaline, thalidomide, thiohexital, thiopental, timolol, tocainide, trandolapril, verapamil, varvedilol, warfarine, zofenopril, zopiclone, and combinations thereof.

In some examples, the plurality of chiral analytes can comprise a biomarker (i.e., a molecular indicator associated with a particular pathological or physiological state). Examples of biomarkers include proteins, peptides, polypeptides, hormones, prohormones, lipids, glycoproteins, carbohydrates, DNA, RNA, and combinations thereof. In some examples, the plurality of chiral analytes can comprise a metabolite. In some examples, the plurality of chiral analytes can comprise a metabolite such as any of those described in: Bouatra et al. *PLOS ONE,* 2013, 8(9), e73076; and The Human Metabolome Database (https://hmdb.ca/metabolites); each of which are hereby incorporated herein for their description of chiral metabolites. In some examples, the plurality of chiral analytes comprise glucose, lactate, or a combination thereof.

In some embodiments, the plurality of chiral analytes can comprise a pathogen (e.g., bacteria, virus, fungi, parasite, or protozoa), a biomarker indicative of a pathogen, or a combination thereof.

Viruses that are suitable for the methods and uses described herein can include both DNA viruses and RNA viruses. Exemplary viruses can belong to the following non-exclusive list of families Adenoviridae, Arenaviridae, Astroviridae, Baculoviridae, Barnaviridae, Betaherpesvirinae, Bimaviridae, Bromoviridae, Bunyaviridae, Caliciviridae, Chordopoxvirinae, Circoviridae, Comoviridae, Coronaviridae, Cystoviridae, Corticoviridae, Entomopoxvirinae, Filoviridae, Flaviviridae, Fuselloviridae, Geminiviridae, Hepadnaviridae, Herpesviridae, Gammaherpesvirinae, Inoviridae, Iridoviridae, Leviviridae, Lipothrixviridae, Microviridae, Myoviridae, Nodaviridae, Orthomyxoviridae, Papovaviridae, Paramyxoviridae, Paramyxovirinae, Partitiviridae, Parvoviridae, Phycodnaviridae, Picornaviridae, Plasmaviridae, Pneumovirinae, Podoviridae, Polydnaviridae, Poty viridae, Poxviridae, Reoviridae, Retroviridae, Rhabdoviridae, Sequiviridae, Siphoviridae, Tectiviridae, Tetraviridae, Togaviridae, Tombusviridae, and Totiviridae.

Specific examples of viruses include, but are not limited to, Mastadenovirus, Adenovirus, Human adenovirus 2, Aviadenovirus, African swine fever virus, arenavirus, Lymphocytic choriomeningitis virus, Ippy virus, Lassa virus, Arterivirus, Human astrovirus 1, Nucleopolyhedrovirus, Autographa californica nucleopolyhedrovirus, Granulovirus, Plodia interpunctella granulovirus, Badnavirus, Commelina yellow mottle virus, Rice tungro bacilliform, Barnavirus, Mushroom bacilliform virus, Aquabimavirus, Infectious pancreatic necrosis virus, Avibirnavirus, Infectious bursal disease virus, Entomobirnavirus, Drosophila X virus, Alfamovirus, Alfalfa mosaic virus, Ilarvirus, Ilarvirus Subgroups 1-10, Tobacco streak virus, Bromovirus, Brome mosaic virus, Cucumovirus, Cucumber mosaic virus, Bhanja virus Group, Kaisodi virus, Mapputta virus, Okola virus, Resistencia virus, Upolu virus, Yogue virus, Bunyavirus, Anopheles A virus, Anopheles B virus, Bakau virus, Bunyamwera virus, Bwamba virus, C virus, California encephalitis virus, Capim virus, Gamboa virus, Guama virus, Koongol virus, Minatitlan virus, Nyando virus, Olifantsvlei virus, Patois virus, Simbu virus, Tete virus, Turlock virus, Hantavirus, Hantaan virus, Nairovirus, Crimean-Congo hemorrhagic fever virus, Dera Ghazi Khan virus, Hughes virus, Nairobi sheep disease virus, Qalyub virus, Sakhalin virus, Thiafora virus, Crimean-congo hemorrhagic fever virus, Phlebovirus, Sandfly fever virus, Bujaru complex, Candiru complex, Chilibre complex, Frijoles complex, Punta Toro complex, Rift Valley fever complex, Salehabad complex, Sandfly fever Sicilian virus, Uukuniemi virus, Uukuniemi virus, Tospovirus, Tomato spotted wilt virus, Calicivirus, Vesicular exanthema of swine virus, Capillovirus, Apple stem grooving virus, Carlavirus, Carnation latent virus, Caulimovirus, Cauliflower mosaic virus, Circovirus, Chicken anemia virus, Closterovirus, Beet yellows virus, Comovirus, Cowpea mosaic virus, Fabavirus, Broad bean wilt virus 1, Nepovirus, Tobacco ringspot virus, Coronavirus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Torovirus, Berne virus, Breda virus, Corticovirus, Alteromonas phage PM2, Pseudomonas Phage phi6, Deltavirus, Hepatitis delta virus, Hepatitis D virus, Hepatitis E virus, Dianthovirus, Carnation ringspot virus, Red clover necrotic mosaic virus, Sweet clover necrotic mosaic virus, Enamovirus, Pea enation mosaic virus, Filovirus, Marburg virus, Ebola virus, Ebola virus Zaire, Flavivirus, Yellow fever virus, Tick-borne encephalitis virus, Rio Bravo Group, Japanese encephalitis, Tyuleniy Group, Ntaya Group, Uganda S Group, Dengue Group, Modoc Group, Pestivirus, Bovine diarrhea virus, Hepatitis C virus, Furovirus, Soil-borne wheat mosaic virus, Beet necrotic yellow vein virus, Fusellovirus, Sulfobolus virus 1, Subgroup I, II, and III geminivirus, Maize streak virus, Beet curly top virus, Bean golden mosaic virus, Orthohepadnavirus, Hepatitis B virus, Avihepadnavirus, Alphaherpesvirinae, Simplexvirus, Human herpesvirus 1, Herpes Simplex virus-1, Herpes Simplex virus-2, Varicellovirus, Varicella-Zoster virus, Epstein-Barr virus, Human herpesvirus 3, Cytomegalovirus, Human herpesvirus 5, Muromegalovirus, Mouse cytomegalovirus 1, Roseolovirus, Human herpesvirus 6, Lymphocryptovirus, Human herpesvirus 4, Rhadinovirus, Ateline herpesvirus 2, Hordeivirus, Barley stripe mosaic virus, Hypoviridae, Hypovirus, Cryphonectria hypovirus 1-EP713, Idaeovirus, Raspberry bushy dwarf virus, Inovirus, Coliphage fd, Plectrovirus, Acholeplasma phage L51, Iridovirus, Chilo iridescent virus, Chloriridovirus, Mosquito iridescent virus, Ranavirus, Frog virus 3, Lymphocystivirus, Lymphocystis disease virus flounder isolate, Goldfish virus 1, Levivirus, Enterobacteria phage MS2, Allolevirus, Enterobacteria phage Qbeta, Lipothrixvirus, Thermoproteus virus 1, Luteovirus, Barley yellow dwarf virus, Machlomovirus, Maize chlorotic mottle virus, Marafivirus, Maize rayado fino virus, Microvirus, Coliphage phiX174, Spiromicrovirus, Spiroplasma phage 4, Bdellomicrovirus, Bdellovibrio phage MAC 1, Chlamydiamicrovirus, Chlamydia phage 1, T4-like phages, coliphage T4, Necrovirus, Tobacco necrosis virus, Nodavirus, Nodamura virus, Influenzavirus A, B and C, Thogoto virus, Polyomavirus, Murine polyomavirus, Papillomavirus, Rabbit (Shope) Papillomavirus, Paramyxovirus, Human parainfluenza virus 1, Morbillivirus, Measles virus, Rubulavirus, Mumps virus, Pneumovirus, Human respiratory syncytial virus, Partitivirus, Gaeumannomyces graminis virus 019/6-A, Chrysovirus, Penicillium chrysogenum virus, Alphacryptovirus, White clover cryptic viruses 1 and 2, Betacryptovirus, Parvovirinae, Parvovirus, Minute mice virus, Erythrovirus, B19 virus, Dependovirus, Adeno-associated virus 1, Densovirinae, Densovirus, Junonia coenia densovirus, Iteravirus, Bombyx mori virus, Contravirus, Aedes aegypti densovirus, Phycodnavirus, 1-Paramecium bursaria Chlorella NC64A virus group, Paramecium bursaria chlorella virus 1, 2~ Paramecium bursaria Chlorella Pbi virus, 3-Hydra viridis Chlorella virus, Enterovirus, Poliovirus, Human poliovirus 1, Rhinovirus, Human rhinovirus 1A, Hepatovirus, Human hepatitis A virus, Cardiovirus, Encephalomyocarditis virus, Aphthovirus, Foot-and-mouth disease virus, Plasmavirus, Acholeplasma phage L2, Podovirus, Coliphage T7, Ichnovirus, Campoletis sonorensis virus, Bracovirus, Cotesia melanoscela virus, Potexvirus, Potato virus X, Potyvirus, Potato virus Y, Rymovirus, Ryegrass mosaic virus, Bymovirus, Barley yellow mosaic virus, Orthopoxvirus, Vaccinia virus, Parapoxvirus, Orf virus, Avipoxvirus, Fowlpox virus, Capripoxvirus, Sheep pox virus, Leporipoxvirus, Myxoma virus, Suipoxvirus, Swinepox virus, Molluscipoxvirus, Molluscum contagiosum virus, Yatapoxvirus, Yaba monkey tumor virus, Entomopoxviruses A, B, and C, Melolontha melolontha entomopoxvirus, Amsacta moorei entomopoxvirus, Chironomus luridus entomopoxvirus, Orthoreovirus, Mammalian orthoreoviruses, reovirus 3, Avian orthoreoviruses, Orbivirus, African horse sickness viruses 1, Bluetongue viruses 1, Changuinola virus, Corriparta virus, Epizootic hemarrhogic disease virus 1, Equine encephalosis virus, Eubenangee virus group, Lebombo virus, Orungo virus, Palyam virus, Umatilla virus, Wallal virus, Warrego virus, Kemerovo virus, Rotavirus, Groups A-F rotaviruses, Simian rotavirus SA11, Coltivirus, Colorado tick fever virus, Aquareovirus, Groups A-E aquareoviruses, Golden shiner virus, Cypovirus, Cypovirus types 1-12, Bombyx mori cypovirus 1, Fijivirus, Fijivirus groups 1-3, Fiji disease virus, Fijivirus groups 2-3, Phytoreovirus, Wound tumor virus, Oryzavirus, Rice ragged stunt, Mammalian type B retroviruses, Mouse mammary tumor virus, Mammalian type C retroviruses, Murine Leukemia Virus, Reptilian type C oncovirus, Viper retrovirus, Reticuloendotheliosis virus, Avian type C retroviruses, Avian leukosis virus, Type D Retroviruses, Mason-Pfizer monkey virus, BLV-HTLV retroviruses, Bovine leukemia virus, Lentivirus, Bovine lentivirus, Bovine immunodeficiency virus, Equine lentivirus, Equine infectious anemia virus, Feline lentivirus, Feline immunodeficiency virus, Canine immunodeficiency virus Ovine/caprine lentivirus, Caprine arthritis encephalitis virus, Visna/maedi virus, Primate lentivirus group, Human immunodeficiency virus 1, Human immunodeficiency virus 2, Human immunodeficiency virus 3, Simian immunodeficiency virus, Spumavirus, Human spuma virus, Vesiculovirus, Vesicular stomatitis virus, Vesicular stomatitis Indiana virus, Lyssavirus, Rabies virus, Ephemerovirus, Bovine ephemeral fever virus, Cytorhabdovirus, Lettuce necrotic yellows virus, Nucleorhabdovirus, Potato yellow dwarf virus, Rhizidiovirus, Rhizidiomyces virus, Sequivirus, Parsnip yellow fleck virus, Waikavirus, Rice tungro spherical virus, Lambda-like phages, Coliphage lambda, Sobemovirus, Southern bean mosaic virus, Tectivirus, Enterobacteria phage PRD1, Tenuivirus, Rice stripe virus, Nudaurelia capensis beta-like viruses, Nudaurelia beta virus, Nudaurelia capensis omega-like viruses, Nudaurelia omega virus, Tobamovirus, Tobacco mosaic virus (vulgare strain; ssp. NC82 strain), Tobravirus, Tobacco rattle virus, Alphavirus, Sindbis virus, Rubivirus, Rubella virus, Tombusvirus, Tomato bushy stunt, virus, Carmovirus, Carnation mottle virus, Tumip crinkle virus, Totivirus, Saccharomyces cerevisiae virus, Giardiavirus, *Giardia lamblia* virus, Leishmaniavirus, Leishmania brasiliensis virus 1-1, Trichovirus, Apple chlorotic leaf spot virus, Tymovirus, Turnip yellow mosaic virus, Umbravirus, Carrot mottle virus, Variola virus, Coxsackie virus, Dengue virus, Rous sarcoma virus, Zika virus, Lassa fever virus, Eastem Equine Encephalitis virus, Venezuelan equine encephalitis virus, Western equine encephalitis virus, St. Louis Encephalitis virus, Murray Valley fever virus, West Nile virus, Human T-cell Leukemia virus type-1, echovirus, norovirus, and feline calicivirus (FCV).

In some examples, the virus can comprise an influenza virus, a coronavirus, or a combination thereof. Examples of influenza viruses include, but are not limited to, Influenzavirus A (including the HIN1, H2N2, H3N2, HSN1, H7N7, HIN2, H9N2, H7N2, H7N3, H10N7, H7N9, and H6N1 serotypes), Influenzavirus B, Influenzavirus C, and Influenzavirus D. Examples of coronaviruses include, but are not limited to, avian coronavirus (IBV), porcine epidemic diarrhea virus (PEDV), porcine respiratory coronavirus (PRCV), transmissible gastroenteritis virus (TGEV), feline coronavirus (FCoV), feline infectious peritonitis virus (FIPV), feline enteric coronavirus (FECV), canine coronavirus (CCoV), rabbit coronavirus (RaCoV), mouse hepatitis virus (MHV), rat coronavirus (RCoV), sialodacry adenitis virus of rats (SDAV), bovine coronavirus (BCoV), bovine enterovirus (BEV), porcine coronavirus HKU15 (PorCoV HKU15), Porcine epidemic diarrhea virus (PEDV), porcine hemagglutinating encephalomyelitis virus (HEV), turkey bluecomb coronavirus (TCoV), human coronavirus (HCoV)-229E, HCoV-OC43, HCoV—HKUI, HCoV-NL63, Severe Acute Respiratory Syndrome (SARS)-Coronavirus (CoV) (SARS-COV), Severe Acute Respiratory Syndrome (SARS)-Coronavirus (CoV)-2 (SARS-COV-2), and middle east respiratory syndrome (MERS) coronavirus (CoV) (MERS-COV). In some examples, the virus can comprise Severe Acute Respiratory Syndrome (SARS)-Coronavirus (CoV)-2 (SARS-COV-2).

Specific examples of bacteria include, but are not limited to, *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies paratuberculosis, *Nocardia asteroides*, other *Nocardia* species, *Legionella pneumophila*, other *Legionella* species, *Acetinobacter baumanii, Salmonella typhi, Salmonella enterica, Salmonella Typhimurium*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus, Brucella suis, Brucella melitensis*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii*, other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii, rickettsia rickettsia, rickettsia prowazekii, rickettsia typhi*, other *Rickettsial* species, *Ehrlichia* species, *Staphylococcus aureus, Staphylococcus epidermidis, Streptococcus pneumoniae, Streptococcus pyogenes, Streptococcus agalactiae, Streptococcus uberis, Escherichia coli, Vibrio cholerae, Vibrio parahaemolyticus, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani, Clostridium difficile, Clostridium botulinum, Clostridium perfringens*, other *Clostridium* species, *Yersinia enterolitica, Yersinia pestis*, other *Yersinia* species, *Mycoplasma* species, *Bacillus anthracis, Bacillus abortus*, other *Bacillus* species, *Corynebacterium* diptheriae, *Corynebacterium bovis, Francisella tularensis, Chlamydophila psittaci, Campylocavter jejuni, Enterobacter aerogenes, Klebsiella pneumoniae, Klebsiella oxytoca, Proteus* spp., *Serratia marcescens, Trueperella pyogenes*, and *Vibria vulnificus.*

Specific examples of fungi include, but are not limited to, *Candida albicans, Cryptococcus neoformans, Histoplama capsulatum, Aspergillus niger, Aspergillus oryzae, Aspergillus fumigatus, Coccidiodes immitis, Paracoccidioides brasiliensis, Blastomyces dermitidis, Pneumocystis carinii, Penicillium marneffi, Alternaria alternate, Coccidioides immitis, Fusarium oxysporum, Geotrichum candidum*, and *Histoplasma capsulatum.*

Specific examples of parasites include, but are not limited to, *Toxoplasma gondii, Plasmodium falciparum, Plasmodium vivax, Plasmodium malariae*, other *Plasmodium* species, *Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium* spp., *Trypanosoma brucei, Trypanosoma cruzi, Leishmania major*, other *Leishmania* species, *Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis buski, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni*, other *Schistosoma* species, *Trichobilharzia regenti, Trichinella spiralis, Trichinella britovi, Trichinella nelsoni, Trichinella nativa*, and *Entamoeba histolytica.*

The plurality of chiral analytes can have a concentration of 1 picomolar (pM) or more in the liquid sample (e.g., 5 μM or more, 10 μM or more, 50 μM or more, 100 μM or more, 500 μM or more, 1 nanomolar (nM) or more, 5 nM or more, 10 nM or more, 50 nM or more, 100 nM or more, 500 nM or more, 1 micromolar (μM) or more, 5 μM or more, 10 μM or more, 50 μM or more, 100 μM or more, 500 μM or more, 1 millimolar (mM) or more, 5 mM or more, 10 mM or more, or 50 mM or more). In some examples, the plurality of chiral analytes can have a concentration of 100 mM or less in the liquid sample (e.g., 50 mM or less, 10 mM or less, 5 mM or less, 1 mM or less, 500 μM or less, 100 μM or less, 50 μM or less, 10 μM or less, 5 μM or less, 1 μM or less, 500 nM or less, 100 nM or less, 50 nM or less, 10 nM or less, 5 nM or less, 1 nM or less, 500 μM or less, 100 μM or less, 50 μM or less, 10 μM or less, or 5 μM or less). The concentration of the plurality of chiral analytes in the liquid sample can range from any of the minimum values described above to any of the maximum values described above. For example, the plurality of chiral analytes can have a concentration of from 1 picomolar (pM) to 100 millimolar (mM) in the liquid sample (e.g., from 1 μM to 100 μM, from 1 μM to 100 mM, from 1 μM to 1 nM, from 1 nM to 1 μM, from 1 μM to 100 mM, from 1 μM to 1 mM, from 1 μM to 10 μM, from 1 μM to 100 nM, or from 50 μM to 500 μM). In some examples, the plurality of chiral analytes can have a concentration of 100 micromolar (μM) or less or 100 nanomolar (nM) or less in the liquid sample. In some examples, the plurality of chiral analytes have a concentration of from 1 picomolar (pM) to 1 nM in the liquid sample.

The liquid sample can, for example, have a volume of 1 microliter (μL) or more (e.g., 5 μL or more, 10 μL or more, 15 μL or more, 20 μL or more, 25 μL or more, 30 μL or more, 35 μL or more, 40 μL or more, 45 μL or more, 50 μL or more, 60 μL or more, 70 μL or more, 80 μL or more, 90 μL or more, 100 μL or more, 125 μL or more, 150 μL or more, 175 μL or more, 200 μL or more, 225 μL or more, 250 μL or more, 300 μL or more, 350 μL or more, 400 μL or more, 450 μL or more, 500 μL or more, 600 μL or more, 700 μL or more, 800 μL or more, or 900 μL or more). In some examples, the liquid sample can have a volume of 1 milliliter (mL) or less (e.g., 900 μL or less, 800 μL or less, 700 μL or less, 600 μL or less, 500 μL or less, 450 μL or less, 400 μL or less, 350 μL or less, 300 μL or less, 250 μL or less, 225 μL or less, 200 μL or less, 175 μL or less, 150 μL or less, 125 μL or less, 100 μL or less, 90 μL or less, 80 μL or less, 70 μL or less, 60 μL or less, 50 μL or less, 45 μL or less, 40 μL or less, 35 μL or less, 30 μL or less, 25 μL or less, 20 μL or less, 15 μL or less, 10 μL or less, or 5 μL or less). The volume of the liquid sample can range from any of the minimum values described above to any of the maximum values described above. For example, the liquid sample can have a volume of from 1 microliter (μL) to 1 milliliter (mL) (e.g., from 1 μL to 100 μL, from 100 μL to 1 mL, from 1 μL to 10 μL, from 10 μL to 100 μL, from 100 μL to 500 μL, from 500 μL to 1 mL, from 1 μL to 500 μL, from 1 μL to 200 μL, from 1 μL to 50 μL, or from 1 μL to 20 μL).

In some examples, the methods further comprise depositing the liquid sample on the chiral plasmonic substrate. Depositing the liquid sample can, for example, comprise spin-coating, drop casting, dip coating, or a combination thereof. In some examples, the methods can further comprise collecting the liquid sample. In some examples, the methods can further comprise purifying the liquid sample before depositing the liquid sample on the chiral plasmonic substrate. Purifying the liquid sample can, for example, comprise filtering, centrifuging, electrophoresis, or a combination thereof.

The methods described herein comprise illuminating a first location of a chiral plasmonic substrate with electromagnetic radiation; wherein the electromagnetic radiation comprises a wavelength that overlaps with at least a portion of the plasmon resonance energy of the chiral plasmonic substrate such that the chiral plasmonic substrate converts at least a portion of the electromagnetic radiation into thermal energy; and wherein the chiral plasmonic substrate is in thermal contact with a liquid sample comprising a plurality of chiral analytes; thereby: generating a bubble at a location in the liquid sample proximate to the first location of the chiral plasmonic substrate via plasmon-enhanced photothermal effects, the bubble having a gas-liquid interface with the liquid sample and a gas-solid interface with the chiral plasmonic substrate.

The bubble can, for example, have a diameter of 500 nanometers (nm) or more (e.g., 550 nm or more, 600 nm or more, 650 nm or more, 700 nm or more, 750 nm or more, 800 nm or more, 850 nm or more, 900 nm or more, 950 nm or more, 1 μm or more, 2 μm or more, 3 μm or more, 4 μm or more, 5 μm or more, 6 μm or more, 7 μm or more, 8 μm or more, 9 μm or more, 10 μm or more, 15 μm or more, 20 μm or more, 25 μm or more, 30 μm or more, 35 μm or more, or 40 μm or more). In some examples, the bubble can have a diameter of 50 micrometers (μm, microns) or less (e.g., 45 μm or less, 40 μm or less, 35 μm or less, 30 μm or less, 25 μm or less, 20 μm or less, 15 μm or less, 10 μm or less, 9 μm or less, 8 μm or less, 7 μm or less, 6 μm or less, 5 μm or less, 4 μm or less, 3 μm or less, 2 μm or less, 1 μm or less, 950 nm or less, 900 nm or less, 850 nm or less, 800 nm or less, 750 nm or less, 700 nm or less, 650 nm or less, 600 nm or less, or 550 nm or less). The diameter of the bubble can range from any of the minimum values described above to any of the maximum values described above. For example, the bubble can have a diameter of from 500 nm to 50 μm (e.g., from 500 nm to 10 μm, from 10 μm to 50 μm, from 500 nm to 1 μm, from 1 μm to 10 μm, from 10 μm to 25 μm, from 25 μm to 50 μm, from 500 nm to 25 μm, from 750 nm to 50 μm, or from 750 nm to 25 μm).

The methods further comprise trapping at least a portion of the plurality of chiral analytes at the gas-liquid interface of the bubble and the liquid sample, said portion of the plurality of chiral analytes trapped at the gas-liquid interface being a trapped portion of the plurality of chiral analytes. In some examples, the trapped portion of the plurality of chiral analytes are not damaged during the trapping. The trapped portion of the plurality of chiral analytes can, for example, be trapped by convection (e.g., natural convection and/or Marangoni convection).

The methods further comprise depositing at least a portion of the trapped portion of the plurality of chiral analytes on the chiral plasmonic substrate proximate to the gas-solid interface of the bubble and the chiral plasmonic substrate, said portion of the trapped portion of the plurality of chiral analytes deposited on the chiral plasmonic substrate being a deposited portion of the plurality of chiral analytes. In some examples, the deposited portion of the plurality of chiral analytes are not damaged during the deposition. The bubble can, for example, be used to overcome the diffusion limit and concentrate at least a portion of the plurality of chiral analytes at or near the chiral plasmonic substrate.

The deposited portion of the plurality of chiral analytes can, for example, be deposited in an amount of time of 500 milliseconds or more (e.g., 600 milliseconds or more, 700 milliseconds or more, 800 milliseconds or more, 900 milliseconds or more, 1 second or more, 1.5 seconds or more, 2 seconds or more, 2.5 seconds or more, 3 seconds or more, 3.5 seconds or more, 4 seconds or more, 4.5 seconds or more, 5 seconds or more, 6 seconds or more, 7 seconds or more, 8 seconds or more, 9 seconds or more, 10 seconds or more, 15 seconds or more, 20 seconds or more, 25 seconds or more, 30 seconds or more, 35 seconds or more, 40 seconds or more, 45 seconds or more, 50 seconds or more, 55 seconds or more, 1 minute or more, 2 minutes or more, 3 minutes or more, 4 minutes or more, 5 minutes or more, 10 minutes or more, 15 minutes or more, 20 minutes or more, 25 minutes or more, 30 minutes or more, 35 minutes or more, 40 minutes or more, 45 minutes or more, 50 minutes or more, 55 minutes or more, 1 hour or more, 2 hours or more, 3 hours or more, 4 hours or more, 5 hours or more, 6 hours or more, 7 hours or more, 8 hours or more, 9 hours or more, or 10 hours or more). In some examples, the deposited portion of the plurality of chiral analytes can be deposited in an amount of time of 12 hours or less (e.g., 11 hours or less, 10 hours or less, 9 hours or less, 8 hours or less, 7 hours or less, 6 hours or less, 5 hours or less, 4 hours or less, 3 hours or less, 2 hours or less, 1 hour or less, 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less, 4 minutes or less, 3 minutes or less, 2 minutes or less, 1 minute or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 9 seconds or less, 8 seconds or less, 7 seconds or less, 6 seconds or less, 5 seconds or less, 4.5 seconds or less, 4 seconds or less, 3.5 seconds or less, 3 seconds or less, 2.5 seconds or less, 2 seconds or less, 1.5 seconds or less, 1 second or less, 900 milliseconds or less, 800 milliseconds or less, or 700 milliseconds or less). The amount of time in which the deposited portion of the plurality of chiral analytes are deposited can range from any of the minimum values described above to any of the maximum values described above. For example, the deposited portion of the plurality of chiral analytes can be deposited in an amount of time of from 500 milliseconds to 12 hours (e.g., from 500 milliseconds to 1 minute, from 1 minute to 12 hours, from 500 milliseconds to 1 hour, from 500 milliseconds to 10 minutes, from 500 milliseconds to 1 minute, or from 500 milliseconds to 10 seconds).

In some examples, the deposited portion of the plurality of chiral analytes are immobilized on the chiral plasmonic substrate by surface adhesion, convection forces (e.g., Marangoni convection forces), or a combination thereof. In some examples, the chiral plasmonic substrate further comprises a ligand and the deposited portion of the plurality of chiral analytes are immobilized on the chiral plasmonic substrate by electrostatic attraction and/or chemical recognition with the ligand.

The methods further comprise illuminating at least a portion of the deposited portion of the plurality of chiral analytes and at least the portion of the chiral plasmonic substrate at which the deposited portion of the plurality of chiral analytes is located with circularly polarized electromagnetic radiation, said portion of the deposited portion of the plurality of chiral analytes illuminated with the circularly polarized electromagnetic radiation being an illuminated portion of the deposited portion of the plurality of chiral analytes and said portion of the chiral plasmonic substrate at which the deposited portion of the plurality of chiral analytes is located illuminated with the circularly polarized electromagnetic radiation being an illuminated portion of the chiral plasmonic substrate; capturing an electromagnetic signal from: the illuminated portion of the deposited portion of the plurality of chiral analytes, the illuminated portion of the chiral plasmonic substrate, or a combination thereof, wherein the circularly polarized electromagnetic radiation passes through both the illuminated portion of the deposited portion of the plurality of chiral analytes and the illuminated portion of the chiral plasmonic substrate before being captured; and processing the electromagnetic signal to determine a property of the liquid sample.

Circularly polarized light occurs when the direction of the electric field vector rotates about its propagation direction while the vector retains a constant magnitude. At a single point in space, the circularly polarized-vector will trace out a circle over one period of the wave frequency. For left circularly polarized light (LCP), with propagation towards the observer, the electric vector rotates counterclockwise. For right circularly polarized light (RCP), the electric vector rotates clockwise.

When circularly polarized light passes through an absorbing optically active medium, the speeds between right and left polarizations differ, as well as their wavelength, and the extent to which they are absorbed. As circularly polarized light is chiral, it interacts differently with chiral materials. That is, the two types of circularly polarized light are absorbed to different extents by a chiral material. In a circular dichroism experiment, equal amounts of left and right circularly polarized light of a selected wavelength (or range of wavelengths) are alternately radiated into a (chiral) sample. One of the two polarizations is absorbed more than the other one and this wavelength-dependent difference of absorption is measured yielding the circular dichroism spectrum of the sample.

In some examples, the circularly polarized electromagnetic radiation can comprise circularly polarized light at one or more wavelength from 400 nm to 2000 nm. In some examples, the circularly polarized electromagnetic radiation can comprise right circularly polarized light, left circularly polarized light, or a combination thereof.

The circularly polarized electromagnetic radiation can, for example, be provided by a light source. In some examples, the methods can further comprise using a polarizer to circularly polarize the electromagnetic radiation from a light source before illuminating the chiral plasmonic substrate and/or the liquid sample. The polarizer can, for example, comprise a circular polarizer, a series of linear polarizers, a quarter wave plate and a linear polarizer, or a combination thereof.

In some examples, the methods further comprise removing the illumination from the first location and allowing the bubble to collapse before illuminating with the circularly polarized light.

The property of the liquid sample can, for example, comprise the chirality of the illuminated portion of the deposited portion of the plurality of chiral analytes, the presence of the plurality of chiral analytes, the circular dichroism of the liquid sample, the concentration of the plurality of chiral analytes in the liquid sample, or a combination thereof.

In some examples, the methods further comprise diagnosing and/or monitoring a disease in a subject based on the property of the liquid sample. Examples of diseases include, but are not limited to neurodegenerative diseases, infectious diseases (e.g., infection with a pathogen such as a virus, bacteria, fungi, protozoa, or parasite), rheumatologic diseases, genetic diseases, acute and chronic respiratory diseases, gastrointestinal diseases, liver diseases, dermatologic diseases, and combinations thereof. Specific examples of diseases include, but are not limited to, diabetes, kidney disease, short bowel syndrome, Alzheimer's disease, Parkinson's disease, cardiovascular disease, chronic respiratory disease, cancer, and combinations thereof. In some examples, the disease can comprise diabetes, a kidney disease, cancer, or a combination thereof. In some examples, the methods can further comprise selecting a course of therapy or treatment for the subject based on the property of the liquid sample.

The time elapsed from illuminating the first location of the chiral plasmonic substrate to determining the property of the liquid sample can, for example, be 500 milliseconds or more (e.g., 600 milliseconds or more, 700 milliseconds or more, 800 milliseconds or more, 900 milliseconds or more, 1 second or more, 1.5 seconds or more, 2 seconds or more, 2.5 seconds or more, 3 seconds or more, 3.5 seconds or more, 4 seconds or more, 4.5 seconds or more, 5 seconds or more, 6 seconds or more, 7 seconds or more, 8 seconds or more, 9 seconds or more, seconds or more, 15 seconds or more, 20 seconds or more, 25 seconds or more, 30 seconds or more, 35 seconds or more, 40 seconds or more, 45 seconds or more, 50 seconds or more, 55 seconds or more, 1 minute or more, 2 minutes or more, 3 minutes or more, 4 minutes or more, 5 minutes or more, 10 minutes or more, 15 minutes or more, 20 minutes or more, 25 minutes or more, 30 minutes or more, 35 minutes or more, 40 minutes or more, 45 minutes or more, 50 minutes or more, 55 minutes or more, 1 hour or more, 2 hours or more, 3 hours or more, 4 hours or more, 5 hours or more, 6 hours or more, 7 hours or more, 8 hours or more, 9 hours or more, or 10 hours or more). In some examples, the time elapsed from illuminating the first location of the chiral plasmonic substrate to determining the property of the liquid sample can be 12 hours or less (e.g., 11 hours or less, 10 hours or less, 9 hours or less, 8 hours or less, 7 hours or less, 6 hours or less, 5 hours or less, 4 hours or less, 3 hours or less, 2 hours or less, 1 hour or less, 55 minutes or less, 50 minutes or less, 45 minutes or less, 40 minutes or less, 35 minutes or less, 30 minutes or less, 25 minutes or less, 20 minutes or less, 15 minutes or less, 10 minutes or less, 5 minutes or less, 4 minutes or less, 3 minutes or less, 2 minutes or less, 1 minute or less, 55 seconds or less, 50 seconds or less, 45 seconds or less, 40 seconds or less, 35 seconds or less, 30 seconds or less, 25 seconds or less, 20 seconds or less, 15 seconds or less, 10 seconds or less, 9 seconds or less, 8 seconds or less, 7 seconds or less, 6 seconds or less, 5 seconds or less, 4.5 seconds or less, 4 seconds or less, 3.5 seconds or less, 3 seconds or less, 2.5 seconds or less, 2 seconds or less, 1.5 seconds or less, 1 second or less, 900 milliseconds or less, 800 milliseconds or less, or 700 milliseconds or less). The amount of time elapsed from illuminating the first location of the chiral plasmonic substrate to determining the property of the liquid sample can range from any of the minimum values described above to any of the maximum values described above. For example, the time elapsed from illuminating the first location of the chiral plasmonic substrate to determining the property of the liquid sample can be from 500 milliseconds to 12 hours (e.g., from 500 milliseconds to 1 minute, from 1 minute to 12 hours, from 500 milliseconds to 1 hour, from 500 milliseconds to 10 minutes, from 500 milliseconds to 5 minutes, from 500 milliseconds to 1 minute, or from 500 milliseconds to 10 seconds). In some examples, the time elapsed from illuminating the first location of the chiral plasmonic substrate to determining the property of the liquid sample can be 10 minutes or less, 5 minutes or less, or 1 minute or less. In some examples, the time elapsed is from 0.5 seconds to 1 minute.

In some examples, the methods further comprise illuminating a second location of the chiral plasmonic substrate thereby: generating a second bubble at a location in the liquid sample proximate to the second location of the chiral plasmonic substrate, the second bubble having a gas-liquid interface with the liquid sample and a gas-solid interface with the chiral plasmonic substrate; trapping at least a second portion of the plurality of chiral analytes at the gas-liquid interface of the second bubble and the liquid sample, said second portion of the plurality of chiral analytes trapped at the gas-liquid interface being a second trapped portion of the plurality of chiral analytes; and depositing at least a portion of the second trapped portion of the plurality of chiral analytes on the chiral plasmonic substrate proximate to the gas-solid interface of the second bubble and the chiral plasmonic substrate, said portion of the second trapped portion of the plurality of chiral analytes deposited on the chiral plasmonic substrate being a second deposited portion of the plurality of chiral analytes. As used herein, "a second location" and "the second location" are meant to include any number of locations in any arrangement on the chiral plasmonic substrate. Thus, for example "a second location" includes one or more second locations. In some embodiments, the second location can comprise a plurality of locations. In some embodiments, the second location can comprise a plurality of locations arranged in an ordered array.

In some examples, the first location and the second location are substantially the same.

In some examples, the first location and the second location are different and the chiral plasmonic substrate is translocated to illuminate the second location. As used herein translocating refers to any type of movement about any axis (e.g., rotation, translation, etc.) In other words, as used herein, translocation refers to a change in position and/or orientation.

In some examples, the first location and the second location are different, the electromagnetic radiation is provided by a light source, and the light source is translocated to illuminate the second location. In some examples, the first location and the second location are different, the electromagnetic radiation is provided by a light source, the light source being configured to illuminate a mirror and the mirror is configured to reflect the electromagnetic radiation from the artificial light source to illuminate the optothermal substrate, and the mirror is translocated to illuminate the second location.

In some examples, the first location and the second location are different and the method further comprises: illuminating at least a portion of the second deposited portion of the plurality of chiral analytes and at least the portion of the chiral plasmonic substrate at which the second deposited portion of the plurality of chiral analytes is located with circularly polarized electromagnetic radiation, said portion of the second deposited portion of the plurality of chiral analytes illuminated with the circularly polarized electromagnetic radiation being an illuminated portion of the second deposited portion of the plurality of chiral analytes and said portion of the chiral plasmonic substrate at which the second deposited portion of the plurality of chiral analytes is located illuminated with the circularly polarized electromagnetic radiation being a second illuminated portion of the chiral plasmonic substrate; capturing an electromagnetic signal from: the illuminated portion of the second deposited portion of the plurality of chiral analytes, the second illuminated portion of the chiral plasmonic substrate, or a combination thereof, wherein the circularly polarized electromagnetic radiation passes through both the illuminated portion of the second deposited portion of the plurality of chiral analytes and the second illuminated portion of the chiral plasmonic substrate before being captured; and processing the electromagnetic signal to determine a second property of the liquid sample.

Devices

Also disclosed herein are devices comprising any of the chiral plasmonic substrates described herein, such as those described above and shown in FIG. 1-FIG. 8.

For example, also disclosed herein are devices comprising a chiral plasmonic substrate, wherein when the device is assembled together with a first light source, a liquid sample comprising a plurality of chiral analytes, a second light source, and an instrument: the liquid sample is configured to be in thermal contact with the chiral plasmonic substrate; the first light source is configured to illuminate a first location of the chiral plasmonic substrate with electromagnetic radiation; wherein electromagnetic radiation comprises a wavelength that overlaps with at least a portion of the plasmon resonance energy of the chiral plasmonic substrate such that the chiral plasmonic substrate converts at least a portion of the electromagnetic radiation into thermal energy; thereby: generating a bubble at a location in the liquid sample proximate to the first location of the chiral plasmonic substrate via plasmon-enhanced photothermal effects, the bubble having a gas-liquid interface with the liquid sample and a gas-solid interface with the chiral plasmonic substrate; trapping at least a portion of the plurality of chiral analytes at the gas-liquid interface of the bubble and the liquid sample, said portion of the plurality of chiral analytes trapped at the gas-liquid interface being a trapped portion of the plurality of chiral analytes; and depositing at least a portion of the trapped portion of the plurality of chiral analytes on the chiral plasmonic substrate proximate to the gas-solid interface of the bubble and the chiral plasmonic substrate, said portion of the trapped portion of the plurality of chiral analytes deposited on the chiral plasmonic substrate being a deposited portion of the plurality of chiral analytes; and the second light source is configured to illuminate at least a portion of the deposited portion of the plurality of chiral analytes and at least the portion of the chiral plasmonic substrate at which the deposited portion of the plurality of chiral analytes is located with circularly polarized electromagnetic radiation, said portion of the deposited portion of the plurality of chiral analytes illuminated with the circularly polarized electromagnetic radiation being an illuminated portion of the deposited portion of the plurality of chiral analytes and said portion of the chiral plasmonic substrate at which the deposited portion of the plurality of chiral analytes is located illuminated with the circularly polarized electromagnetic radiation being an illuminated portion of the chiral plasmonic substrate; the instrument is configured to capture an electromagnetic signal from: the illuminated portion of the deposited portion of the plurality of chiral analytes, the illuminated portion of the chiral plasmonic substrate, or a combination thereof, wherein the circularly polarized electromagnetic radiation passes through both the illuminated portion of the deposited portion of the plurality of chiral analytes and the illuminated portion of the chiral plasmonic substrate before being captured; and the instrument is further configured to process the electromagnetic signal to determine a property of the liquid sample.

Systems

Also disclosed herein are systems for performing the methods described herein.

Figure 9:
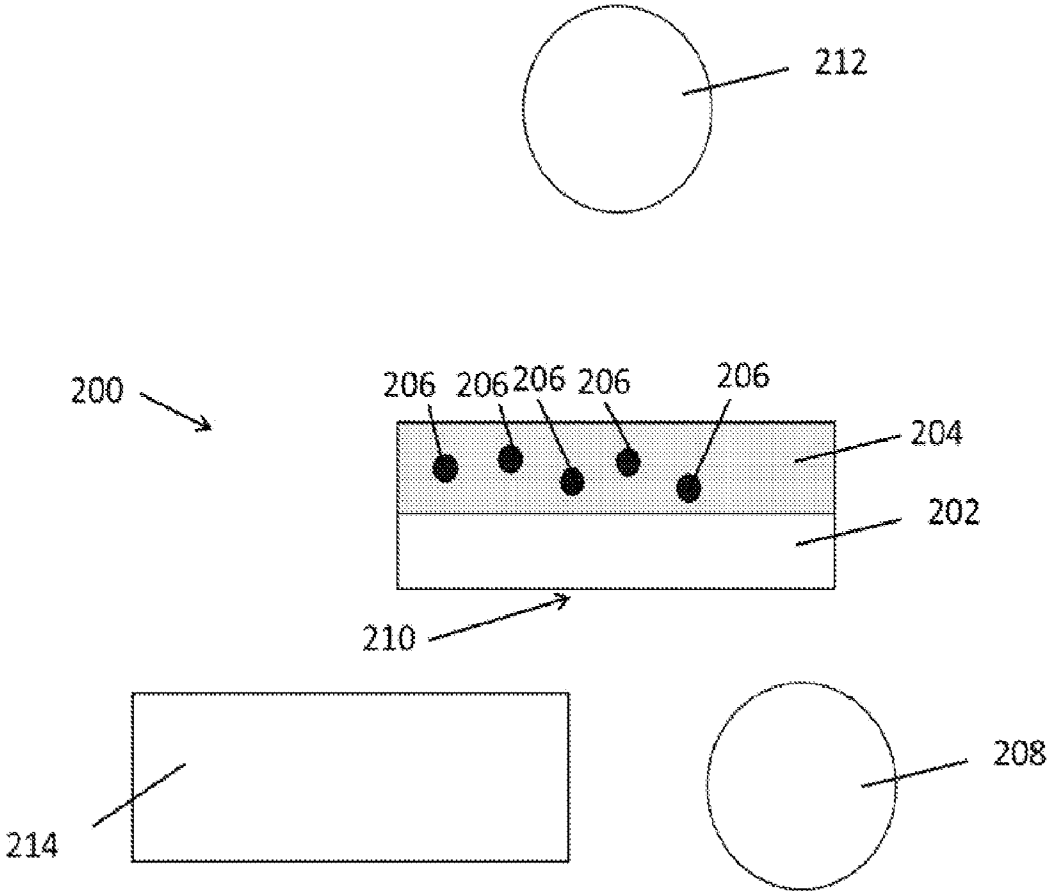
FIG. 9 is a schematic of an example system as disclosed herein.

Referring now to FIG. 9, the systems 200 can comprise any of the devices comprising any of the chiral plasmonic substrates 202 described herein, such as the chiral plasmonic substrates 102 shown in FIG. 1-FIG. 8. The systems 200 further comprise a liquid sample 204 comprising a plurality of chiral analytes 206, the liquid sample 204 being in thermal contact with the chiral plasmonic substrate 202; and a first light source 208 configured to illuminate a first location 210 of the chiral plasmonic substrate 202 with electromagnetic radiation.

The electromagnetic radiation can comprise a wavelength that overlaps with at least a portion of the plasmon resonance energy of the chiral plasmonic substrate 202 such that the chiral plasmonic substrate 202 converts at least a portion of the electromagnetic radiation into thermal energy, thereby: generating a bubble at a location in the liquid sample 204 proximate to the first location 210 of the chiral plasmonic substrate 202 via plasmon-enhanced photothermal effects, the bubble having a gas-liquid interface with the liquid sample 204 and a gas-solid interface with the chiral plasmonic substrate 202; trapping at least a portion of the plurality of chiral analytes at the gas-liquid interface of the bubble and the liquid sample 204, said portion of the plurality of chiral analytes trapped at the gas-liquid interface being a trapped portion of the plurality of chiral analytes; and depositing at least a portion of the trapped portion of the plurality of chiral analytes on the chiral plasmonic substrate 202 proximate to the gas-solid interface of the bubble and the chiral plasmonic substrate 202, said portion of the trapped portion of the plurality of chiral analytes deposited on the chiral plasmonic substrate 202 being a deposited portion of the plurality of chiral analytes.

The systems 200 further comprise a second light source 212 configured to illuminate at least a portion of the deposited portion of the plurality of chiral analytes and at least the portion of the chiral plasmonic substrate 202 at which the deposited portion of the plurality of chiral analytes is located with circularly polarized electromagnetic radiation, said portion of the deposited portion of the plurality of chiral analytes illuminated with the circularly polarized electromagnetic radiation being an illuminated portion of the deposited portion of the plurality of chiral analytes and said portion of the chiral plasmonic substrate 202 at which the deposited portion of the plurality of chiral analytes is located illuminated with the circularly polarized electromagnetic radiation being an illuminated portion of the chiral plasmonic substrate 202.

The first light source 208 and/or the second light source 212 can, for example, comprise(s) an artificial light source. In some examples, the first light source 208 comprises a laser. In some examples, the second light source 212 comprises a halogen lamp.

In some examples, the systems 200 can further comprise a means for translocating the chiral plasmonic substrate 202 and/or the first light source 208.

The systems 200 further comprise an instrument 214 configured to capture an electromagnetic signal from: the illuminated portion of the deposited portion of the plurality of chiral analytes, the illuminated portion of the chiral plasmonic substrate 202, or a combination thereof, wherein the circularly polarized electromagnetic radiation passes through both the illuminated portion of the deposited portion of the plurality of chiral analytes and the illuminated portion of the chiral plasmonic substrate 202 before being captured; and the instrument 214 being further configured to process the electromagnetic signal to determine a property of the liquid sample 204. The instrument 214 can, for example, comprise a spectrometer. Examples of spectrometers include, but are not limited to, Raman spectrometers, UV-vis absorption spectrometers, IR absorption spectrometers, fluorescence spectrometers, phase contrast spectrometers, and combinations thereof.

Figure 10:
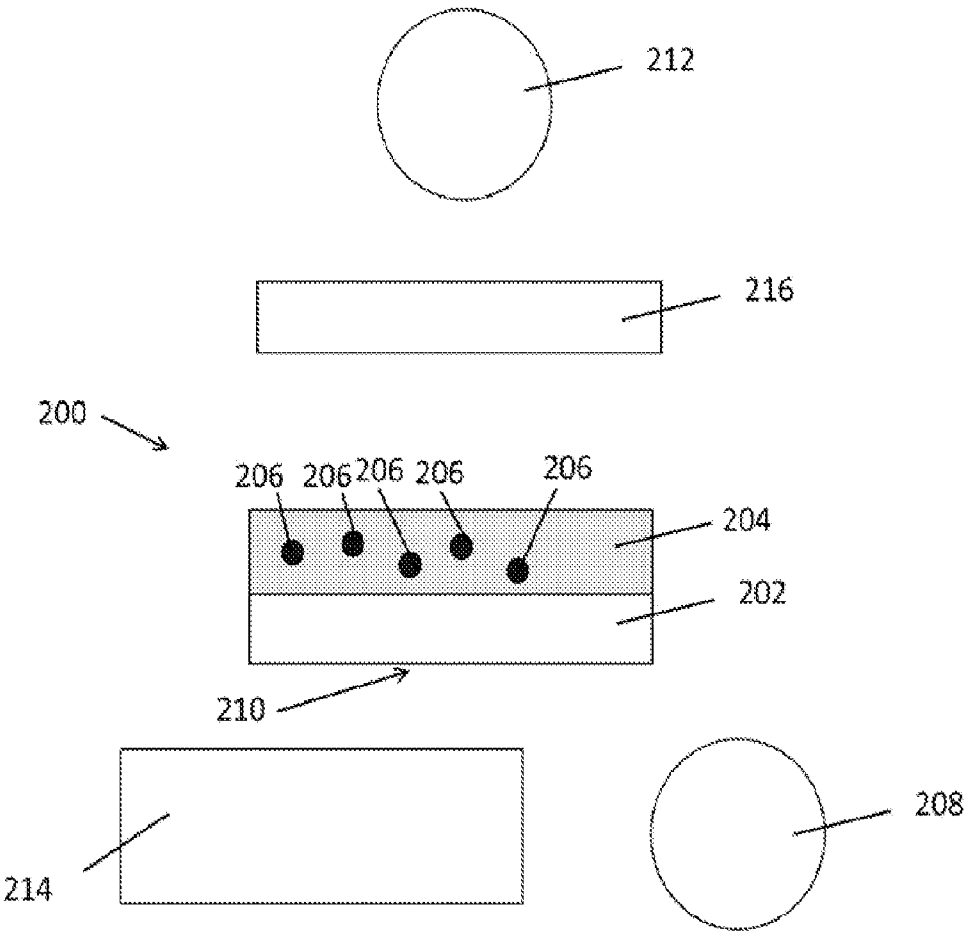
FIG. 10 is a schematic of an example system as disclosed herein.

Referring now to FIG. 10, the systems 200 can, in some examples, further comprise a polarizer 216 configured to circularly polarize the light from the second light source 212 before illuminating the chiral plasmonic substrate 202 and/or the liquid sample 204. The polarizer 216 can, for example, comprise a circular polarizer, a series of linear polarizers, a quarter wave plate and a linear polarizer, or a combination thereof.

Figure 11:
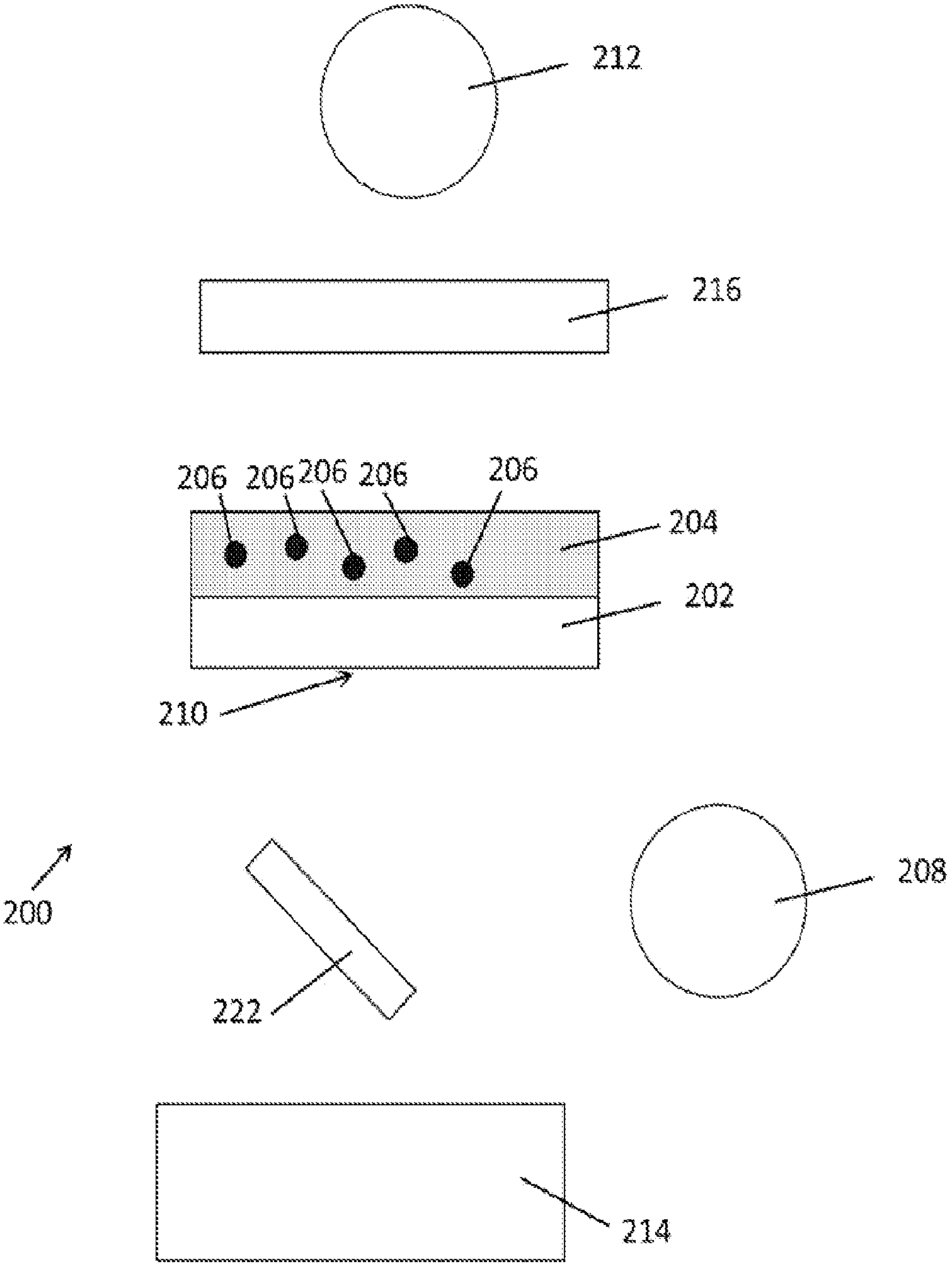
FIG. 11 is a schematic of an example system as disclosed herein.

Referring now to FIG. 11, the systems 200 can, in some examples, further comprise a mirror, a beam splitter, or a combination thereof 222, wherein the first light source 208 is configured to illuminate the mirror and/or beam splitter 222, and the mirror and/or beam splitter 222 is/are configured to reflect and/or redirect the electromagnetic radiation from the light source to illuminate the first location 210 of the chiral plasmonic substrate 202. In some examples, the systems 200 can further comprise a mirror and the mirror can comprise a plurality of mirrors (e.g., a digital micromirror device). In some examples, the systems 200 can further comprising a means for translocating the mirror and/or the beam splitter 222.

In some examples, the systems 200 can further comprise a lens (e.g., one or more lenses). The lens can be any type of lens, such as a simple lens, a compound lens, a spherical lens, a toric lens, a biconvex lens, a plano-convex lens, a plano-concave lens, a negative meniscus lens, a positive meniscus lens, a biconcave lens, a converging lens, a diverging lens, a cylindrical lens, a Fresnel lens, a lenticular lens, or a gradient index lens.

Figure 12:
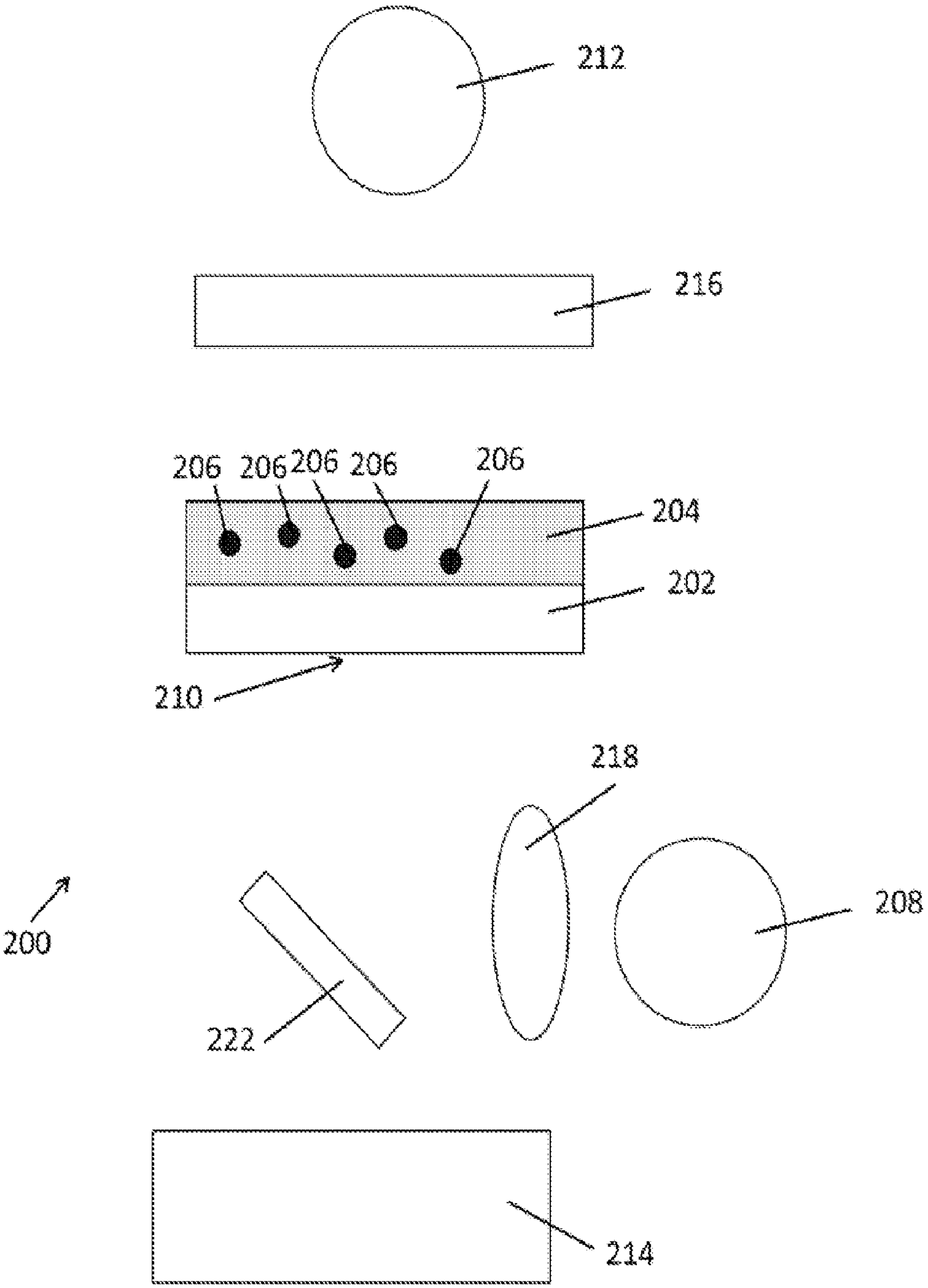
FIG. 12 is a schematic of an example system as disclosed herein.

Referring now to FIG. 12, in some examples the systems 200 can further comprise a first lens comprising a beam expander 218 configured to expand the illumination from the first light source 208 before illuminating the first location 210 of the chiral plasmonic substrate 202 and/or before illuminating the mirror and/or beam splitter 222.

Figure 13:
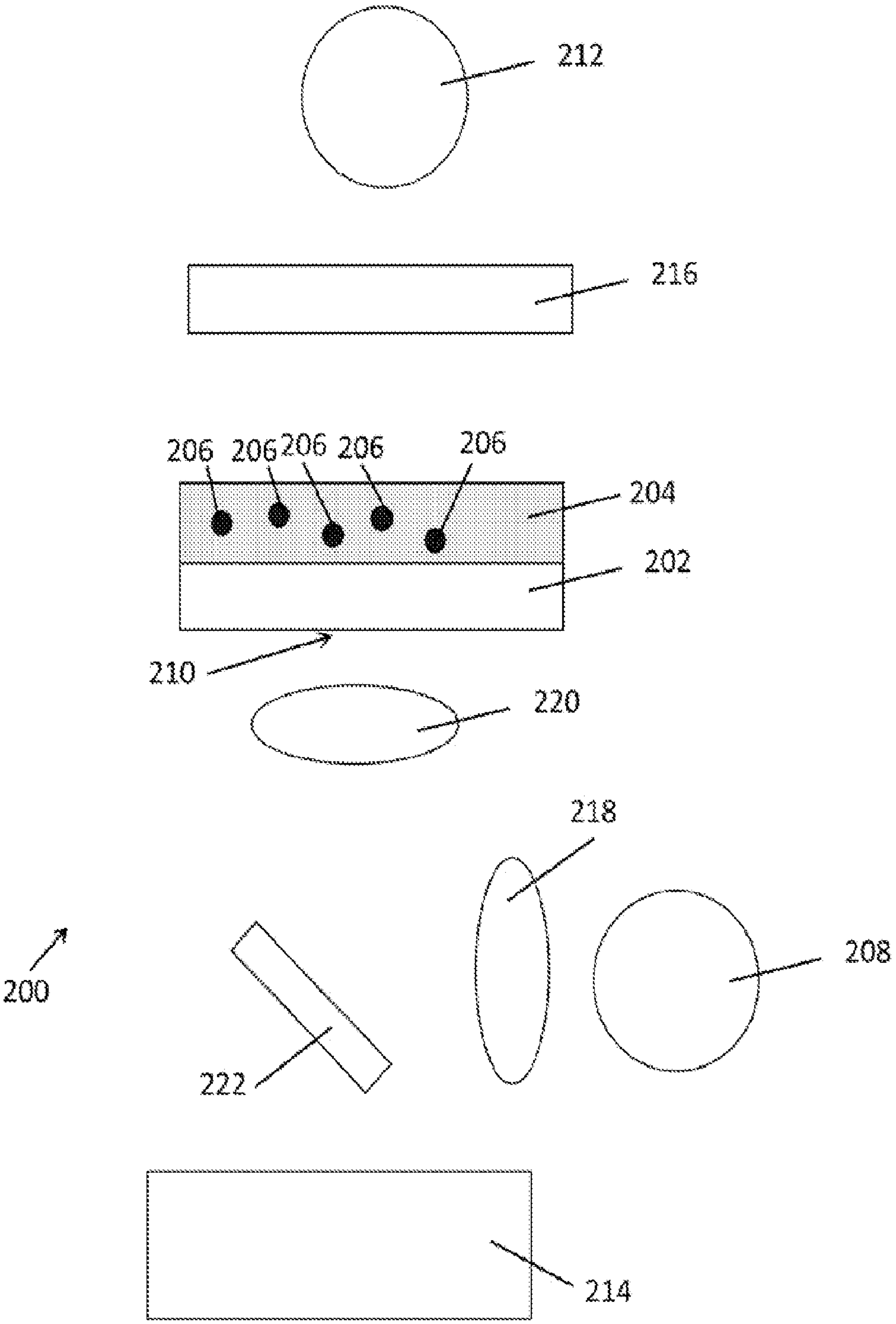
FIG. 13 is a schematic of an example system as disclosed herein.

Referring now to FIG. 13, in some examples, the systems 200 can further comprise a second lens comprising a microscope objective 220 configured to focus the electromagnetic radiation from the first light source 208 to the first location 110 and/or to focus the electromagnetic signal to the instrument 214.

Figure 14:
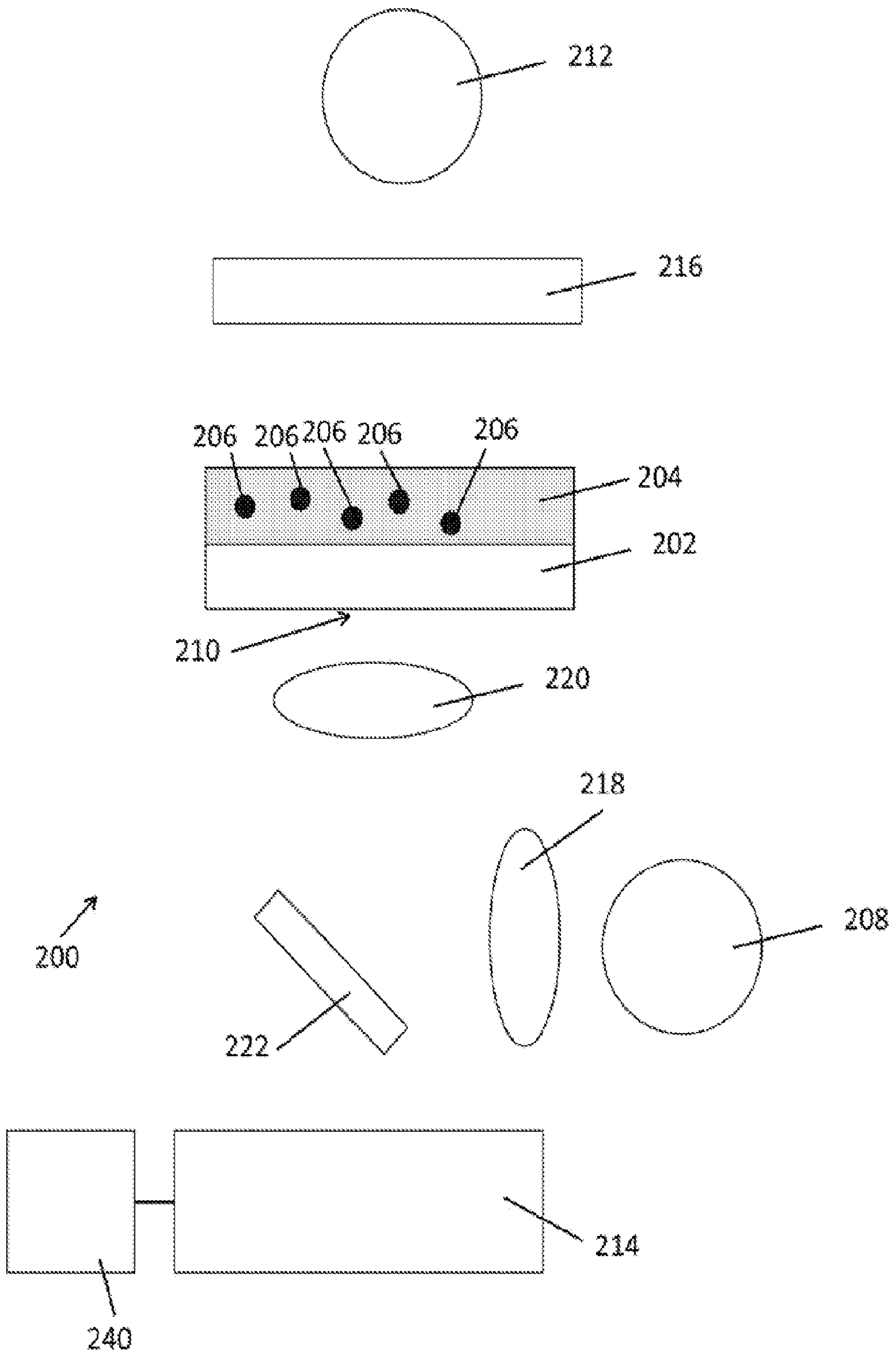
FIG. 14 is a schematic of an example system as disclosed herein.

In some examples, the systems 200 can further comprise a computing device 240 configured to receive and process the electromagnetic signal from the instrument 214, such as shown in FIG. 14.

Figure 15:
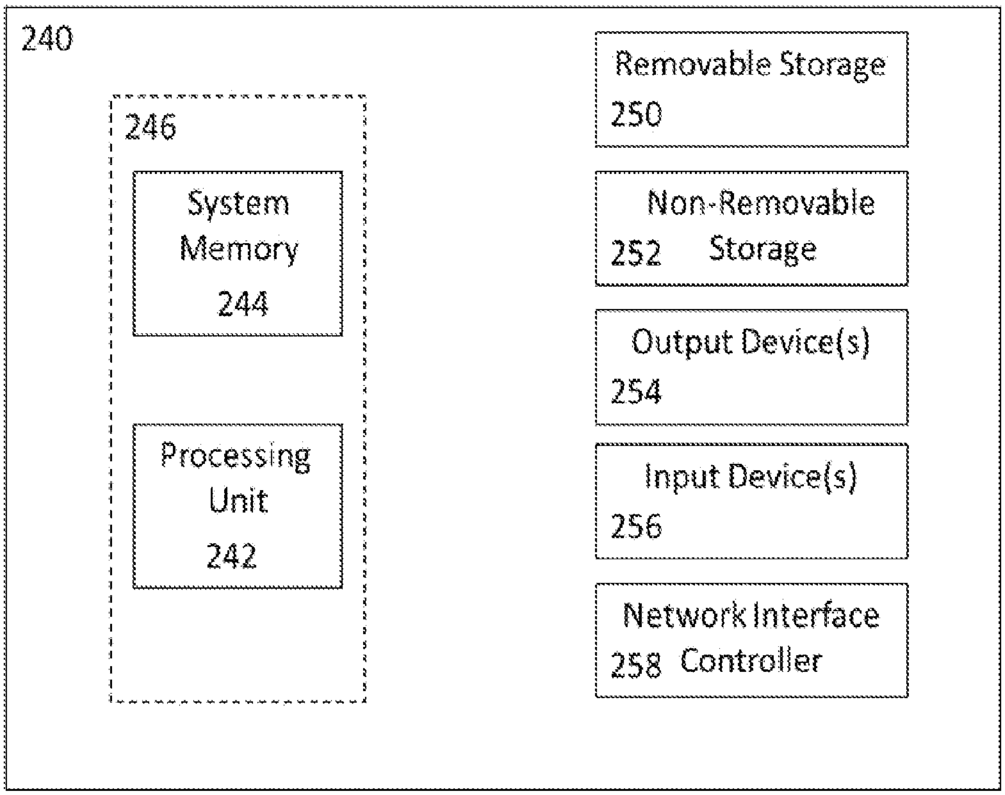
FIG. 15 is a schematic of an example computing device.

FIG. 15 illustrates an example computing device 240 upon which examples disclosed herein may be implemented. The computing device 240 can include a bus or other communication mechanism for communicating information among various components of the computing device 240. In its most basic configuration, computing device 240 typically includes at least one processing unit 242 (a processor) and system memory 244. Depending on the exact configuration and type of computing device, system memory 244 may be volatile (such as random access memory (RAM)), non-volatile (such as read-only memory (ROM), flash memory, etc.), or some combination of the two. This most basic configuration is illustrated in FIG. 15 by a dashed line 246. The processing unit 242 may be a standard programmable processor that performs arithmetic and logic operations necessary for operation of the computing device 240.

The computing device 240 can have additional features/functionality. For example, computing device 240 may include additional storage such as removable storage 250 and non-removable storage 252 including, but not limited to, magnetic or optical disks or tapes. The computing device 240 can also contain network connection(s) 258 that allow the device to communicate with other devices. The computing device 240 can also have input device(s) 256 such as a keyboard, mouse, touch screen, antenna or other systems configured to communicate with the camera in the system described above, etc. Output device(s) 254 such as a display, speakers, printer, etc. may also be included. The additional devices can be connected to the bus in order to facilitate communication of data among the components of the computing device 240.

The processing unit 242 can be configured to execute program code encoded in tangible, computer-readable media. Computer-readable media refers to any media that is capable of providing data that causes the computing device 240 (i.e., a machine) to operate in a particular fashion. Various computer-readable media can be utilized to provide instructions to the processing unit 242 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 242 can execute program code stored in the system memory 244. For example, the bus can carry data to the system memory 244, from which the processing unit 242 receives and executes instructions. The data received by the system memory 244 can optionally be stored on the removable storage 250 or the non-removable storage 252 before or after execution by the processing unit 242.

The computing device 240 typically includes a variety of computer-readable media. Computer-readable media can be any available media that can be accessed by device 240 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 244, removable storage 250, and non-removable storage 252 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 240. Any such computer storage media can be part of computing device 240.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, the system 200 comprises a computing device 240 comprising a processor 242 and a memory 244 operably coupled to the processor 242, the memory 244 having further computer-executable instructions stored thereon that, when executed by the processor 242, cause the processor 242 to: receive the electromagnetic signal captured by the instrument 214; process the electromagnetic signal to determine the property of the liquid sample 204; and output the property of the liquid sample 204.

The analysis of signals captured by the instrument can be carried out in whole or in part on one or more computing device. For example, the system may comprise one or more additional computing device.

The instrument can comprise, for example, a spectrometer. Examples of spectrometers include, but are not limited to, Raman spectrometers, UV-vis absorption spectrometers, IR absorption spectrometers, fluorescence spectrometers, phase contrast spectrometers, and combinations thereof.

In some examples, the electromagnetic signal received by the processor from the instrument can comprise a spectrum (e.g., Raman, UV-vis, IR, fluorescence, phase contrast). The property of the liquid sample can, for example, comprise the chirality of the illuminated portion of the deposited portion of the plurality of chiral analytes, the presence of the plurality of chiral analytes, the circular dichroism of the liquid sample, the concentration of the plurality of chiral analytes in the liquid sample, or a combination thereof.

Methods of Use

Also disclosed herein are methods of use of the devices and/or systems described herein.

The systems, methods, and devices described herein are sensitive (e.g., detecting low concentrations of the plurality of chiral analytes), efficient (e.g., use low liquid sample volumes), rapid (e.g., completion of analysis in minutes), accurate, and flexible (e.g., a variety of liquid samples such as a variety of bodily fluids can be used). As such, the systems, methods, and devices described herein are well suited for use in numerous sensing applications and/or in point-of-care (POC) applications.

For example, also described herein are methods of use of any of the devices described herein or any of the systems described herein as a chiral sensor. For example, the systems, devices, and methods described herein can be used in clinical and healthcare settings to detect and/or quantify biomarkers or metabolites to identify risk for, diagnosis of, or progression of a pathological or physiological process in a subject. Examples of biomarkers include proteins, peptides, polypeptides, hormones, prohormones, lipids, glycoproteins, carbohydrates, DNA, RNA, and combinations thereof.

Also described herein are methods of use of any of the devices described herein or any of the systems described herein to diagnose and/or monitor a disease in a subject by determining the property of the liquid sample. The property of the liquid sample can, for example, comprise the chirality of the illuminated portion of the deposited portion of the plurality of chiral analytes, the presence of the plurality of chiral analytes, the circular dichroism of the liquid sample, the concentration of the plurality of chiral analytes in the liquid sample, or a combination thereof. In some examples, the plurality of chiral analytes can be, for example, a biomarker (i.e., a molecular indicator associated with a particular pathological or physiological state) present in the bodily fluid (e.g., the liquid sample) that can be assayed to identify risk for, diagnosis of, or progression of a pathological or physiological process in a subject. Examples of diseases include, but are not limited to neurodegenerative diseases, infectious diseases (e.g., infection with a pathogen such as a virus, bacteria, fungi, protozoa, or parasite), rheumatologic diseases, genetic diseases, acute and chronic respiratory diseases, gastrointestinal diseases, liver diseases, dermatologic diseases, and combinations thereof. In some examples, the disease can comprise diabetes, a kidney disease, short bowel syndrome, Alzheimer's disease, cardiovascular disease, chronic respiratory disease, cancer, or a combination thereof. In some examples, the disease can comprise diabetes, a kidney disease, cancer, or a combination thereof. In some examples, the methods can further comprise selecting a course of therapy for the subject based on the property of the liquid sample.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1—Detecting Diabetes-Induced Abnormal Chirality of Metabolites in Urine via Accumulation-Assisted Plasmonic Chiral Sensing Abstract. Chiral molecules in human bodies feature homochirality that is crucial for proper biochemical processes. Abnormal amounts of chiral metabolic molecules in biofluids has been found in patients with diabetes, which presently affects more than 400 million people worldwide. However, the detailed analysis of diabetes-related abnormal chirality in biofluids and its potential use for clinical applications have been hindered by the difficulty in detecting and monitoring the chiral changes in biofluids, due to their low molar mass and trace concentrations. Herein, the label-free chiral detection of metabolic molecules at picomolar level using only 10 μL of clinical samples is demonstrated. The ultra-high sensitivity and low sample consumption is enabled by microbubble-induced rapid accumulation of biomolecules on plasmonic chiral sensors. This technique was applied to urine samples from mice and human, uncovering the typically undetectable diabetes-induced abnormal dextrorotatory shift in chirality of urine metabolites. Furthermore, the accumulation-assisted plasmonic chiral sensing achieved a diagnostic accuracy of 84% on clinical urine samples from human patients. With the ultra-high sensitivity, ultra-low sample consumption and fast response, this technique can benefit diabetes research and can be developed as point-of-care devices for first-line noninvasive screening and prognosis of pre-diabetes or diabetes and its complications.

Main. As building blocks of life, chiral molecules in human bodies are usually dominated by one of the enantiomers, showing homochirality that is essential for proper biochemical reactions such as protein folding (Cahn et al. *Angewandte Chemie International Edition in English* 1966, 5, 385-415). Abnormal concentration of chiral molecules has been observed in human bodies with increasing age (Yekkala et al. *Forensic science international* 2006, 159, S89-S94; Helfman et al. *Nature* 1976, 262, 279-281) and various chronic diseases (McCudden et al. *Clinical biochemistry* 2006, 39, 1112-1130), indicating the potential of applying chiral biomarkers as health indicators for diagnostic and prognostic applications (Kalíková et al. *Separations* 2016, 3, 30; Kimura et al. *Scientific reports* 2016, 6, 26137). In particular, elevated levels of many D-type metabolic molecules in urine have shown strong correlation with diabetic mellitus. For example, urine is found to have increased level of glucose, which is predominantly D-type in the human body, due to diabetes-induced glycosuria (Murray et al. *Harper's illustrated biochemistry*; Mcgraw-hill, 2014). Recent study also found that diabetics have elevated urinary D-lactate as compared to controls (Talasniemi et al. *Clinical biochemistry* 2008, 41, 1099-1103). The discovery of such correlations between diabetes and elevated levels of chiral metabolic molecules indicates that monitoring the chirality of urine metabolites for abnormal changes can offer a promising route towards noninvasive diabetes diagnosis.

However, the diabetes-induced change in chirality of urine metabolites has not been fully explored, hindering clinical development of the chirality-based disease diagnosis and monitoring. In particular, establishment of an accurate relationship between diabetes and chirality of metabolites in urine is crucial to improving the knowledge on the pathological roles of chiral disorder, which will facilitate the new diagnostic device development. However, it remains greatly challenging to rapidly determine the chirality of urine metabolites with high accuracy. Specifically, despite the ultra-high sensitivity of high-performance liquid chromatography, gas chromatography, and capillary electrophoresis coupled to mass spectroscopy for chiral resolution of biomarkers (Kimura et al. *Scientific reports* 2016, 6, 26137; Furusho et al. *Analytical chemistry* 2019, 91, 11569-11575), such separation-based techniques demand molecule-exclusive chiral reagents (Okamoto et al. *Chemical Society Reviews* 2008, 37, 2593-2608). The specific measurements of each chiral molecule reduce capability to investigate the total chiral level and the effects of overall amounts of chiral molecules on the chiral balance in body solutions. Moreover, the bulky mass spectrometer, the slow processing speed, and the demand for highly experienced operators limit the application of mass spectrometer-based techniques at point-of-care settings. Chiroptical techniques such as circular dichroism (CD) spectrometers and polarimeters can overcome the limits of chiral reagents by using polarized lights as label-free and high-throughput chiral selectors. However, conventional chiroptical methods suffer from large sample consumption and low molar sensitivity for metabolic molecules with ultra-small molecular mass and weak light-matter interactions, hindering their applications on detecting the trace chiral metabolites in urine.

Plasmonic chiral metamaterials with strongly enhanced chiral electromagnetic fields, also known as superchiral fields, have recently proven promising in label-free chiral sensing of biomedical molecules with significantly improved sensitivity (Hendry et al. *Nature nanotechnology* 2010, 5, 783; Tang et al. *Science* 2011, 332, 333-336; Valev et al. *Advanced Materials* 2013, 25, 2517-2534; Tullius et al. *J. Am. Chem. Soc.* 2015, 137, 8380-8383). The locally increased twisting of light polarization in superchiral fields can induce intense chiral light-matter interactions, causing asymmetric spectral shifts of the metamaterials upon adsorption of enantiomers, enabling ultra-sensitive molecular chirality sensing (Huang et al. *Biomedical Chromatography* 2013, 27, 1100-1106). Enantioselective discrimination of chiral molecules at picogram level has been demonstrated for molecules with a wide range of molecular weights (Zhao et al. *Nature communications* 2017, 8, 14180; Wu et al. *Advanced Optical Materials* 2017, 5, 1700034). However, plasmon-enhanced chiral sensing requires the analytes to be physically adsorbed on the plasmonic surfaces or residing near the superchiral fields with short (nanometer scale) working distances. Therefore, although such techniques can significantly reduce the requirement on sample consumption in comparison with conventional chiroptical methods, the lowest detectable analyte concentration is limited to ~1 mM to ensure sufficient molecule-metamaterial interactions, hindering the chiral sensing of trace urine metabolomes in clinical applications.

Herein, a method to overcome the abovementioned challenges in chiral sensing of metabolites is presented, the method uses microbubble-induced intense accumulation of biomolecules onto plasmonic chiral metamaterials. Benefiting from the increased molecular occupation at the superchiral fields, the chiral detection of solutions with glucose and lactate (dominant chiral metabolic molecules in urine) at concentrations down to 100 pM without the need of chiral reagents was achieved. The strongly enhanced sensitivity further enabled the chirality determination for solutions with mixtures of various metabolic molecules, requiring 10 μL samples only. Finally, in combination with a simple centrifugal purification process to exclude large nonmetabolic molecules and cells from urine, the accumulation-assisted plasmonic chiral sensing successfully uncovered the diabetes-induced abnormal chirality in urine samples from mice and humans with high diagnostic accuracy of 84% for human clinical samples.

Methods

Figure 16:
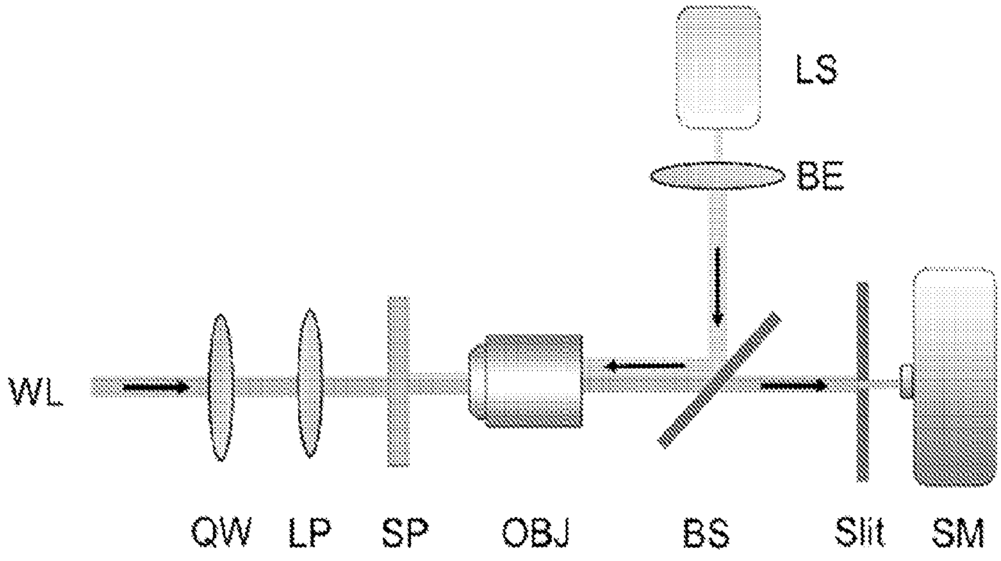
FIG. 16 is a schematic of the experimental setup for optical measurement. The abbreviations are continuous-wave laser (LS), sample (SP), objective (OBJ), beam splitter (BS), quarter-wave plate (QW), linear polarizer (LP), white light (WL), beam expander (BE) and spectrometer (SM), respectively.

Optical Setup. The experimental setup is shown in FIG. 16. The optical setup includes an inverted microscope (Ti-E, Nikon Inc.) with a white light source. A highly focused laser beam with a wavelength of 532 nm (Genesis MX-Series, Coherent) was first expanded with a 5× beam expander (GBEOS-A, Thorlabs) to increase the beam diameter. Then the beam diameter was reduced to 5 μm and applied to heat the moiré chiral metamaterials (MCMs) for microbubble generation after an infinity-corrected tube lens (Nikon) and an objective lens (Nikon, 40×, 0.75 NA). The circularly polarized light is generated by sequentially passing the broadband halogen lamp light through a linear polarizer (LPNIRE100-B, Thorlabs Inc.) and a quarter-wave plate (AQWP10M-980, Thorlabs Inc.). The transmission spectra of the circularly polarized light after passing through the moiré chiral metamaterials were collected with an in-situ spectrometer (Newton 970 EMCCD and Shamrock 500i, Andor Inc.). The tunable slit between the spectrometer and the objective is adjusted to 10 μm to avoid background noise. A motorized microscope stage (H101A, Prior Scientific) with stepper motor was used to precisely change the position of the focused laser beam in the x-y plane and aligned the laser at the center position on spectrometer for each measurement. LabVIEW software was used to control the power of the laser beam for bubble generation.

Substrate Fabrication. Moiré chiral metamaterials (MCMs) were fabricated on glass substrates through nanosphere lithography and wet etching/transfer as reported previously (Wu et al. *Advanced Optical Materials* 2017, 5, 1700034). Polystyrene spheres (300 nm in diameter) were purchased from Thermo Scientific Inc (3020A). The fabrication process can be divided into two processes. In process 1, the glass substrate was cleaned with acetone and deionized water with sonication (5 min), and then dried with nitrogen flow. A monolayer of the polystyrene spheres were then self-assembled into a hexagonally closed-packed colloidal monolayer on the glass substrate. Reactive ion etching (March Plasma CS170IF RIE Etching System) was used to reduce the diameters of the polystyrene spheres to ~250 nm with $O_2$ flow (20 sccm) and a power of 60 W. The substrate was then coated with a 2 nm chrome layer as an adhesive layer and a 30 nm Au layer through electron beam evaporation (Cooke Ebeam/Sputter Deposition System), The polystyrene spheres were peeled off using adhesive tape, leaving uniform Au nanohole arrays on the substrate.

In process 2, a sacrificial Cu layer with 100 nm thickness was firstly deposited on the precleaned glass substrate through electron beam evaporation (Cooke Ebeam/Sputter Deposition System). The following steps are similar to those of process 1. Briefly, uniform Au nanohole arrays were fabricated on the Cu layer. Then a thin poly(methyl methacrylate) (PMMA) film was spin coated (4000 r.p.m for 50 s) on the Au nanohole arrays, followed by baking at 130° C. for 60 s on a hotplate. Selective etching of the Cu substrate was achieved by floating the substrate on a Cu etchant (APS-100 Transene Inc.) for 30 min at 35° C. The floating substrate was then transferred onto the Au nanohole arrays fabricated in process 1, followed by drying overnight in vacuum oven at room temperature. The substrate was then dipped into an acetone solution for 20 min to remove the PMMA layer, washed with deionized water, and dried under nitrogen gas. Finally, the substrate was baked on a heater at 120° C. for 3 min to remove an excess water.

The patterning and fabrication of Au nanohole arrays can also be achieved via combination of electron-beam writing and mold-assisted transfer. Specifically, the combination of an electron-beam writer and a reactive ion etcher were applied to pattern Si wafers with desired nanohole arrays, which served as molds for metal deposition. A Cu layer with 5-10 nm thick and an Au layer with 20-40 nm thick were then deposited on the Si molds. A thermal-release tape was then applied on the top surface of the molds with deposited metals. The Cu layer, as a sacrificing layer, was then remove by floating the sample on a Cu etchant. The Si mold below the Cu layer was then detached from the metal layer, leaving the thermal-release tape with patterned Au layer. The tape was then picked up and applied to a pre-cleaned glass substrate or a substrate with pre-transferred Au nanohole array. The substrate was left to dry in vacuum for 16 hours. The thermal-release tape was then released by heating the dried substrate on a hot plate at 150° C. or 120° C., leaving the Au nanohole array on the substrate.

Chemical and Urine Preparation. L-glucose, D-glucose, L-lactate, and D-lactate were all purchased from Sigma-Aldrich. The solutions with various concentrations were prepared using filtered deionized water. Diabetic mice were purchased from Charles River Laboratories and were bred for use as type-II diabetes models. The de-identified human urine solutions were collected at clinics, prepped by centrifugation, and then aliquoted for storage at-80° C. To filter large cells, extracellular vesicles, and proteins, the urine samples were further centrifuged using 3K Da filters (EMD Millipore) and the remaining solution with ultra-metabolites was used for measurements.

Sample Preparation. Before experiments, the moiré chiral metamaterials were first washed using deionized water and dried with nitrogen gas, followed by oxygen plasma cleaning in UV ozone for 5 min. An adhesive spacer (0.12 mm deep) was firmly placed onto the moiré chiral metamaterial substrates. Next, a droplet of water or analyte solution (~10 μL) was added into the channels of the spacer. Another clean glass slide was then placed on the top of the analyte solution, forming a sealed microfluidic cell, which was then placed on the stage of the inverted microscope for analysis. The liquid was allowed to stabilize for 10 s and then the optical characterization was conducted.

After conducting the measurement(s), the top glass slide was removed and the droplet was removed to remove the analytes. The substrate was then dipped into deionized water for 5 min and dried with nitrogen flow to prepare the substrate for use in the next measurement.

Optical Characterization. Each optical measurement was conducted using accumulated acquisition protocols (100 times) to reduce the spectral noise. The total integration time for each measurement was 10 s. For each analyte, more than three measurements were conducted on left-handed moiré chiral metamaterials (LH-MCMs) and right-handed moiré chiral metamaterials (RH-MCMs), respectively. Specifically, in the stationary case, the circular dichroism spectra was first measured in deionized water without analytes and then measured with the analytes. In the accumulation assisted concentration case, the circular dichroism spectra was first measured before the preconcentration of the analytes and then conducted on the accumulation assisted concentration at the same location. After the bubble collapses, another circular dichroism spectra measurement was collected and compared with the previous circular dichroism spectra before preconcentration. The duration of each bubble preconcentration is described at the legend of each figure. The data was considered valid only when there was a continuous redshift in the transmission spectra after bubble concentration.

Numerical Simulations. A commercially available software package (FDTD Solutions, Lumerical Inc) was used to simulate the transmission spectra and near-field distributions of the moiré chiral metamaterials. The circularly polarized light was excited by the combination of an x-polarized plane-wave source with its phase set to 0, and a y-polarized plane-wave source with its phase set to +90 or −90 degree. The dielectric function of the Au was taken from Johnson and Christy (Olmon et al. *Physical Review B* 2012, 86, 235147). The reflective index of the surrounding medium was set to 1.33. The mesh size within the plasmonic materials was 5 nm in all three directions. The mesh size for other regions was adjusted to 10 nm. All outer boundaries were set as perfectly matched layers (PML).

Results

Working Principles of Accumulation-Assisted Plasmonic Chiral Sensing

Figure 17:
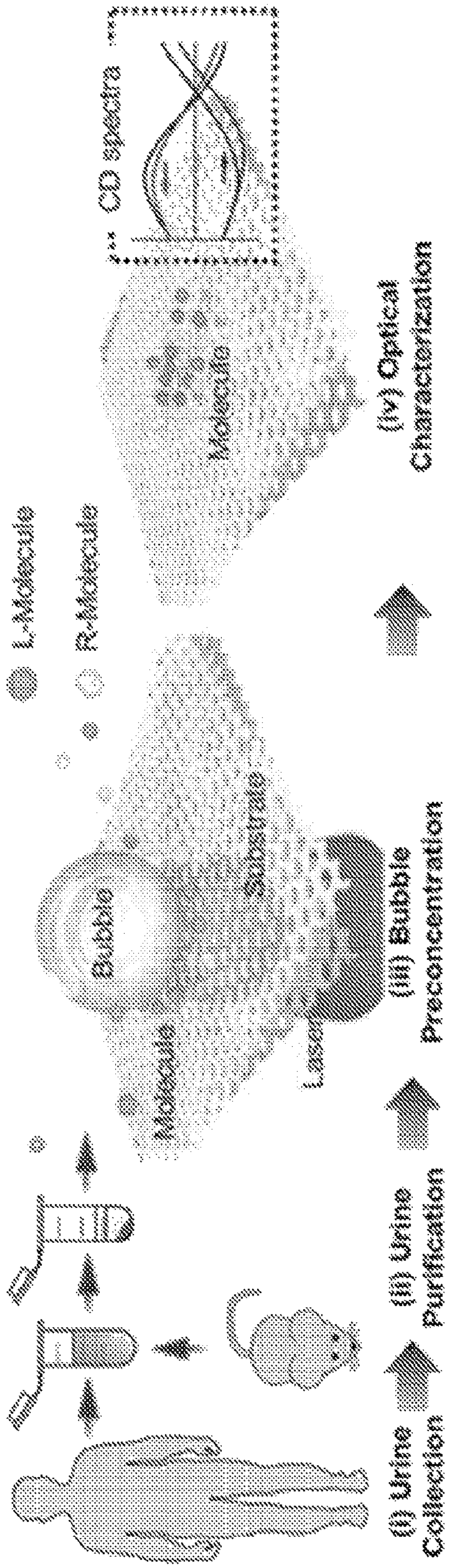
FIG. 17 is a schematic illustration of the collection and purification of urine samples, and the microbubble-enabled accumulation of chiral metabolic molecules on moiré chiral metamaterials for enhanced chiral sensing and diabetic detection via asymmetric spectral shifts.

The ultra-high sensitivity in chiral sensing of biomolecules is enabled by two enhancement mechanisms herein, including the microbubble-induced accumulation of biomolecules onto the chiral plasmonic substrates and the subsequent plasmon-enhanced chiral sensing. Herein, plasmonic moiré chiral metamaterials (MCMs) (Wu et al. *Advanced Optical Materials* 2017, 5, 1700034; Wu et al. *Advanced Optical Materials* 2018, 6, 1701057; Wu et al. *Nanoscale* 2018, 10, 18096-18112), which include two layers of Au nanohole arrays stacked into moiré patterns, were used to generate both the optothermal microbubbles and the superchiral fields. As shown in FIG. 17, the irradiation of a focused laser on to the moiré chiral metamaterials induced plasmon-enhanced optical heating at the laser focus point, vaporizing the solution above the substrate and generating a microbubble. The microbubble-induced Marangoni convection can effectively drag biomolecules in the solution towards the laser spot.

Figure 18:
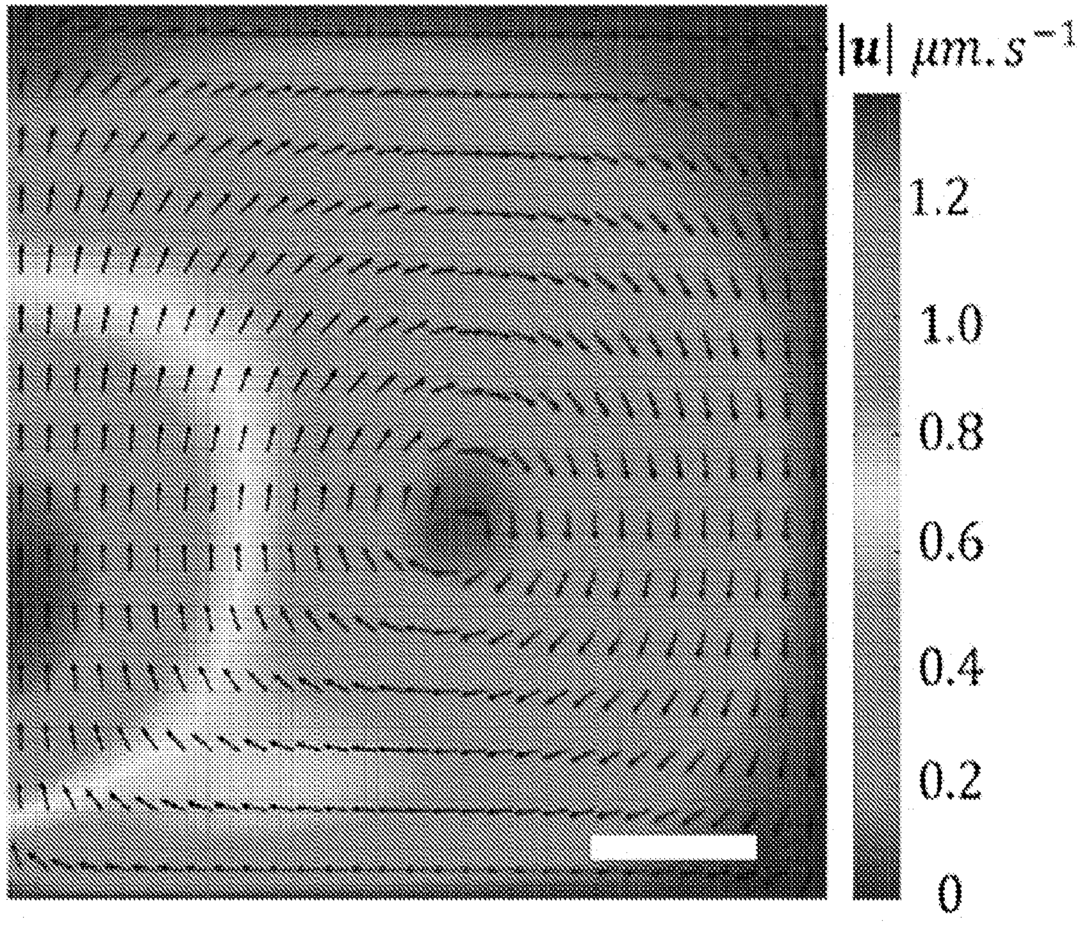
FIG. 18 is the simulated buoyancy-driven natural convection. The scale bar is 15 μm.
Figure 19:
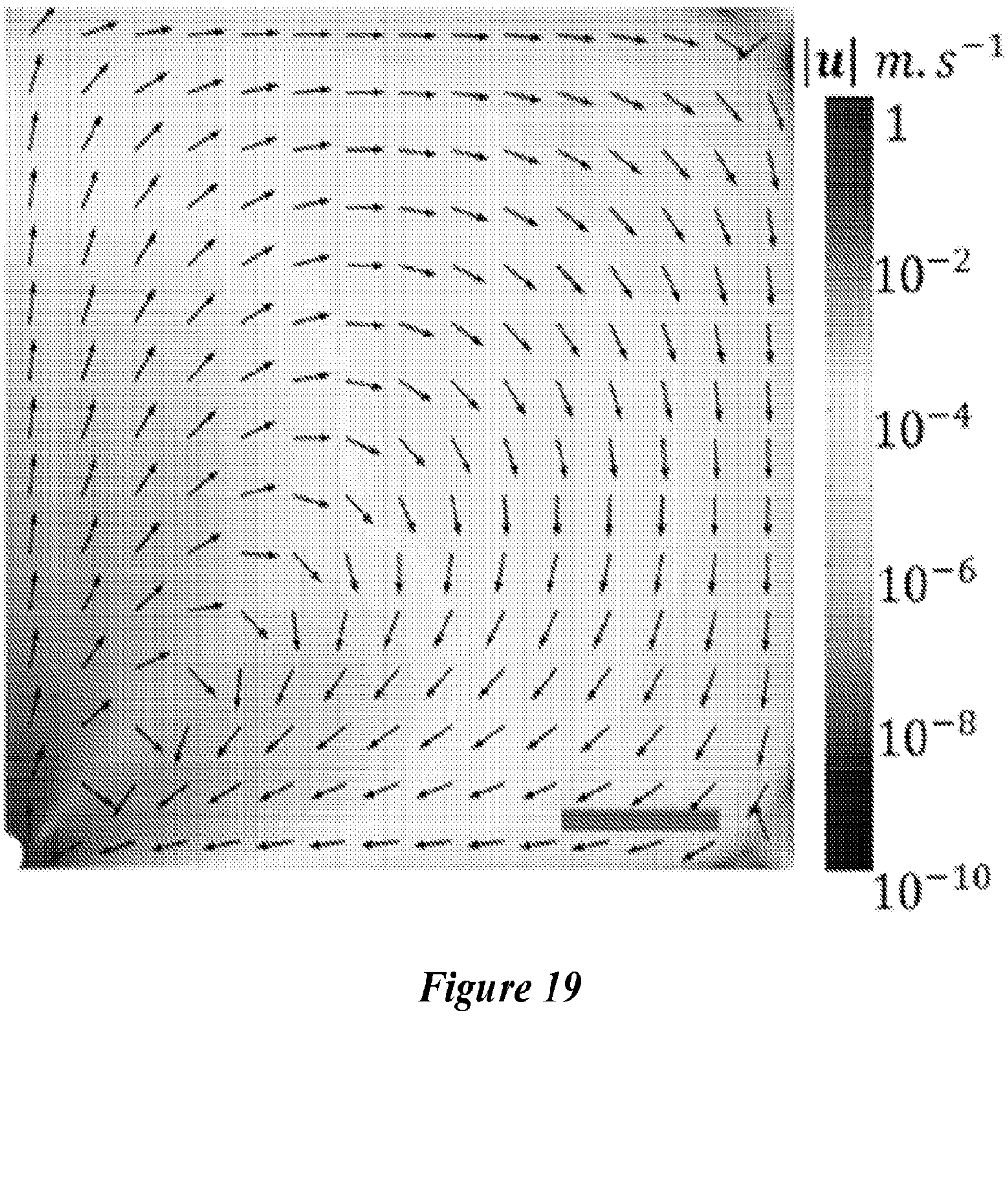
FIG. 19 is the simulated Marangoni convection with bubble. The scale bar is 15 μm.

The finite element analysis (FEM) simulation of the buoyancy-driven natural convection without a bubble and Marangoni convection with a bubble with a size of 5 μm were compared. As shown in FIG. 18 and FIG. 19, the simulated absolute value of natural convection velocity is within several μm/S and the maximum velocity happens at the center of the chamber with the velocity of 1.4 μm/S. However, the velocity of Marangoni convection flow with a bubble can reach approximately mm/S with a maximum velocity of ~0.5 m/S at the gas/liquid interface, which shows 5th order enhancement over the natural convection. Accordingly, the finite element analysis (FEM) simulation on a microbubble with size of 5 μm shows that the Marangoni convection dominates over natural convection by several orders of magnitude, enabling a maximum flow velocity of ~0.5 m/s near the gas/liquid interfaces (FIG. 18 and FIG. 19).

The drag forces for randomly distributed glucose molecules near the microbubble using were further simulated using FEM. Since the molecules (i.e., glucose and other metabolites) investigated herein are small, their motions do not affect the Marangoni velocity profile. Therefore, the force on the glucose molecule can be considered as mass times the acceleration of the flow. Since the flow considered is a steady state flow (steady state occurs in less than a millisecond), the acceleration of particle (same as that of flow) is solely convective in nature, i.e., and is given as:

$$a_{flow}=a_{particle}=(u\cdot\nabla)u \quad (1)$$

Figure 20:
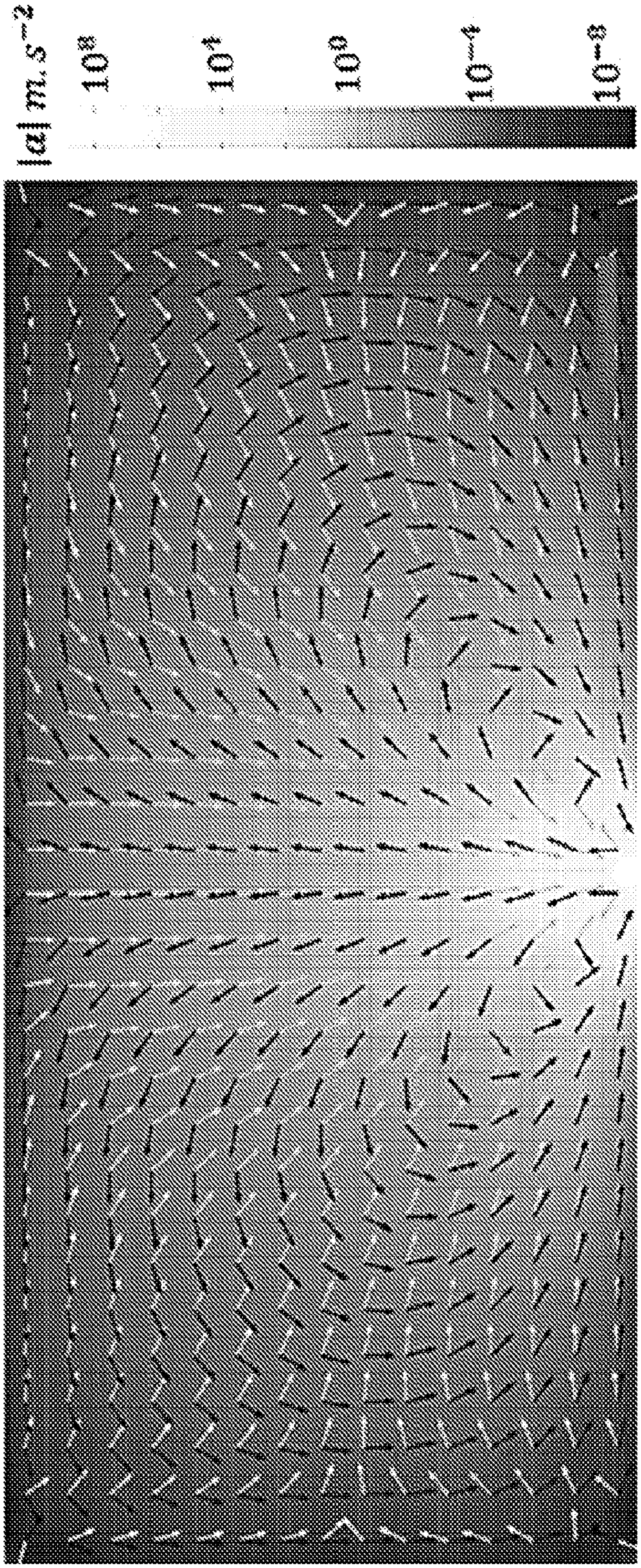
FIG. 20 is the acceleration of molecule around the bubble (simulated region is half of the figure with radial symmetry, two halves are shown for better understanding). Owing to small length scales and time scales with high velocities, the acceleration spans over 16 orders of magnitude, indicating that as molecules approach the bubble, high forces would assist in printing the molecule near the surface. The black arrows indicate the velocity direction and the cyan arrows indicate the acceleration (or force) direction. The scale bar is 10 μm.

The bubble is a sphere on a flat substrate, so a cylindrical coordinate system is employed to define the physics of simulation, and the radial and axial components of acceleration are given $$a_r = u_r\frac{\partial u_r}{\partial r} + u_z\frac{\partial u_r}{\partial z} \quad (1)$$

$$a_z = u_r\frac{\partial u_z}{\partial r} + u_z\frac{\partial u_z}{\partial z} \quad (2)$$

where u is velocity, a is acceleration, subscripts r and z indicate radial and axial components. Since the bubble is symmetrical in shape, the azimuthal component of acceleration is neglected. FIG. 20 shows the simulated steady state acceleration profile. The drag force can be calculated by multiplying its molecule mass, which is linearly correlated with the acceleration profile. The acceleration or force profile spans over 12 orders of magnitude and shows high values in the vicinity of the bubble. If force is perpendicular to the velocity, the molecule experiences a centripetal acceleration (changes the direction) and force aligned with the velocity indicates that the molecule experiences change of magnitude of velocity.

The simulations of the drag forces for the randomly distributed glucose molecules near the microbubble indicate that the drag force can reach ~0.01 fN near the microbubble surface for glucose molecules (FIG. 20), overcoming the limits in concentrating small biomolecules using other techniques such as thermoelectric (Lapizco-Encinas et al. *Analytical chemistry* 2004, 76, 1571-1579), thermophoretic (Wienken et al. *Nature communications* 2010, 1, 100) and electrothermoplasmonics (Garcia-Guirado et al. *ACS Photonics* 2018, 5, 3673-3679). The increased concentration of molecules near the substrate and the strong downward forces at the stagnation area near the microbubble-substrate interfaces then effectively print the molecules onto the plasmonic substrate with high binding affinity (Morasch et al. *Nature chemistry* 2019, 11, 779-788), enabling effective molecule accumulation for enhanced sensitivity.

Figure 21:
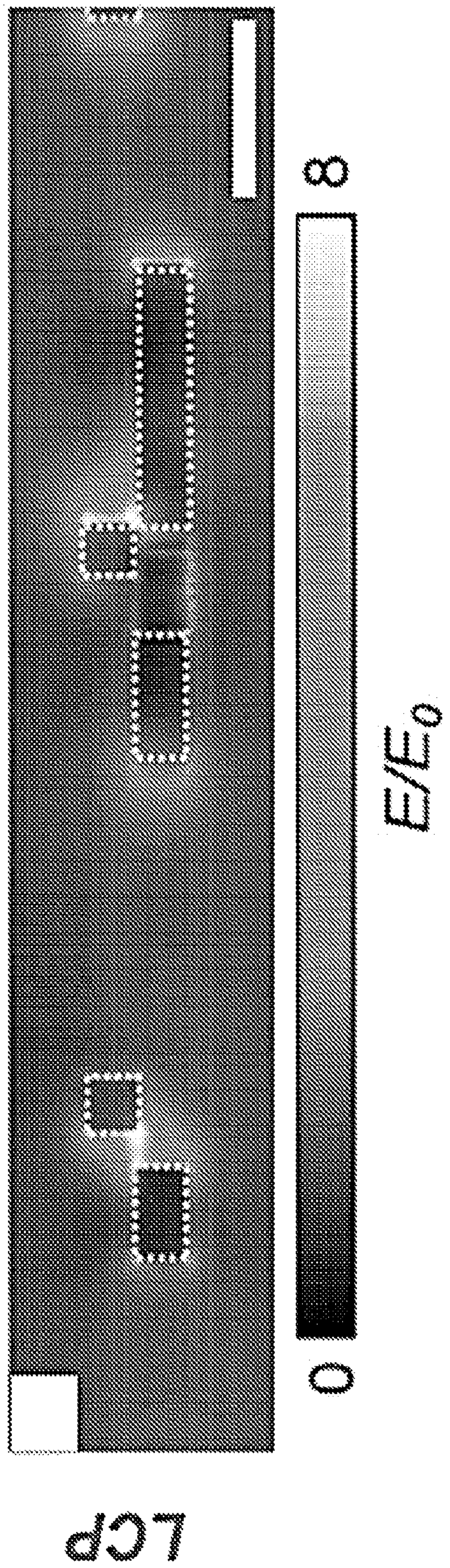
FIG. 21 is the simulated distribution of electric field enhancement in a left-handed moiré chiral metamaterial under left-handed circularly polarized illumination at wavelength of 675 nm. The scale bar is 100 nm.
Figure 22:
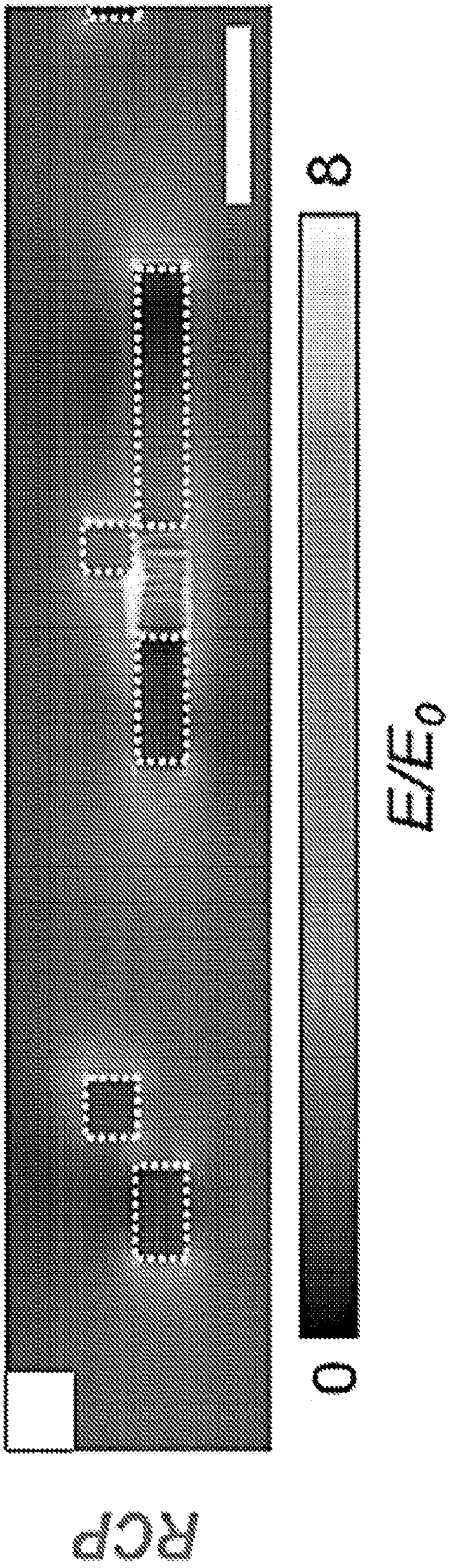
FIG. 22 is the simulated distribution of electric field enhancement in a left-handed moiré chiral metamaterial under right-handed circularly polarized illumination at wavelength of 675 nm. The scale bar is 100 nm.
Figure 23:
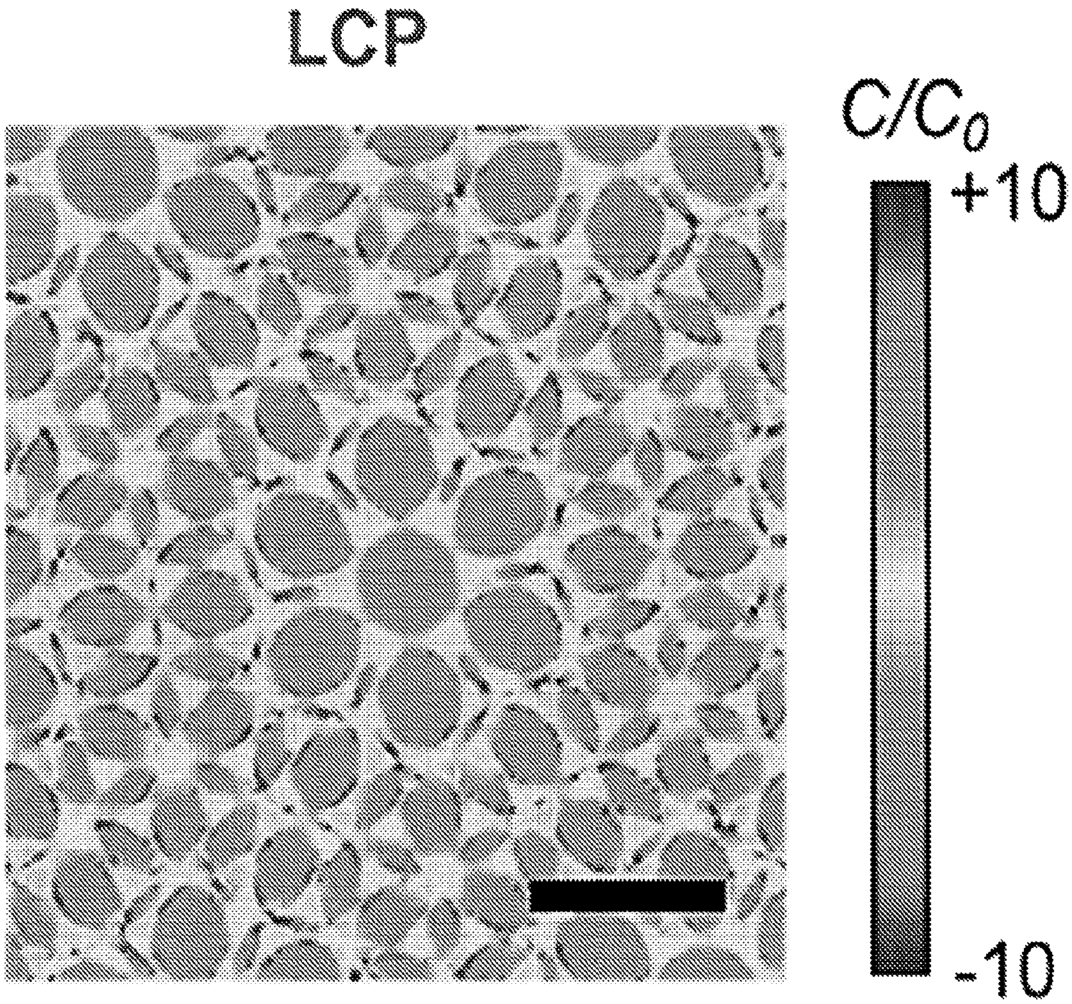
FIG. 23 is the simulated distribution of local optical chirality at the center plane of the left-handed moiré chiral metamaterial under left-handed circularly polarized illumination at a wavelength of 675 nm. The scale bar is 1 μm.
Figure 24:
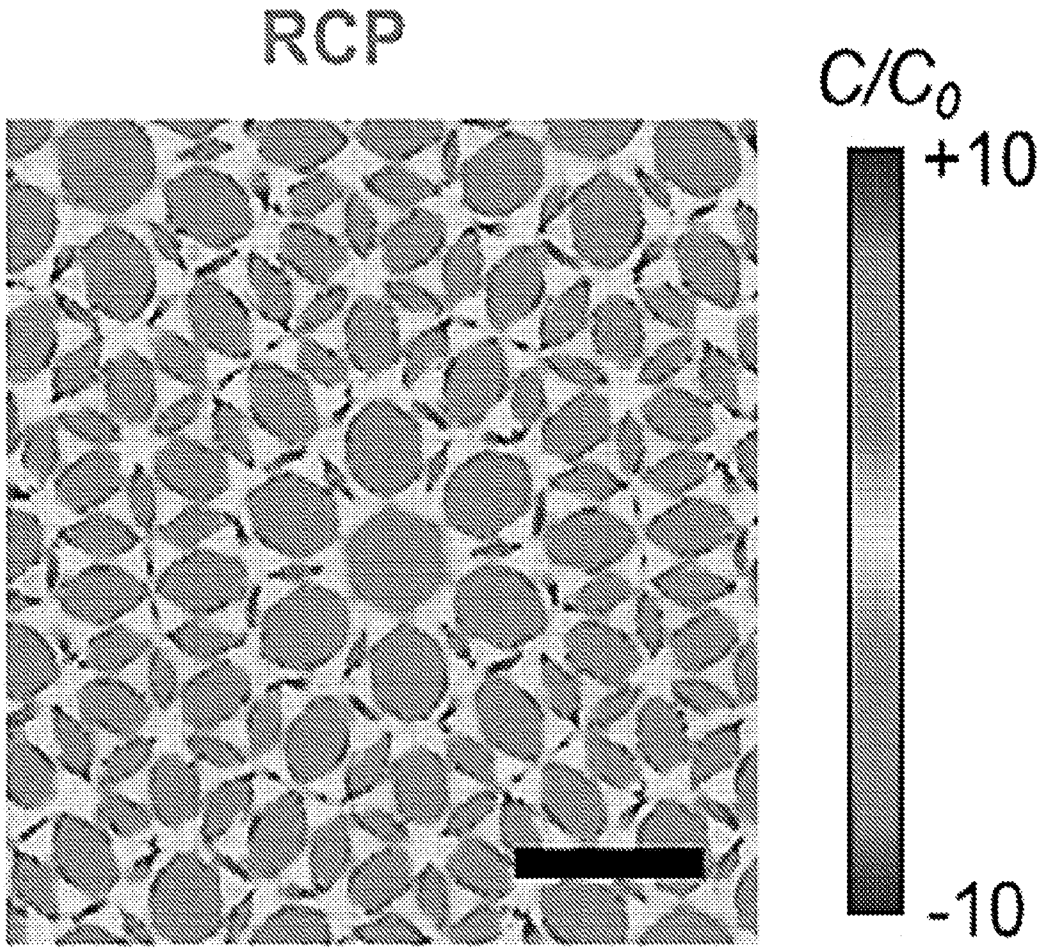
FIG. 24 is the simulated distribution of local optical chirality at the center plane of the left-handed moiré chiral metamaterial under right-handed circularly polarized illumination at a wavelength of 675 nm. The scale bar is 1 μm.

The plasmon-enhanced chiral near-fields further improves the chiral sensing of the accumulated molecules. The generation of strong near-field optical chirality in left-handed (LH) and right-handed (RH) moiré chiral metamaterials, with precisely controllable handedness through the interlayer rotation angle between the two layers of Au nanohole arrays, has previously been demonstrated (Wu et al. *Advanced Optical Materials* 2017, 5, 1700034; Wu et al. *Advanced Materials* 2019, 31, 1904132). FIG. 21 and FIG. 22 show the simulated cross-sectional distribution of plasmon-enhanced electric fields for a left-handed moiré chiral metamaterial with 15° interlayer rotation angle under incident light with right-handed circular polarization (RCP) and left-handed circular polarization (LCP), respectively. The large differences in both distribution and amplitude of electric hot spots under right-handed circularly polarized excitation and left-handed circularly polarized excitation show the strong chiroptical responses of the moiré chiral metamaterial. The superchiral fields, which are quantified by the local optical chirality (C), were further simulated in the moiré chiral metamaterial under left-handed circularly polarized excitation and right-handed circularly polarized excitation, as shown FIG. 23 and FIG. 24 respectively (Micsonai et al. *Proceedings of the National Academy of Sciences* 2015, 112, E3095-E3103). The local optical chirality (C) is obtained by:

$$C==n^2\varepsilon_0\omega\mathrm{Im}[E^*\cdot B]/2$$

where n is the refractive index, $\varepsilon_0$ is the free space permittivity, ω is the frequency, E is the local electric field, and B is the local magnetic field (Schäferling et al. *Physical Review X* 2012, 2, 031010; Tang et al. *Physical review letters* 2010, 104, 163901). The large enhancement factors (~10) of local optical chirality enable the strongly enhanced the chiral light-matter interactions and enantioselective discrimination of chiral metabolic molecules through asymmetric spectral shifts, as schematically shown in FIG. 17 (Huang et al. *Biomedical Chromatography* 2013, 27, 1100-1106).

Figure 25:
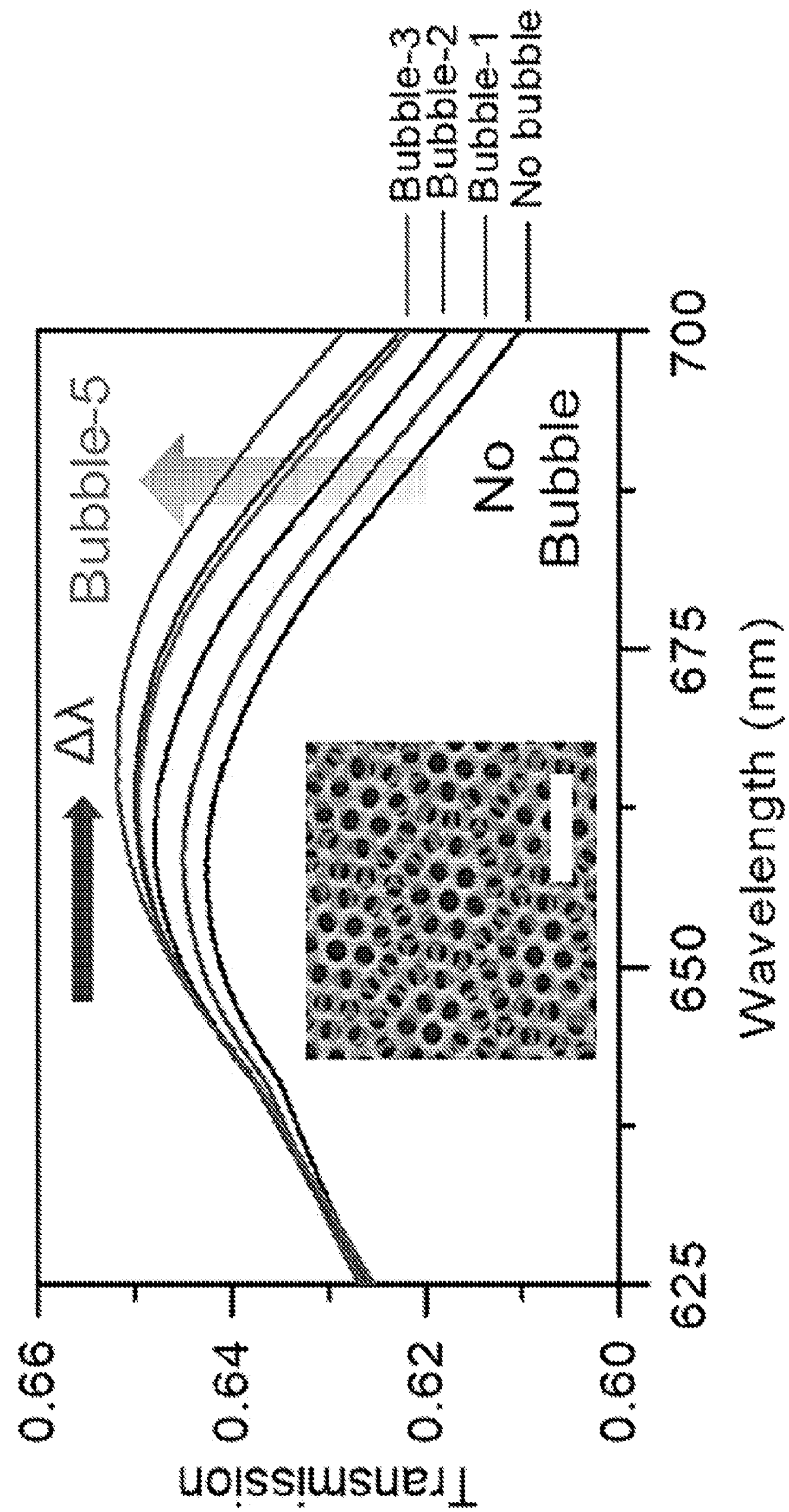
FIG. 25 is the evolution of transmission spectra of a left-handed moiré chiral metamaterial during the successive microbubble-assisted accumulation of glucose on the substrate. The inset shows the corresponding SEM images of the left-handed moiré chiral metamaterial. The scale bar is 1 μm.
Figure 26:
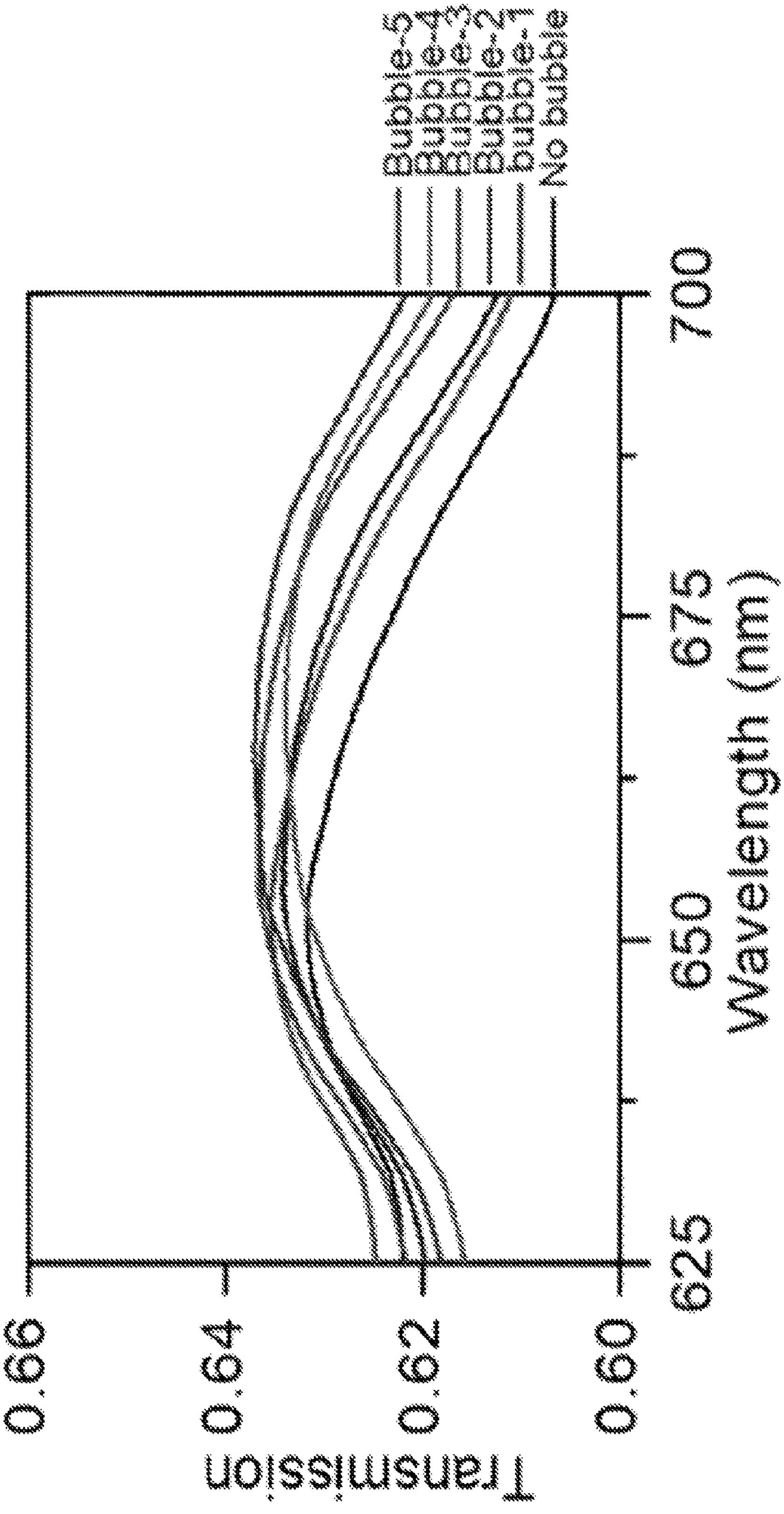
FIG. 26 is the transmission spectra of a right-handed moiré chiral metamaterial after 5 successive bubble assisted concentrations.
Figure 27:
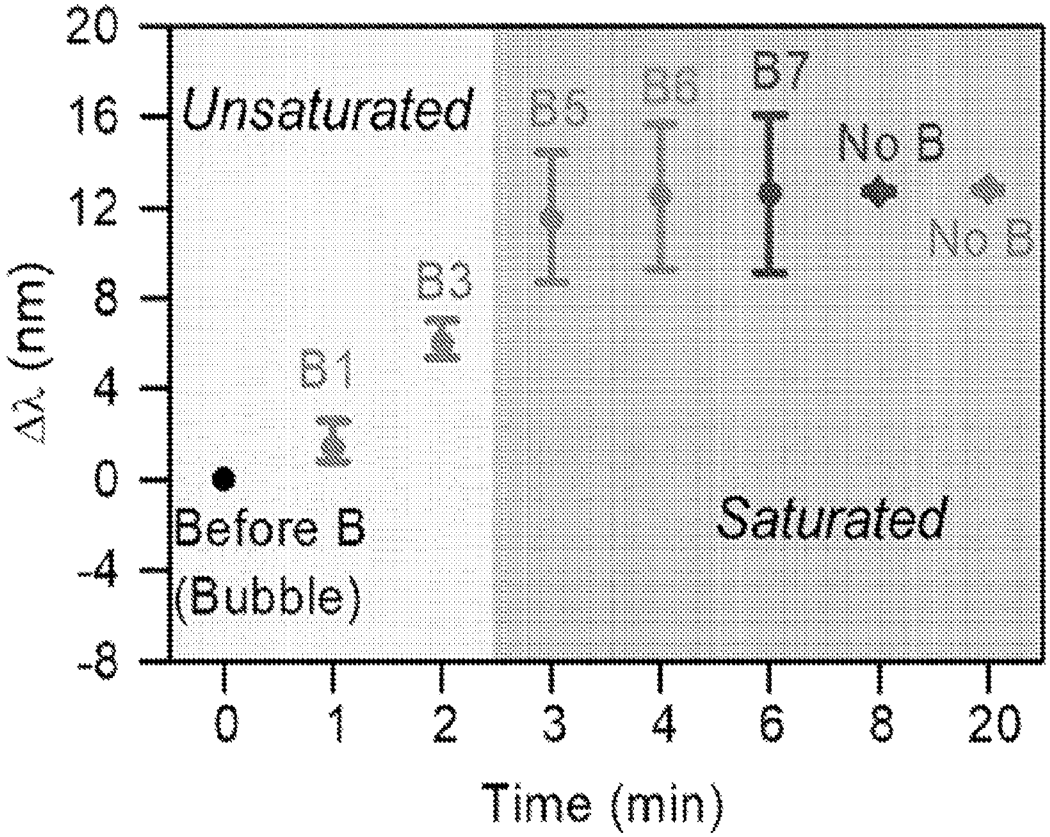
FIG. 27 is the averaged peak shifts (Δλ) of transmission spectra of multiple moiré chiral metamaterials during the successive microbubble-assisted accumulations of glucose. The x axis shows the time of each measurement.
Figure 28:
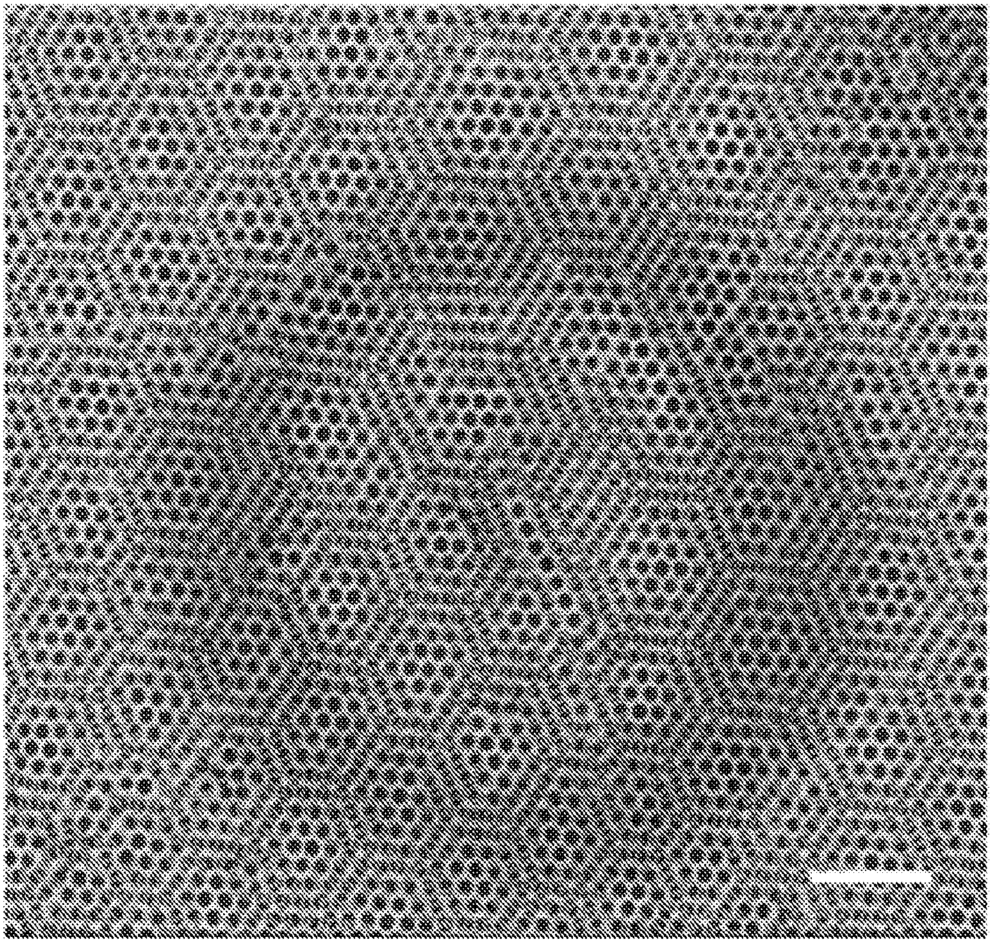
FIG. 28 is an SEM image of the substrate after bubble concentration. The scale bar is 2 μm.

The microbubble-assisted accumulation on moiré chiral metamaterials and its effects in chiral sensing using 100 μM glucose solution in deionized water were tested. Successive microbubbles were generated at the same spot, where each microbubble was maintained for 5 seconds and allowed to collapse before the generation of the next microbubble. The total time from bubble generation to collapse was within 10 s, showing several orders faster molecule accumulation than other techniques (Lapizco-Encinas et al. *Analytical chemistry* 2004, 76, 1571-1579). The optical transmission of the moiré chiral metamaterials was measured after the collapse of each bubble. Continuous redshifts in the transmission spectra were observed after the successive generation of microbubbles on both left-handed moiré chiral metamaterials (FIG. 25) and right-handed moiré chiral metamaterials (FIG. 26). The spectral shifts (Δλ) are saturated at ~12 nm after 5 microbubbles and remain unchanged after more than 10 minutes without new microbubble generation (FIG. 27), indicating the complete and stable occupation of plasmonic hot spots with accumulated glucose molecules. The scanning electron microscope image in FIG. 28 shows the concentrated glucose molecules on the moiré chiral metamaterial after the collapse of the microbubble, confirming that the molecules are firmly printed on the substrates.

A 20× objective was used to generate an approximately 7 μm size bubble to concentrate glucose on the substrate. After washing and drying the substrate, the scanning electron microscopy (SEM) images of the substrate were collected. As shown in FIG. 28, there is a clear ring shape pattern indicating that the printing happens around the bubble edges. The microbubbles were generated using optimized laser power to ensure that the local temperature is below the denaturizing point (146° C.) for glucose (Hurtta et al. *Carbohydrate research* 2004, 339, 2267-2273; Pazur et al. *Biochemistry* 1964, 3, 578-583). Since the laser power is adjusted just above threshold power for bubble generation, photothermal damage of the substrate at the center was not observed.

Figure 29:
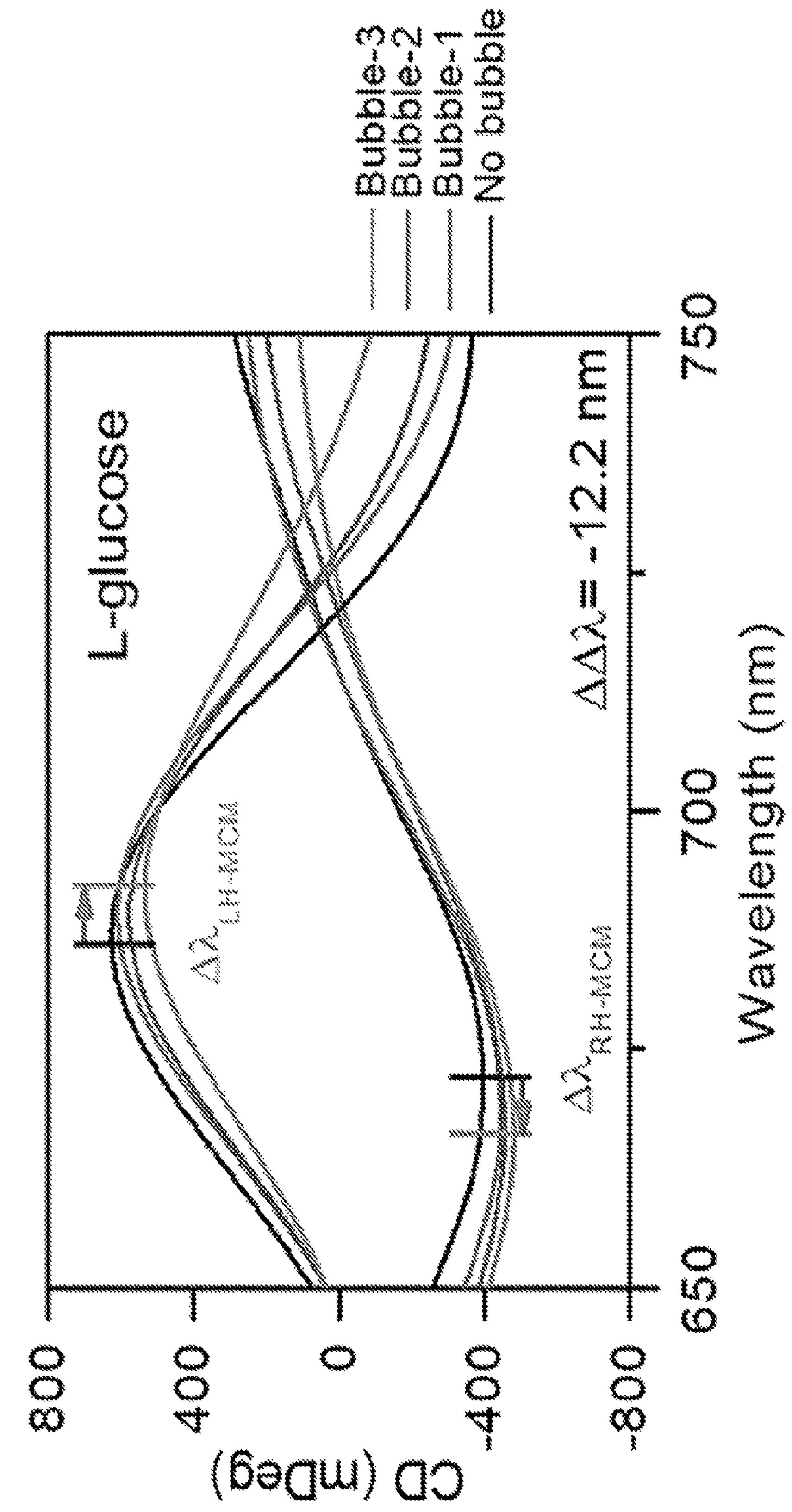
FIG. 29 is the evolution of circular dichroism spectra of left-handed moiré chiral metamaterials and right-handed moiré chiral metamaterials during the successive microbubble-assisted accumulations of L-glucose.
Figure 30:
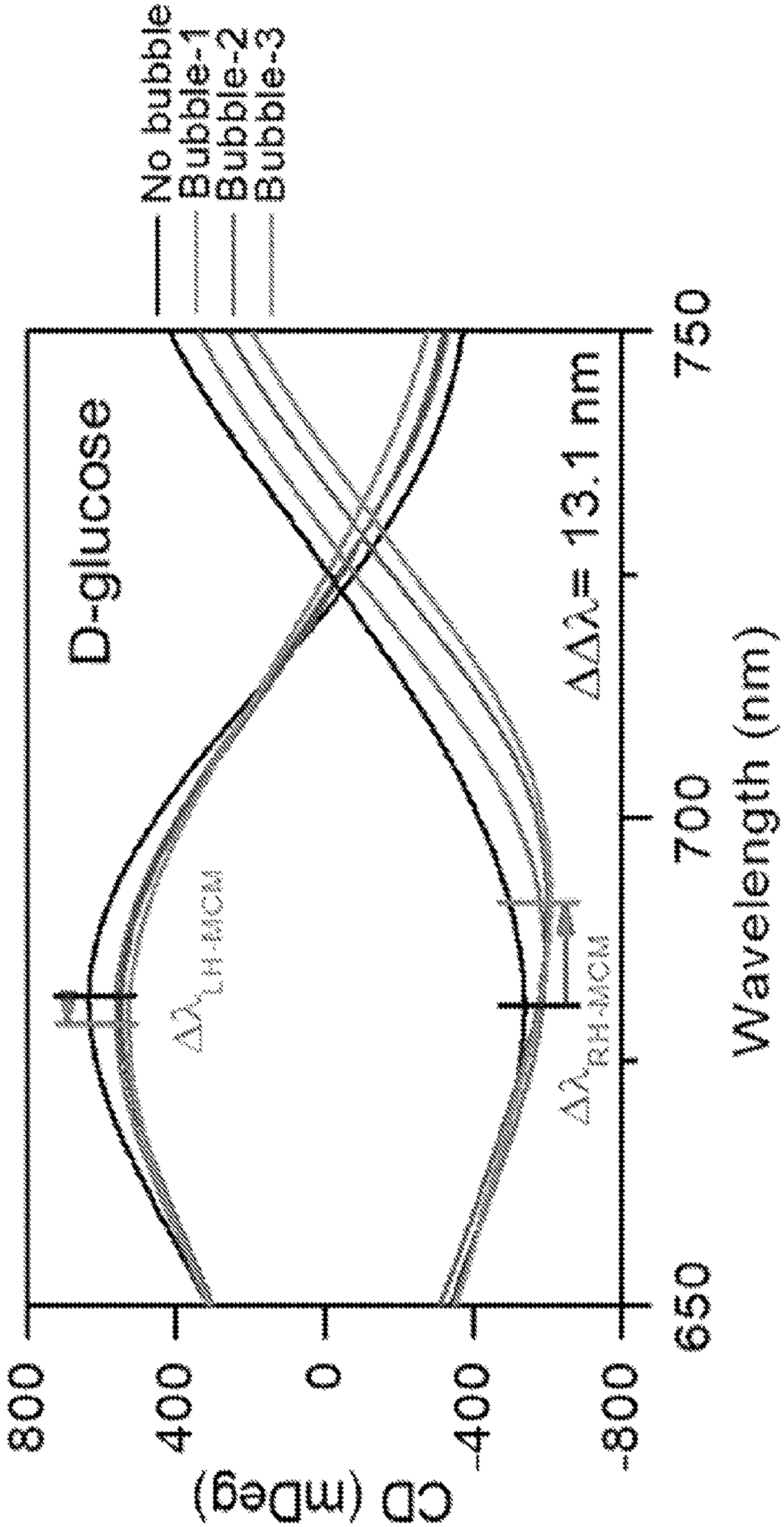
FIG. 30 is the evolution of circular dichroism spectra of left-handed moiré chiral metamaterials and right-handed moiré chiral metamaterials during the successive microbubble-assisted accumulations of D-glucose.

The chiral sensing of the accumulated molecules was then achieved by analyzing the asymmetric shifts of the circular dichroism spectra of left-handed moiré chiral metamaterials and right-handed moiré chiral metamaterials upon the adsorption of chiral molecules. Here the circular dichroism is obtained by 32.98°× ($T_{RCP}-T_{LCE}$), where $T_{RCP}$ and $T_{LCP}$ are the optical transmission of moiré chiral metamaterials under right-handed circular polarization and left-handed circular polarization light, respectively (Wu et al. *Advanced Optical Materials* 2017, 5, 1700034). FIG. 29 and FIG. 30 show the circular dichroism spectra shifts of the left-handed moiré chiral metamaterials and right-handed moiré chiral metamaterials induced by the successive microbubble-assisted accumulation of L- and D-glucose, respectively. The successive printing of L-glucose on the substrate causes continuous redshifts for the circular dichroism peak of the right-handed moiré chiral metamaterial and continuous blueshifts for the circular dichroism dip of the left-handed moiré chiral metamaterials, as shown in FIG. 29. In contrast, the spectral shifting trends are reversed for the D-glucose cases (i.e. blueshifts for the right-handed moiré chiral metamaterial and redshifts for the left-handed moiré chiral metamaterials), as shown in FIG. 30.

Figure 31:
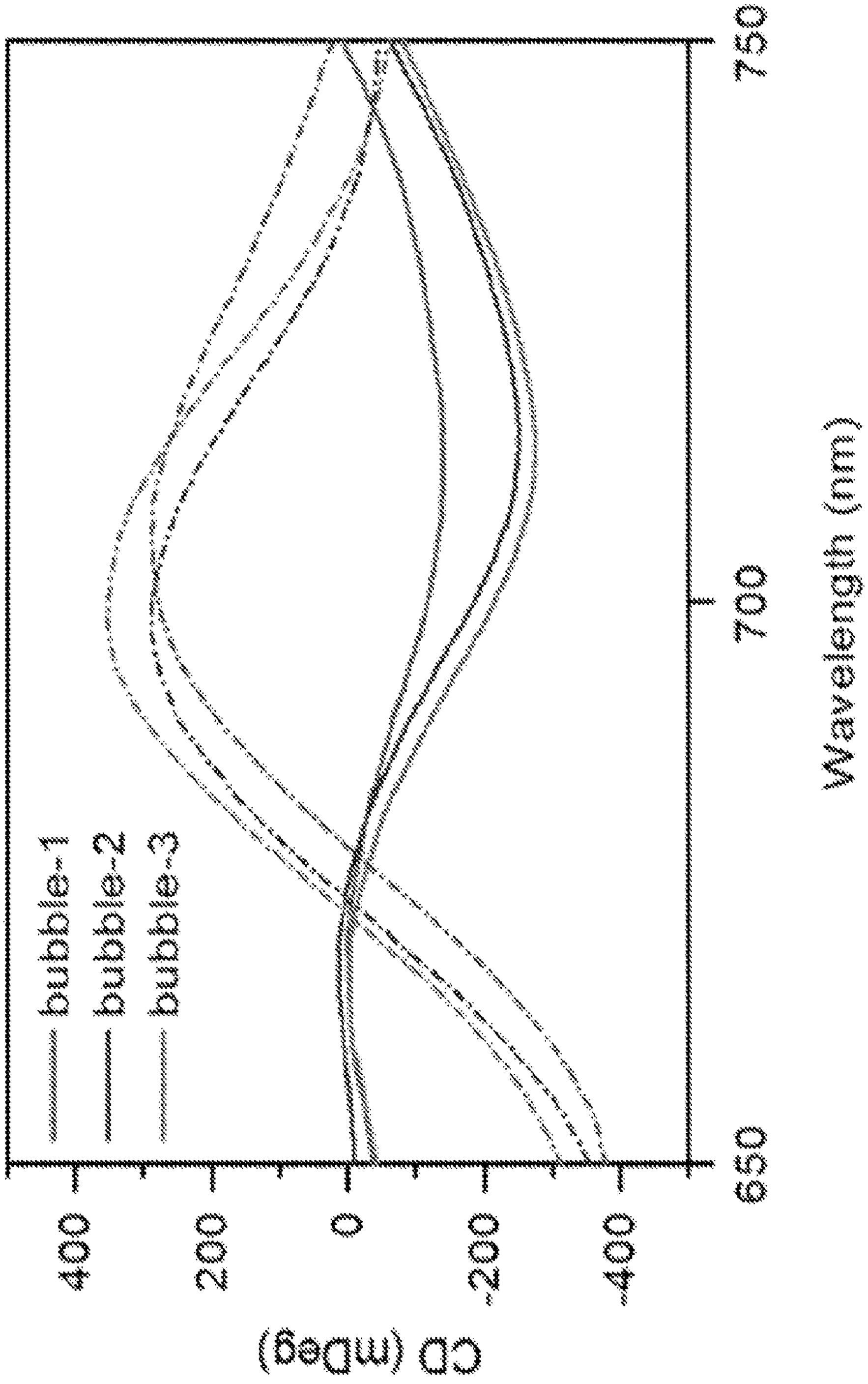
FIG. 31 is the circular dichroism summation for L-glucose (dashed lines) and D-glucose (solid lines).

The molecular chirality-dependent asymmetric circular dichroism spectral shifts of the moiré chiral metamaterials were quantified using dissymmetry factors: $\Delta\Delta\lambda=\Delta\lambda_{RH-MCM}-\Delta\lambda_{LH-MCM}$, where $\Delta\lambda_{RH-MCM}$ and $\Delta\lambda_{LH-MCM}$ are the circular dichroism spectral shifts of left-handed moiré chiral metamaterial and right-handed moiré chiral metamaterial, respectively, due to the microbubble-induced accumulation of chiral molecules on the moiré chiral metamaterials. As shown in FIG. 29 and FIG. 30, the successive generation of 3 microbubbles (completed in less than 1 minute) leads to dissymmetry factors of −12.2 nm and 13.1 nm for 100 μM solution of L- and D-glucose, respectively, enabling the effective detection of molecular chirality. The chiral sensing effectiveness of this technique was further verified by comparing the magnitudes of circular dichroism spectra of the left-handed moiré chiral metamaterials and right-handed moiré chiral metamaterials before and after molecule adsorption (Kelly et al. *ACS Photonics* 2018, 5, 535-543; Garcia-Guirado et al. *Nano letters* 2018, 18, 6279-6285), where asymmetric summation of circular dichroism can be generated by chiral molecules as shown in FIG. 31.

Circular dichroism summation is an alternative method to characterize the plasmonic chiral sensor (Garcia-Guirado et al. *Nano letters* 2018, 18, 6279-6285; Hentschel et al. *Science advances* 2017, 3, e1602735; Zhao et al. *Nature communications* 2017, 8, 1-8; Lee et al. *ACS Photonics* 2017, 4, 2047-2052). For L-glucose (dashed lines, FIG. 31) the circular dichroism spectra include a peak around 700 nm. For D-glucose (solid lines, FIG. 31), the circular dichroism spectra include a dip around 700 nm. For simplicity, spectra shift is used for the rest of this study.

Figure 32:
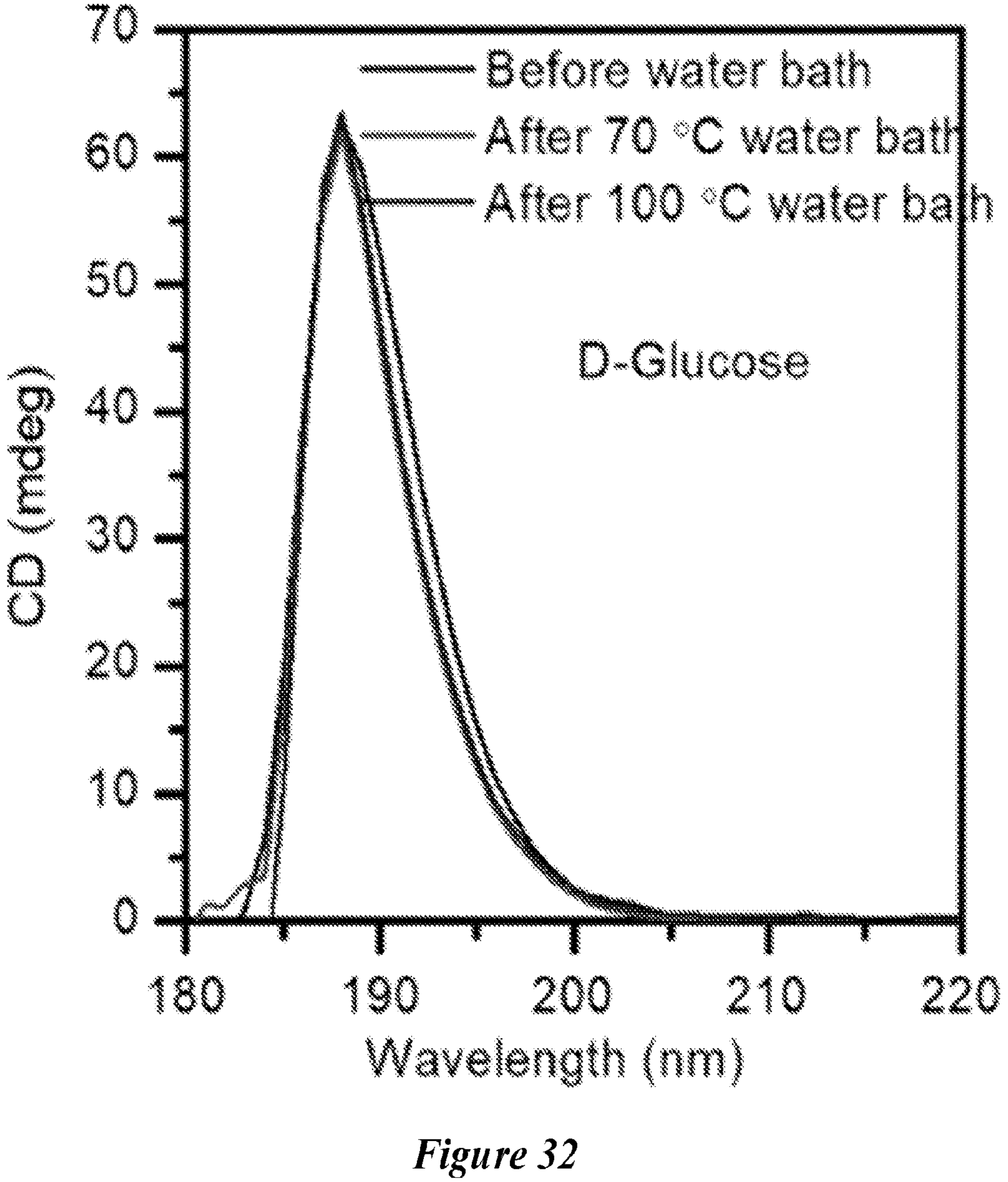
FIG. 32 is the circular dichroism spectra for D-glucose before and after water baths under different temperature using Jasco CD J-815. The water bath duration is 2 min and D-glucose concentration is 100 mM.

To confirm that no photothermally induced chiral denaturation occurs during microbubble generation, the circular dichroism spectra of D-glucose solution was measured using a UV-circular dichroism spectrometer before and after water baths at 70° C. and 100° C. As shown in FIG. 32, there is no circular dichroism spectra change even after the boiling water bath. The circular dichroism spectra become invalid below 190 nm due to strong absorption of water. The absence of spectral changes caused by the water baths indicate that the chiral parameters of glucose remain stable at water vapor generation temperature (e.g., 100° C.) (FIG. 32). Similar stability was also observed in optical rotation measurements before and after water baths.

Figure 33:
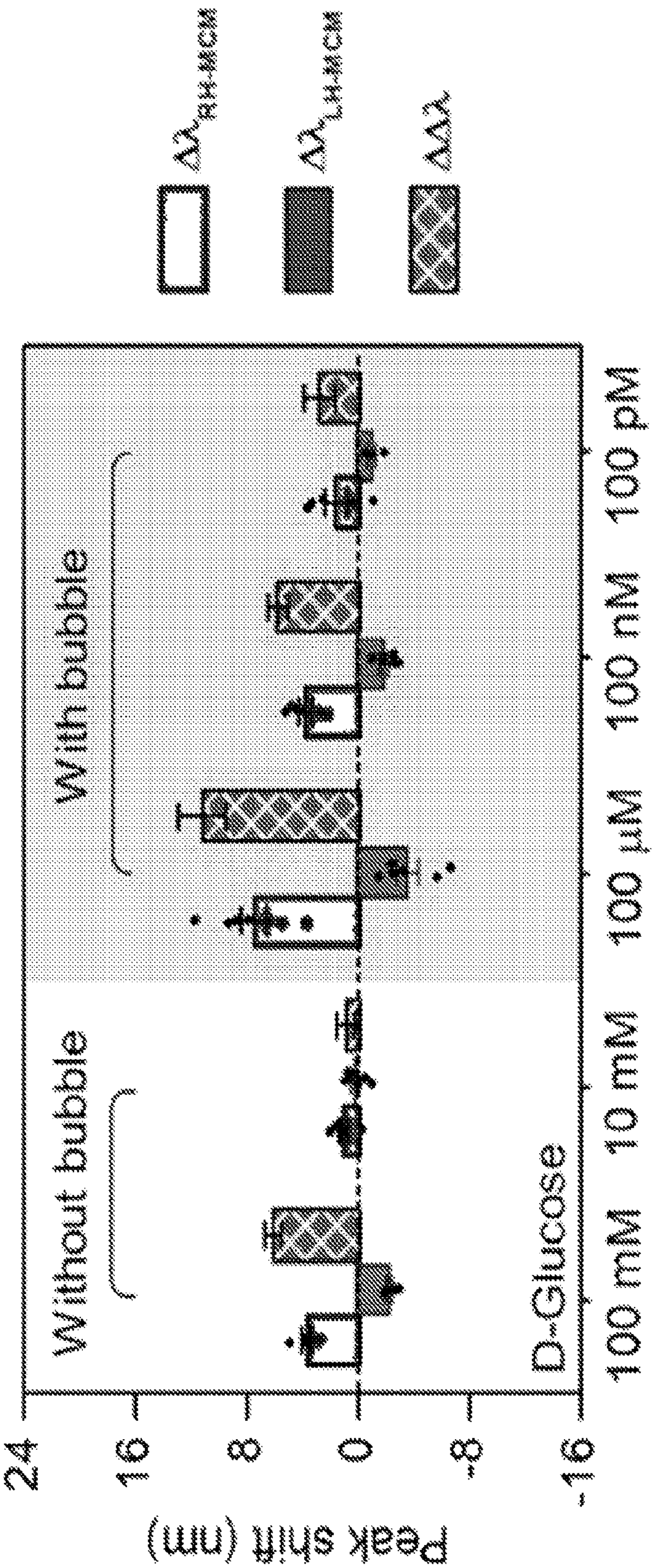
FIG. 33 is the circular dichroism spectral shifts (Δλ) and dissymmetry factors (ΔΔλ) induced by adsorption of D-glucose at different concentrations with and without microbubble-enabled accumulation. The bubble concentration time for 100 μM, 100 nM and 100 μM solutions are 5 s, 60 s, and 20 min, respectively. Error bars indicate mean±S.D.
Figure 34:
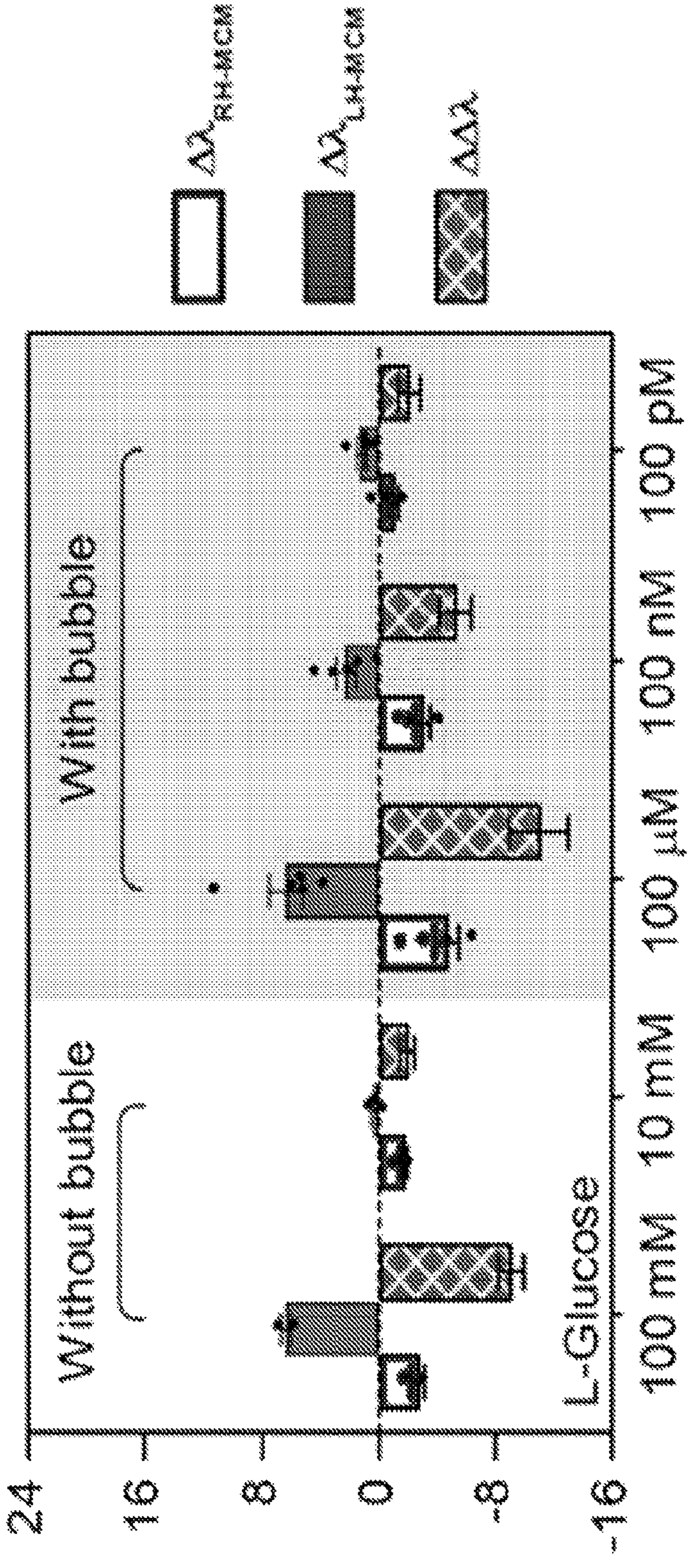
FIG. 34 is the circular dichroism spectral shifts (Δλ) and dissymmetry factors (ΔΔλ) induced by adsorption of L-glucose at different concentrations with and without microbubble-enabled accumulation. The bubble concentration time for 100 μM, 100 nM and 100 μM solutions are 5 s, 60 s, and 20 min, respectively. Error bars indicate mean±S.D.

The large enhancement in sensitivity of the chiral sensing achieved by microbubble-induced accumulation was further demonstrated. The dissymmetry factors obtained by accumulation-enhanced sensing and conventional stationary sensing without microbubble generation, where the chirality detection is achieved by the comparison between circular dichroism shifts in solution with and without chiral molecules (Hendry et al. *Nature nanotechnology* 2010, 5, 783; Zhao et al. *Nature communications* 2017, 8, 14180), were compared. FIG. 33 and FIG. 34 show the sensing performances for both D- and L-glucose solution with various concentrations. For stationary sensing without microbubble-induced accumulation, the dissymmetry factors (ΔΔλ) of both D- and L-glucose solution decrease as concentration decreases. At a concentration of 10 mM (i.e., 18 mg/mL), ΔΔλ has a negative value of −1.8 nm for L-glucose and a positive value of 1.9 nm for D-glucose, which are comparable to state-of-the-art superchiral-fields-enabled chiral sensing (Micsonai et al. *Proceedings of the National Academy of Sciences* 2015, 112, E3095-E3103). When the glucose concentration was further reduced, the circular dichroism spectra shifts could not be resolved using the stationary method, leading to undetectable chirality. In comparison, the microbubble-induced accumulation-enhanced sensing achieved dissymmetry factors at glucose concentrations of 100 μM that were even larger than the values obtained at 100 mM using the stationary method, as shown in FIG. 33 and FIG. 34. Extraordinarily, the chirality of glucose was still able to be resolved at concentrations down to 100 pM (i.e., 18 pg/mL) using the microbubble-induced accumulation method, which shows ~$10^7$ times enhancement in sensitivity compared to state-of-the-art plasmonic chiral sensors (Tullius et al. *J. Am. Chem. Soc.* 2015, 137, 8380-8383; Zhao et al. *Nature communications* 2017, 8, 14180).

Chirality Determination of Metabolite Mixtures

Figure 35:
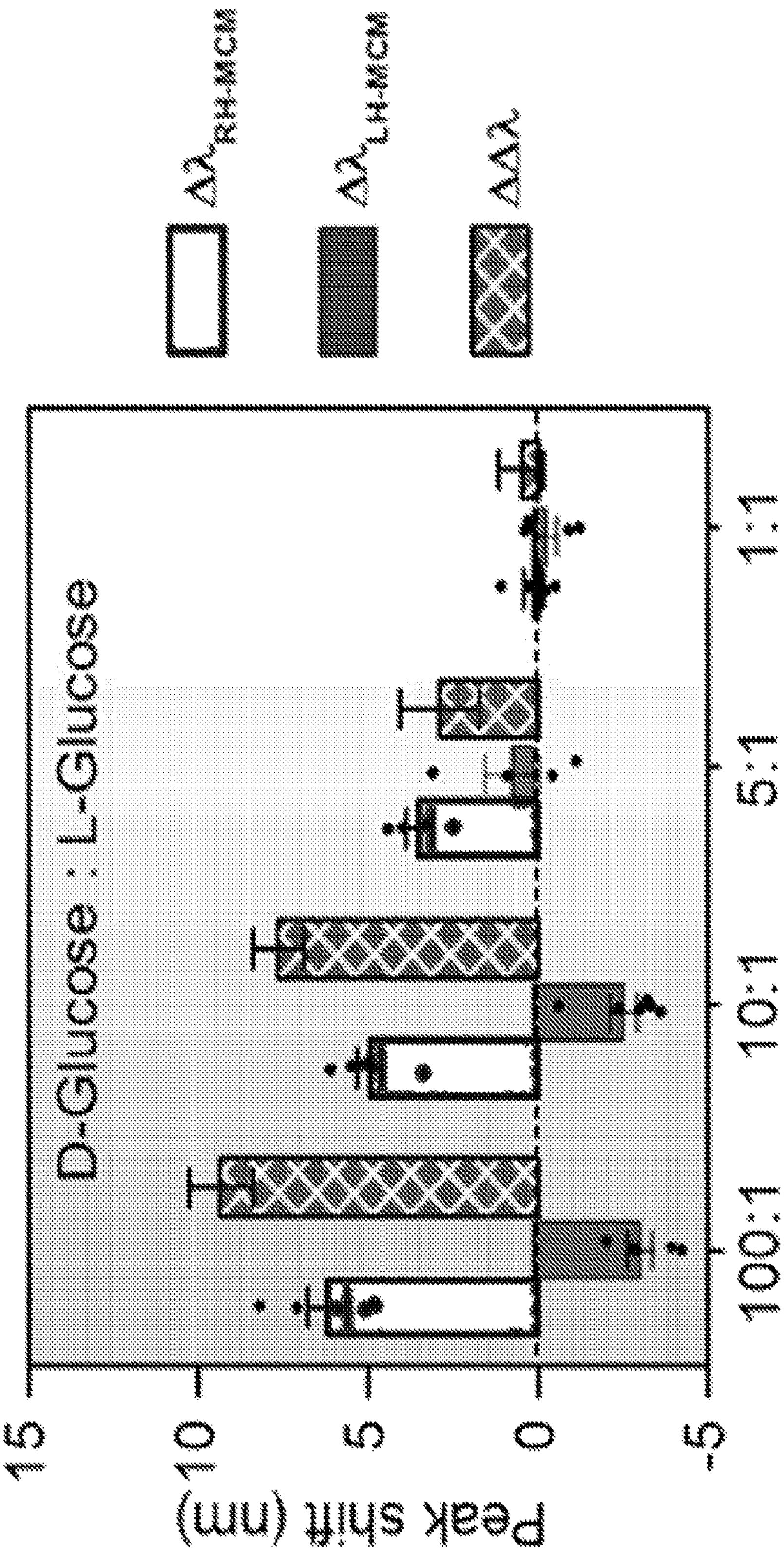
FIG. 35 is the circular dichroism spectral shifts (Δλ) and dissymmetry factors (ΔΔλ) at various ratios of D- and L-glucose mixture solution with 100 μM total concentration. Error bars indicate mean±S.D. The bubble concentration time for the mixture solutions is 5 s.

The accumulation-assisted plasmonic chiral sensing was further applied for ultra-sensitive monitoring of chirality changes in solutions of various mixtures of chiral biomolecules. Such capability is crucial in developing techniques for quantitatively monitoring chirality of urine metabolites, which include enantiomers of various metabolic molecules. The accumulation-assisted plasmonic chiral sensing was first used to determine the chirality of a solution with D- and L-glucose at various enantiomeric ratios, as shown in FIG. 35. The dissymmetry factor (ΔΔλ) gradually decreases from ~9 nm to ~0 nm as the ratio between D- and L-glucose decreases from 100:1 (i.e., near pure) to 1:1 (i.e. racemic), showing a good match between measured chirality via accumulation-assisted plasmonic chiral sensing and the actual enantiomeric status in solution. The chirality of mixtures with different chiral biomolecules was further tested. As an example, the dissymmetry factors of solutions with mixtures of D-glucose and L-lactate at various ratios was measured.

Figure 36:
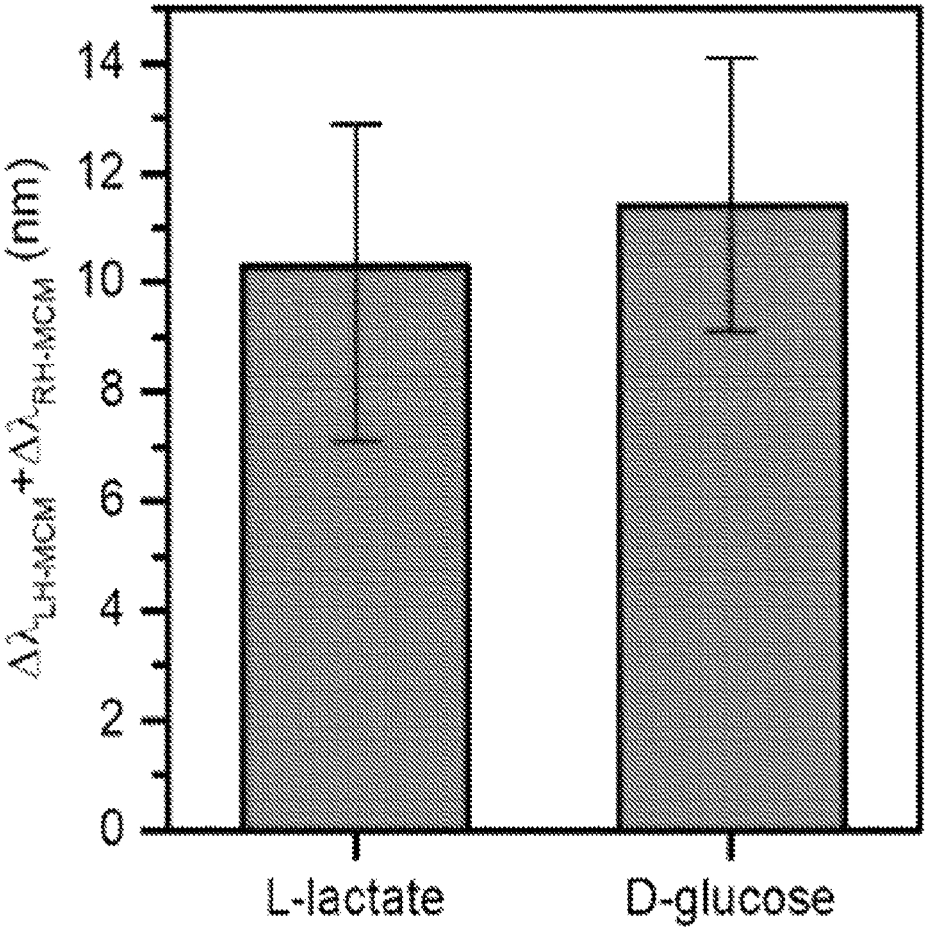
FIG. 36 is the $\Delta\lambda_{LH\text{-}MCM}+\Delta\lambda_{RH\text{-}MCM}$ of multiple moiré chiral metamaterials for D-glucose and L-lactate after bubble concentrations under linearly polarized light illumination.
Figure 37:
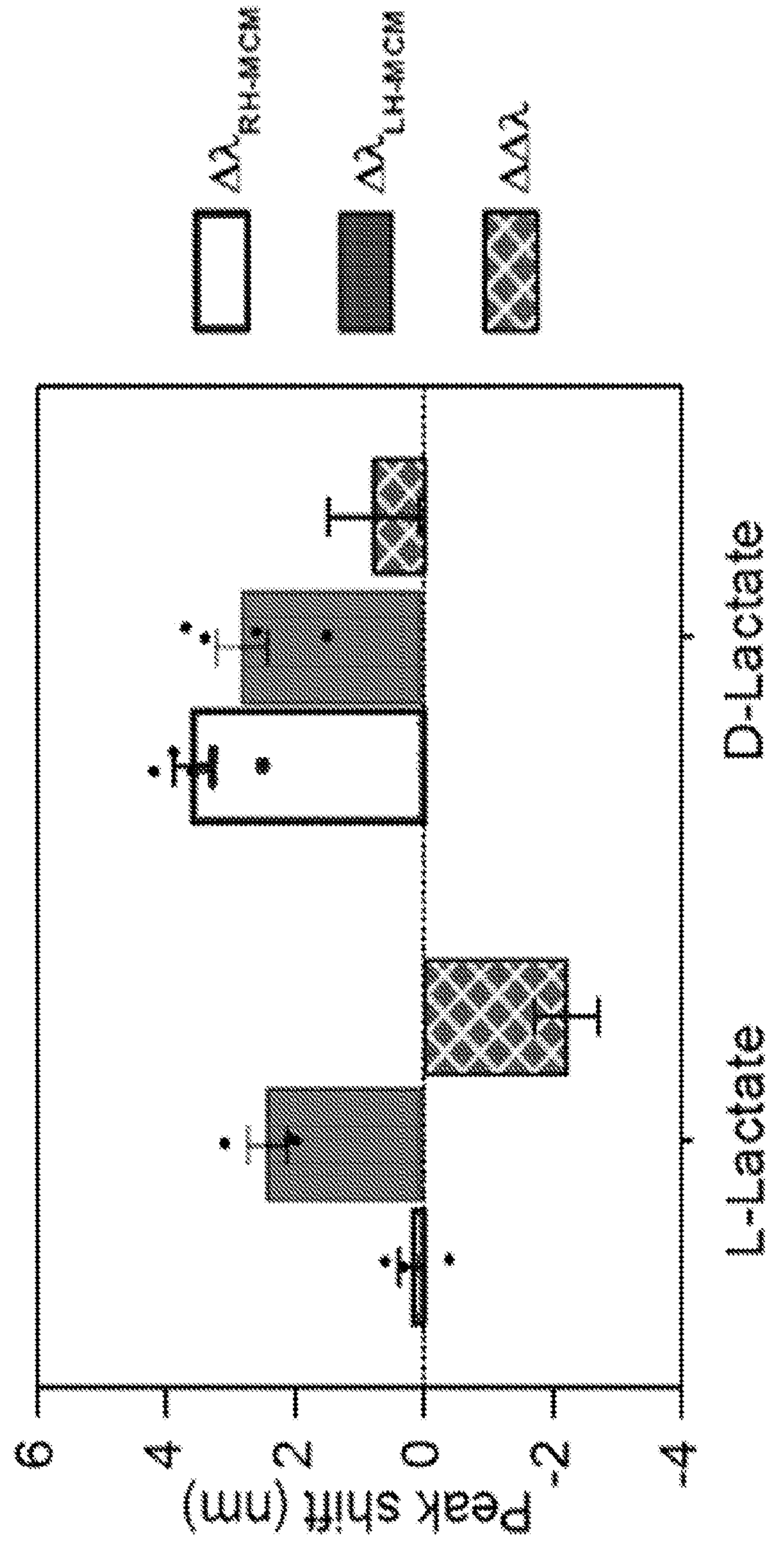
FIG. 37 is the circular dichroism spectral shifts (Δλ) and dissymmetry factors (ΔΔλ) of L- and D-lactate. Error bars indicate mean±S.D. The bubble concentration time for the lactate solutions is 5 s.

To investigate the concentration efficiency between glucose and lactate, the transmission spectra for multiple left-handed moiré chiral metamaterials and right-handed moiré chiral metamaterials were measured under linearly polarized light after bubble concentrations of D-glucose and L-lactate. The spectra shift was calculated by the summation of spectra shift in both left-handed moiré chiral metamaterials and right-handed moiré chiral metamaterials cases, which can eliminate the chiral parameter contribution to the transmission spectra. As shown in FIG. 36, the calculated spectra between molecules show the similar magnitudes, indicating that the microbubbles have near equal accumulation efficiencies for glucose and lactate. In another control experiment, the circular dichroism spectra shift for L-/D-lactate (concentration=100 μM) were measured (FIG. 37). The results indicate that the accumulation-assisted plasmonic chiral sensing can determine the chirality of a pure lactate solution with high accuracy (FIG. 37).

Figure 38:
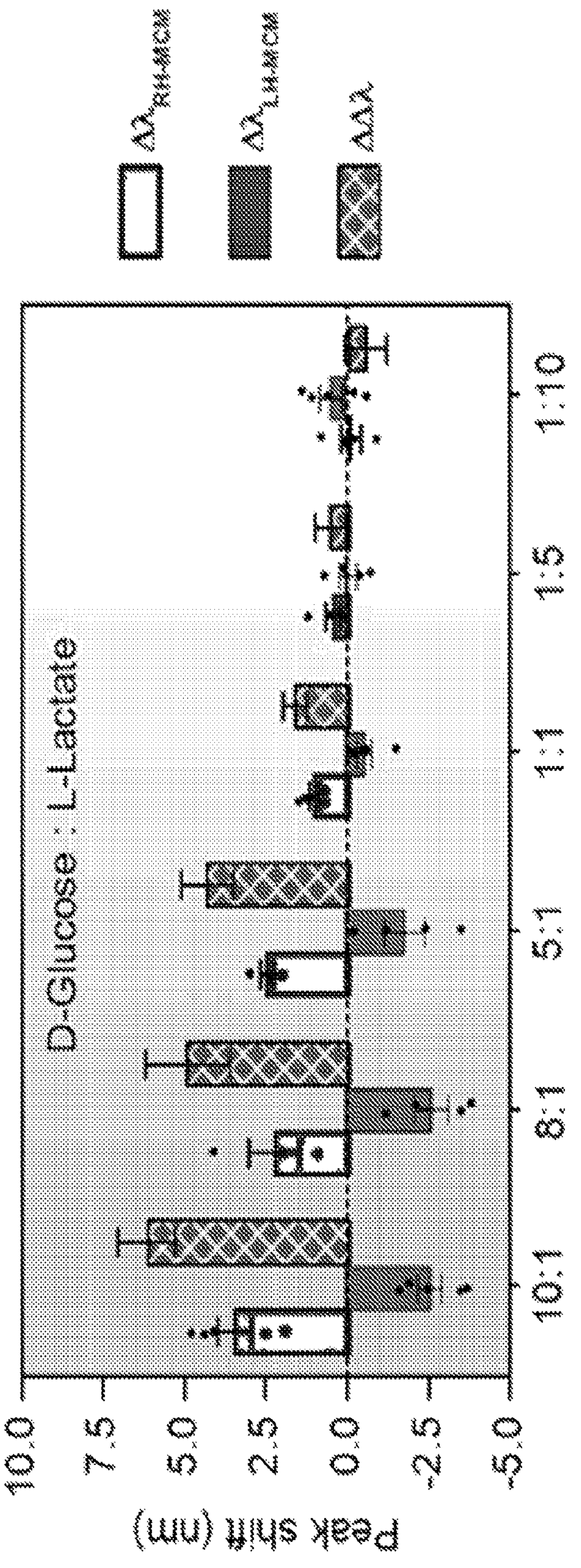
FIG. 38 is the circular dichroism spectral shifts (Δλ) and dissymmetry factors (ΔΔλ) at various ratios of D-glucose and L-lactate mixture solution with 100 μM total concentration. Error bars indicate mean=S.D. The bubble concentration time for the mixture solutions is 5 s.

The chirality of mixtures with different chiral biomolecules was further tested by measuring the dissymmetry factors of solutions with mixtures of D-glucose and L-lactate at various ratios. As shown in FIG. 38, the measured dissymmetry factor (ΔΔλ) gradually evolves from positive to negative as the ratio of D-glucose to L-lactate increases, matching with the gradual changes from dextrorotatory to levorotatory status in solution. The measured dissymmetry factors (ΔΔλ) have different absolute values between the 10:1 and 1:10 (D-glucose: L-lactate) cases. In addition, in contrast to the near zero value for the 1:1 mixture of D- and L-glucose solution, the dissymmetry factor (ΔΔλ) shows a positive value (~1.7 nm) in 1:1 mixture of D-glucose and L-lactate case. Such differences can be attributed to the different chiral parameters between glucose and lactate.

Figure 39:
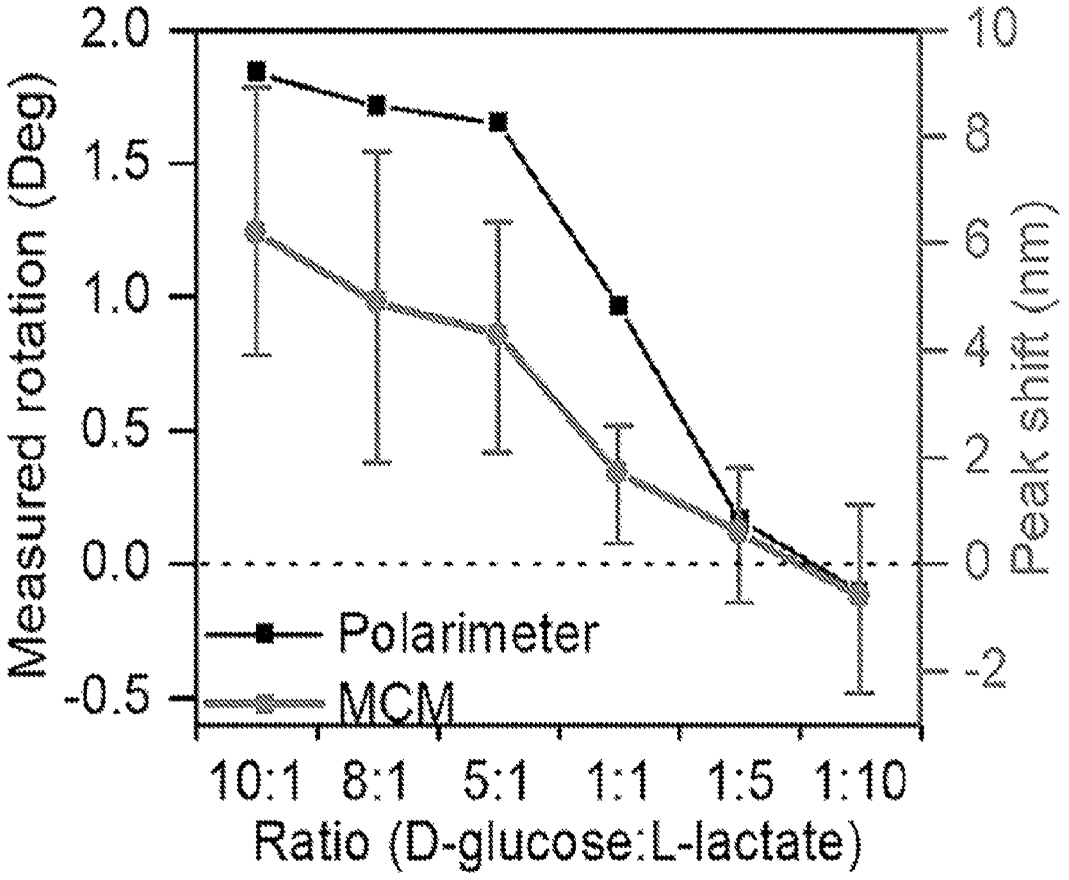
FIG. 39 is the comparison between ΔΔλ using moiré chiral metamaterial and measured optical rotation using Azzota Corp automatic polarimeter. To accurately measure the optical rotation, the total concentration of the mixture is adjusted to 100 mM and the cuvette length is 1 dm with total volume of ~10 mL.

Traditionally, chiral parameter ($\kappa_m$) in visible and near infrared range is estimated by fitting exponential decay function to the experimental Lorentzian distribution of UV-circular dichroism spectra, which becomes inaccurate when comparing chiral parameters between molecules (García-Guirado et al. *Nano letters* 2018, 18, 6279-6285; Lee et al. *ACS Photonics* 2017, 4, 2047-2052; Ben-Moshe et al. *Chemical Society Reviews* 2013, 42, 7028-7041). Herein, the optical rotation measurement was adopted using an Azzota Corp automatic polarimeter, which quantifies the $\mathrm{Re}(K\kappa_m)$ with high accuracy. As an example, by considering the cuvette length (1 dm) and the wavelength of incident light (589 nm), the calculated $\mathrm{Re}(K\kappa_m)$ for D-glucose and L-lactate mixture with 10:1 ratio is $+3.56\times10^{-6}$. As shown in FIG. 39, ΔΔλ shows high correlation with the measured optical rotation. Specifically, the measured rotation is nonzero for a mixture of D-glucose and L-lactate with a 1:1 ratio, which is caused by the larger absolute value of specific rotation of D-glucose than L-lactate (Heidelberger et al. *The Journal of experimental medicine* 1924, 40, 301; MacDonald et al. *Journal of the American Chemical Society* 1956, 78, 3720-3722). Since the resolution of commercial polarimeter is 0.005 Deg, the calculated detection limit is 100 μM with a total volume of ~10 mL. As a comparison, the technique described herein used 100 μM of the mixture with the total volume of ~10 μL, corresponding to three orders reduction in sample consumption. These findings also imply ΔΔλ can be an alternative method to quantify the magnitude of chiral parameters with high sensitivity, which is important for chirality detection in clinical trials.

Detection of Diabetes-Induced Abnormal Chirality

Abnormal chirality of metabolites in plasma, measured using a polarimeter, has proven promising as indicators for diabetes detection and diagnosis (Purvinis et al. *Journal of diabetes science and technology* 2011, 5, 380-387; Pirnstill et al. *Diabetes technology & therapeutics* 2012, 14, 819-827). However, sensing the chirality of metabolites in urine samples, which can be obtained by less intrusive approaches for development of potentially noninvasive point-of-care diagnosis, remains elusive due to the concentration of some important metabolites (such as glucose) being three orders of magnitude lower in urine than in plasma. The detection limit of conventional polarimeters was overcome using the accumulation-assisted plasmonic chiral sensor described herein, which benefits from the several orders of magnitude improvement in sensitivity, enabling the rapid determination of chirality of metabolites in urine with high accuracy.

Figure 40:
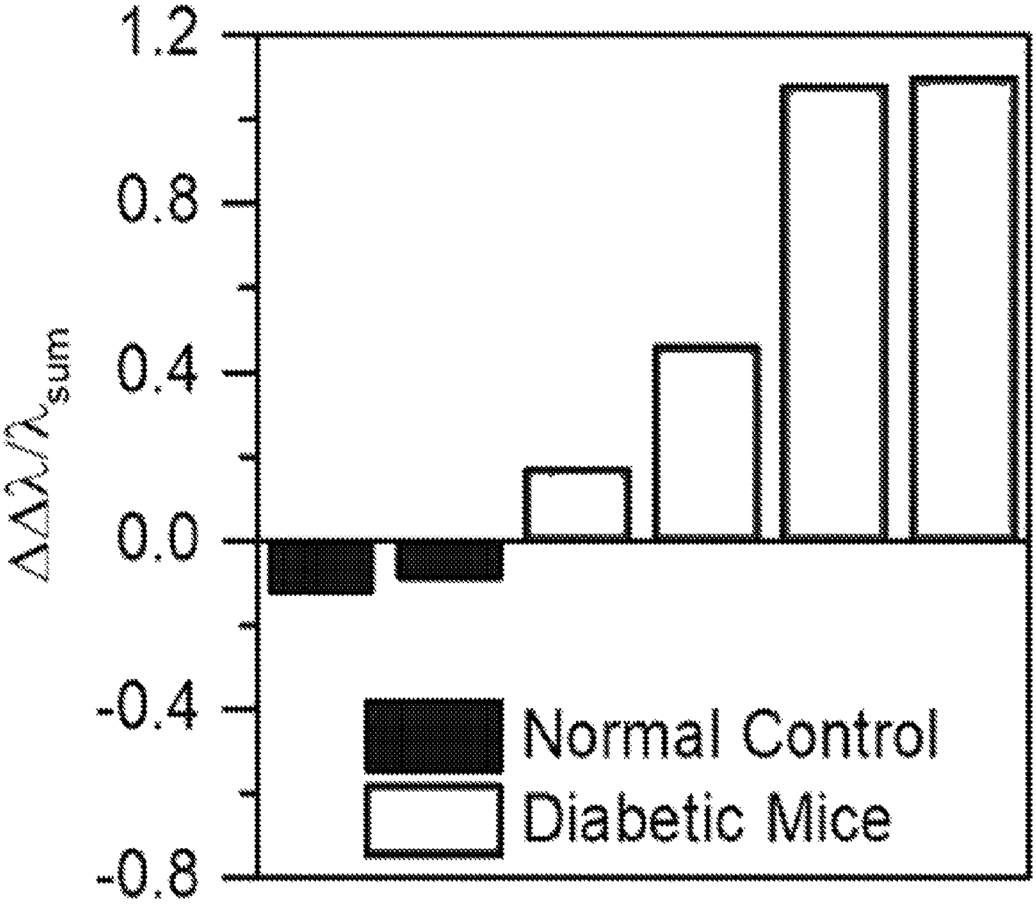
FIG. 40 is the normalized dissymmetry factors ($\Delta\Delta\lambda/\lambda_{sum}$) measured for urine samples from diabetic and normal mice. The bubble concentration time for the urine solutions is 5 s.
Figure 41:
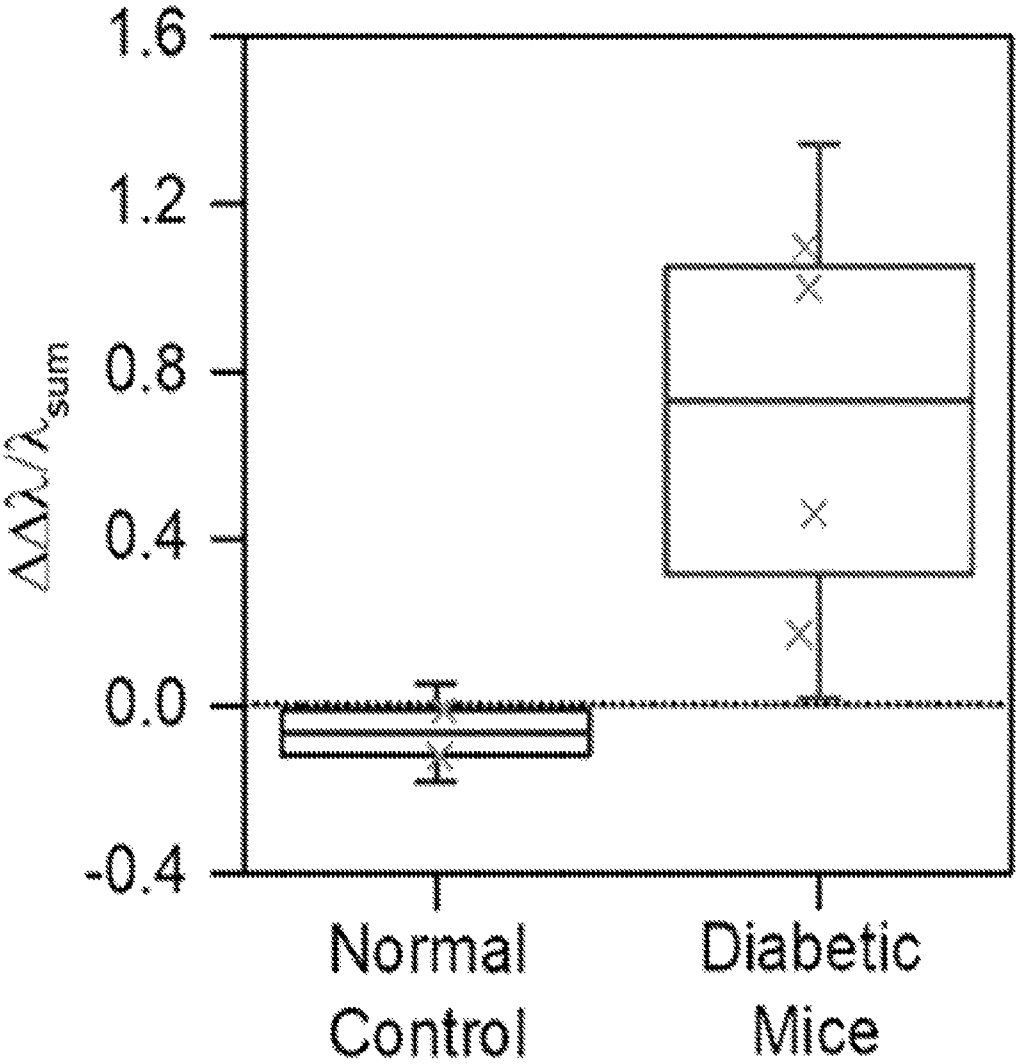
FIG. 41 is the normalized dissymmetry factors ($\Delta\Delta\lambda/\lambda_{sum}$) measured for urine samples from diabetic and normal mice. The median, upper, and lower quartiles are shown in the box. The whiskers represent the mean plus and minus 1.5×S.D. The bubble concentration time for the urine solutions is 5 s.
Figure 42:
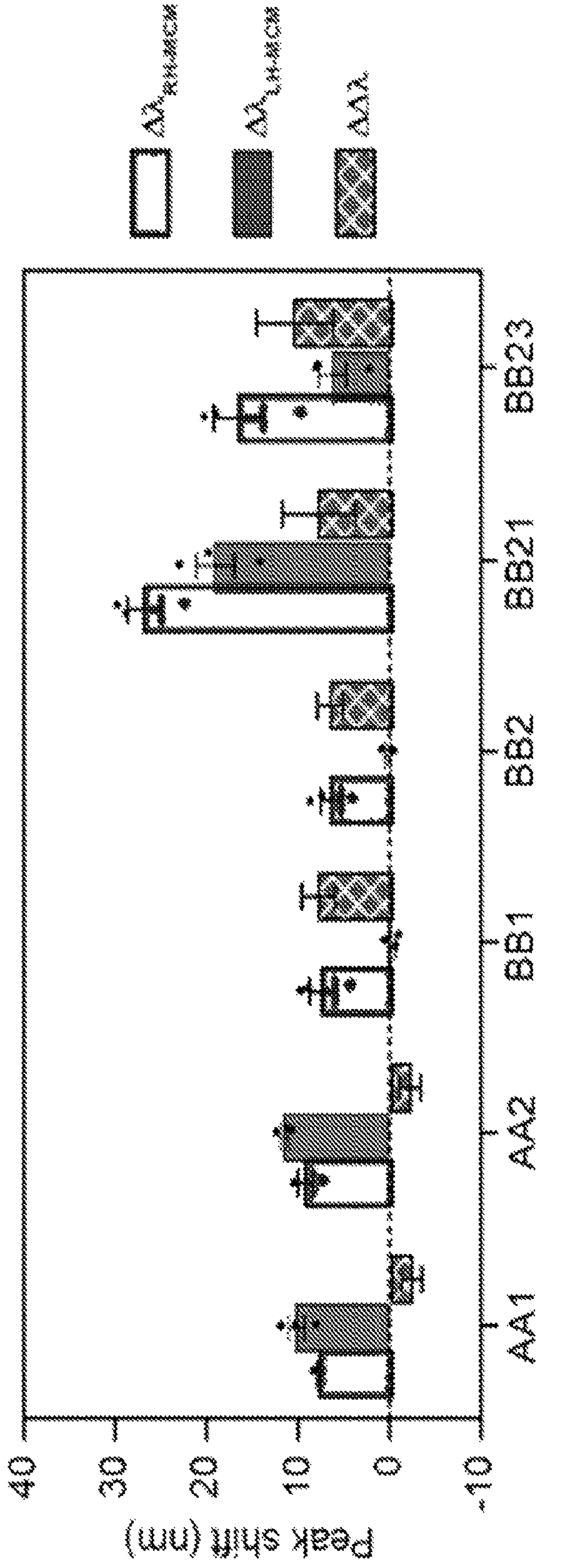
FIG. 42 is the circular dichroism spectral shifts (Δλ) and dissymmetry factors (ΔΔλ) for urine samples from normal and diabetic mice. Error bars indicate mean±S.D.

The effectiveness of this technique was first tested on urine samples collected from mice with and without diabetes. The protocols for preparing, collecting and purifying urine samples from mice are detailed above. The circular dichroism spectra shift and ΔΔλ were measured in urine samples from normal and diabetic mice after microbubble concentrations. As shown in FIG. 40 and FIG. 41 and FIG. 42, the normalized dissymmetry factors ($\Delta\Delta\lambda/\lambda_{sum}$) measured using the accumulation-assisted plasmonic chiral sensor have average values of −0.07 and 0.7 for urine samples collected from normal and diabetic mice, respectively.

Herein $\lambda_{sum}$ is the summation of $\Delta\lambda_{RH\text{-}MCM}$ and $\Delta\lambda_{LH\text{-}MCM}$, which reflects the total amount of printed molecules on the substrate. The negative value of AAN/$\lambda_{sum}$ for the control mice (e.g., without diabetes) indicates that normal urine is dominated by left-handed molecules such as L-lactates, L-amino acids and derivatives (Bouatra et al. *PloS one* 2013, 8, e73076).

The D-glucose and L-lactate concentration for each sample are shown in Table 1. The concentrations were measured using a biochemistry analyzer (YSI 2900), which utilizes the inherent specificity of enzyme reactions for multiple analytes detection through single measurement. Comparing the normalized dissymmetry factors to the concentrations of glucose and lactate obtained using the enzyme test (Table 1), the abnormal dextrorotary values in dissymmetry factors for samples from diabetic mice could be attributed to the diabetes-induced increase of D-glucose level in urine (Purvinis et al. *Journal of diabetes science and technology* 2011, 5, 380-387; Pirnstill et al. *Diabetes technology& therapeutics* 2012, 14, 819-827; Laksono et al. *IOP Conference Series: Materials Science and Engineering.* 012030, IOP Publishing). The large differences in the measured dissymmetry factors demonstrate the effectiveness of the accumulation-assisted plasmonic chiral sensors in monitoring the chirality changes in urine metabolites. The opposite signs and small overlaps in the measured dissymmetry factors also reveal the existence of diabetes-induced abnormal chirality in urine for mice.

TABLE 1

Measured D-glucose (Glu) and L-lactate (Lac) concentration between normal and diabetes mouse urine.

| Date | Control | Glu (mM) | Lac (mM) |
|---|---|---|---|
| Mar. 4, 2020 | AA1 | 1.85 | 22.9 |
| Mar. 4, 2020 | AA2 | 0.82 | 18.3 |
| Date | Diabetic | Glu (mM) | Lac (mM) |
| Mar. 4, 2020 | BB1 | 141.3 | 4.1 |
| Mar. 4, 2020 | BB2 | 140.9 | 1.9 |
| Mar. 4, 2020 | BB21 | 141.3 | 0.37 |
| Mar. 4, 2020 | BB23 | 140.5 | 0.29 |

Figure 43:
FIG. 43 is the circular dichroism spectral shifts (Δλ) and dissymmetry factors (ΔΔλ) for urine samples from normal (non-diabetic) humans. Error bars indicate mean±S.D.
Figure 43:
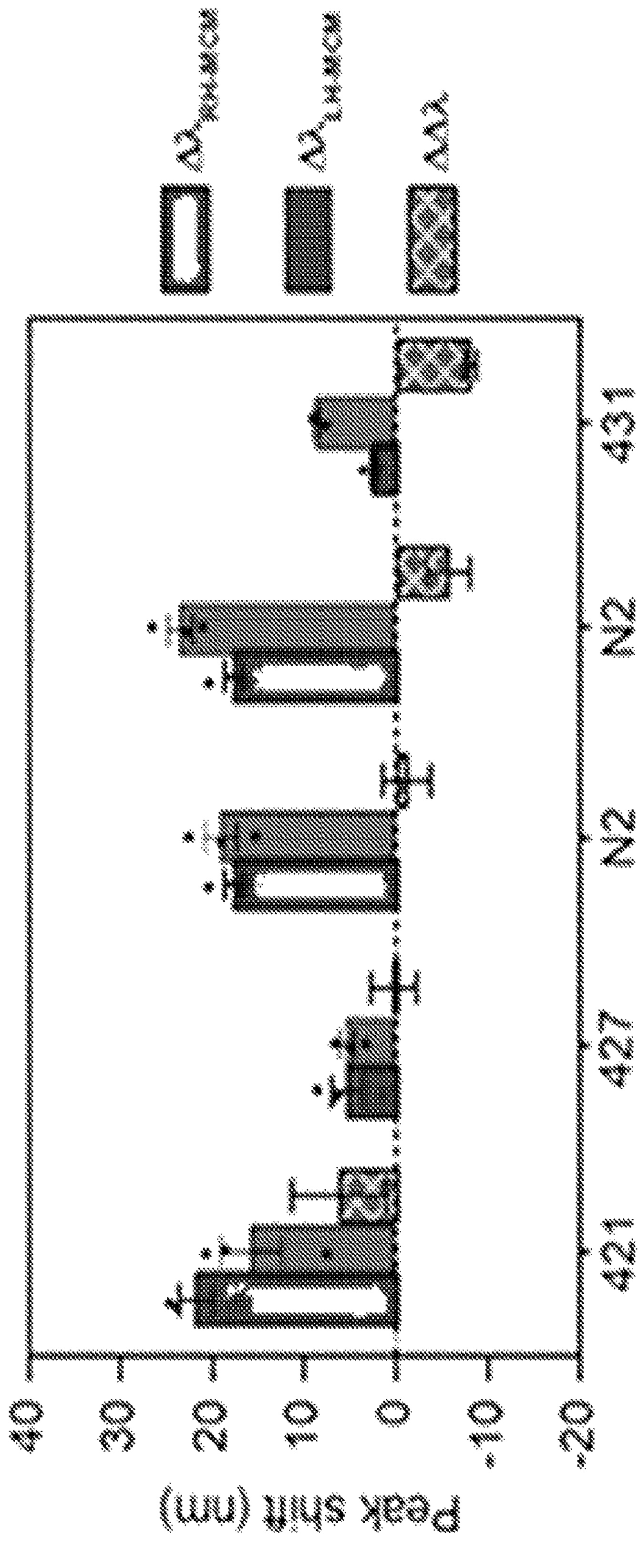
Figure 44:
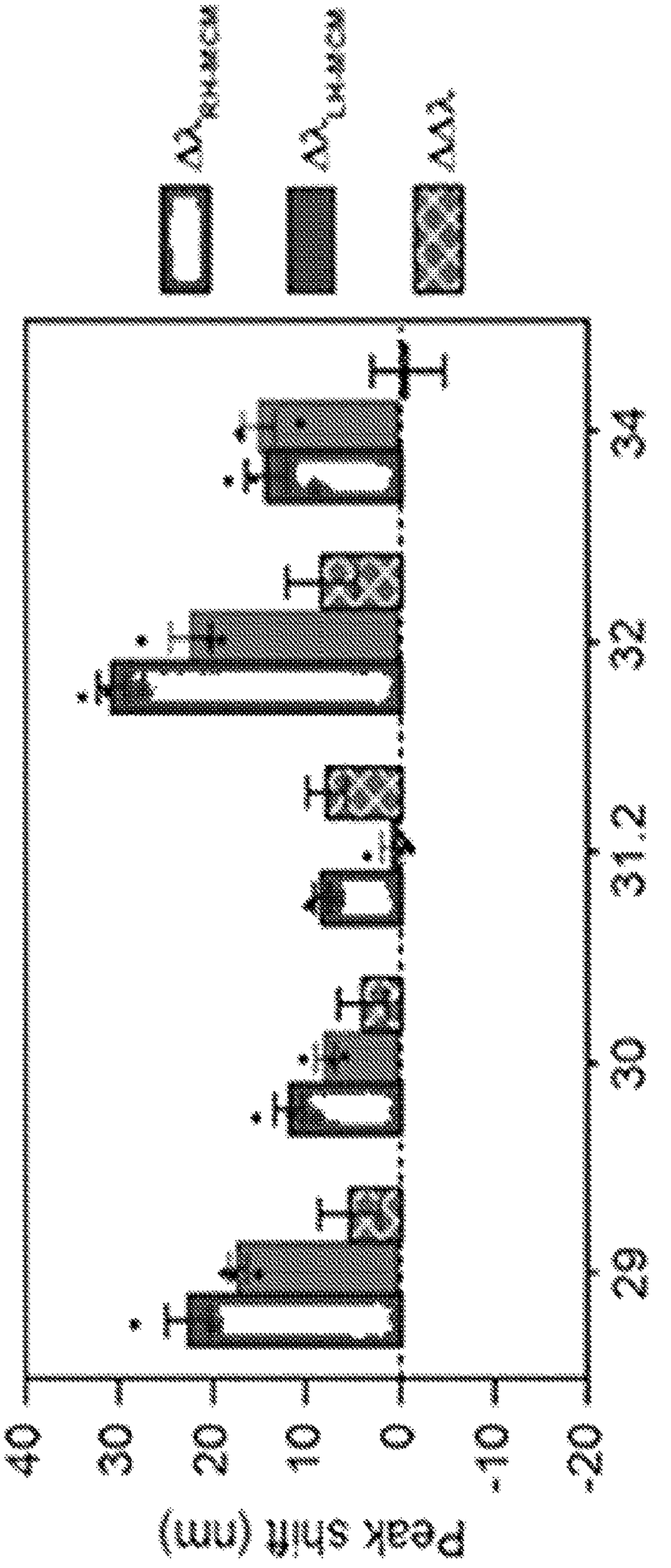
FIG. 44 is the circular dichroism spectral shifts (Δλ) and dissymmetry factors (ΔΔλ) for urine samples from diabetic humans. Error bars indicate mean±S.D.
Figure 44:
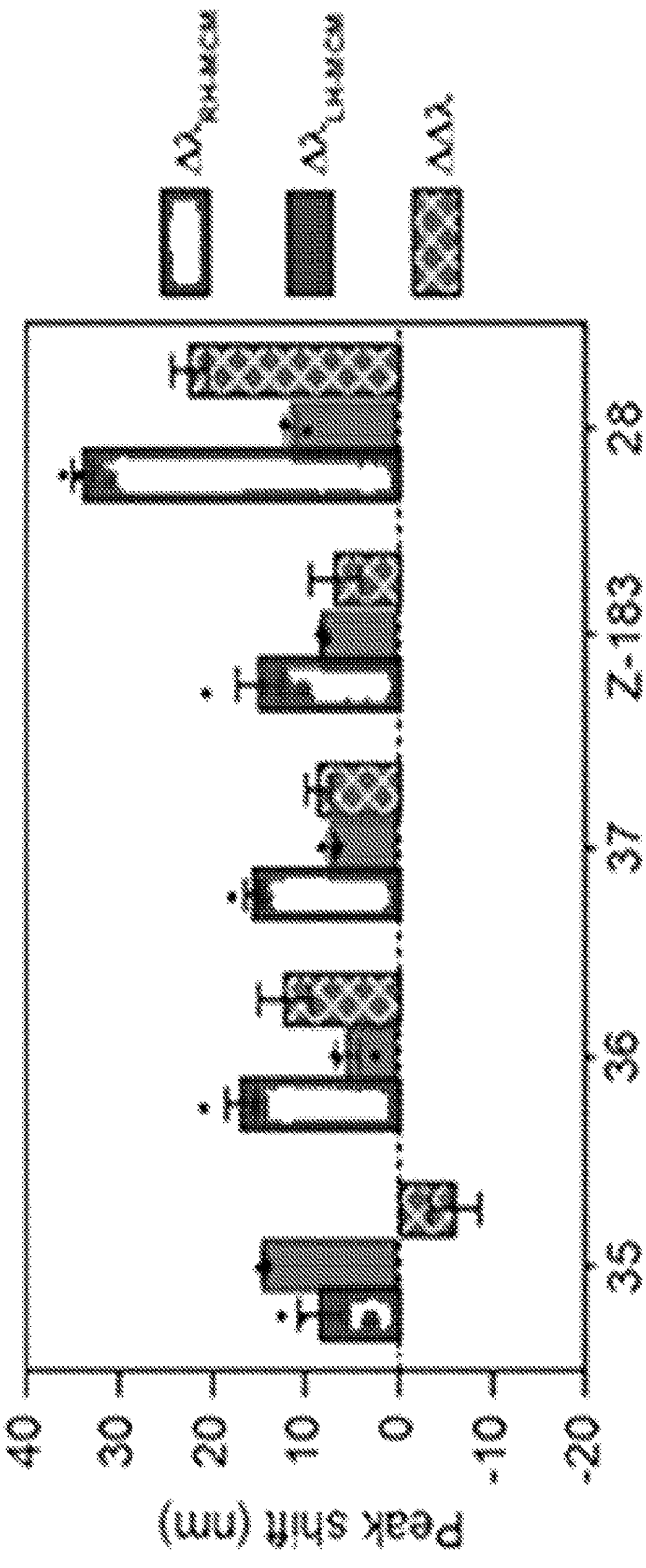
Figure 45:
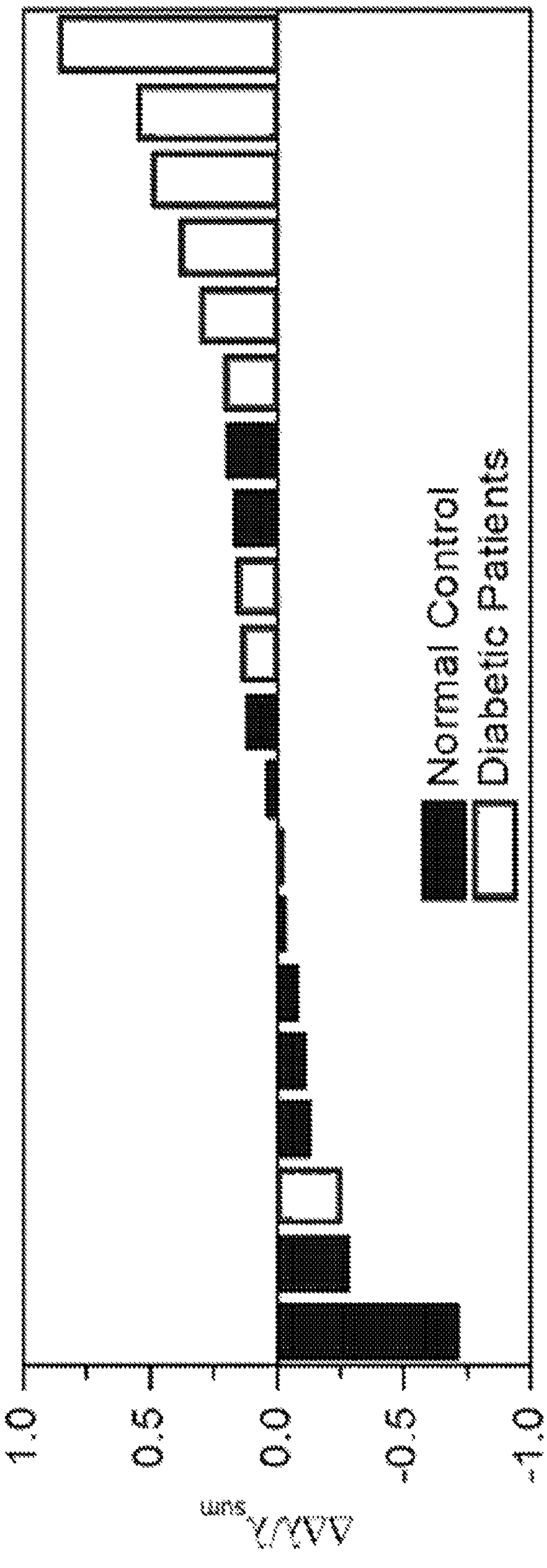
FIG. 45 is the normalized dissymmetry factors $(\Delta\lambda)/\lambda_{sum}$) measured for urine samples from normal and diabetic humans. The bubble concentration time for the urine solutions is 5 s.

The accumulation-assisted plasmonic chiral sensor was then used to analyze urine samples collected from nondiabetic human and diabetic human patients. The circular dichroism spectral shift and $\Delta\Delta\lambda$ of urine samples from 10 non-diabetic humans after microbubble concentration were measured (FIG. 43). The circular dichroism spectra shift and $\Delta\Delta\lambda$ of urine samples from 10 diabetic humans after microbubble concentrations were also measured (FIG. 44). The duration of the accumulation assisted concentration was 5 seconds for all cases. Similar to the mice, the values of normalized dissymmetry factors ($\Delta\Delta\lambda/\lambda_{sum}$) for the diabetic samples are overall more positive than those of the non-diabetic samples, as shown in FIG. 45.

Figure 46:
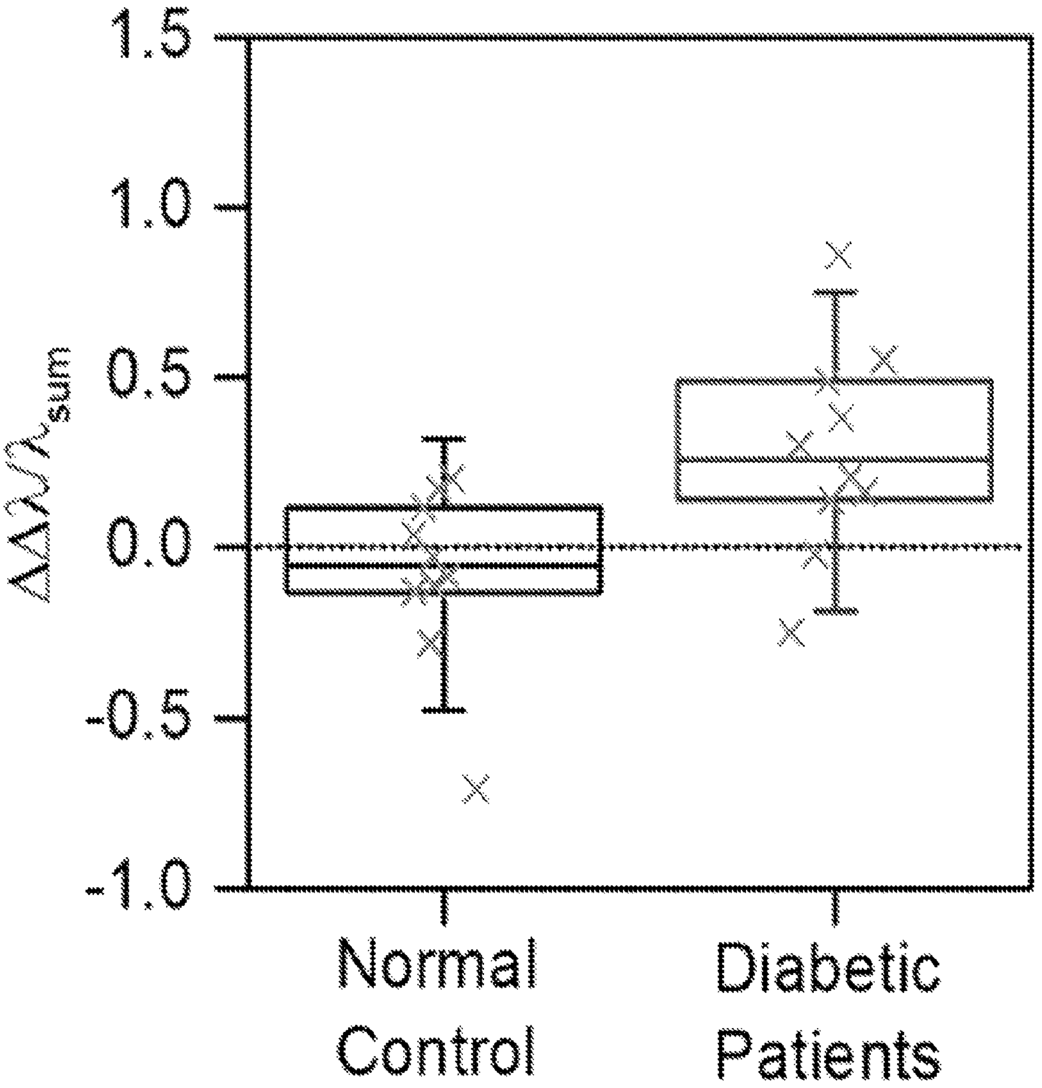
FIG. 46 is the normalized dissymmetry factors ($\Delta\Delta\lambda/\lambda_{sum}$) measured for urine samples from normal and diabetic humans. The median, upper, and lower quartiles are shown in the box. The whiskers represent the mean plus and minus 1.5×S.D. The bubble concentration time for the urine solutions is 5 s.

The glucose and lactate concentrations in the urine samples from both non-diabetic and diabetic humans were also measured using an enzyme test for comparison (Table 2 and Table 3). The level of these metabolites shows one order lower average values than those in urine from mice (Table 1). It will be difficult to accurately detect chirality changes via conventional label-free chiroptical methods (i.e. circular dichroism spectrometry and polarimeter) at such low levels of metabolite concentration. In comparison, despite the existence of small overlap in values, the good contrast in the normalized dissymmetry factors between normal and diabetic urine samples demonstrates the capability of the method described herein to uncover the otherwise hidden strong correlations between diabetes and abnormal chirality of metabolites in human urine, as shown in FIG. 46.

TABLE 2

Measured D-glucose (Glu) and L-lactate (Lac) levels in urine from non-diabetic humans.

| Control | Glu (mM) | Lac (mM) |
|---|---|---|
| 401 | 0.38 | 0.29 |
| 404 | 1.44 | 1.14 |
| 406 | 0.86 | 0.55 |
| 414 | 0 | 0.17 |
| 418 | 0.08 | 0 |
| 421 | 436.33 | 2.06 |
| 427 | 0 | 0.679 |
| N2 | 0.05 | 0.04 |
| N1 | 0.95 | 0.43 |
| 431 | 0 | 0 |

TABLE 3

Measured D-glucose (Glu) and L-lactate (Lac) levels in urine from diabetic humans.

| Diabetic | Glu (mM) | Lac (mM) |
|---|---|---|
| 29 | 10.22 | 0.09 |
| 30 | 8.04 | 0.10 |
| 31.2 | 57.93 | 0.08 |
| 32 | 0.39 | 0.13 |
| 34 | 0.40 | 0.04 |
| 35 | 13.34 | 1.22 |
| 36 | 0.28 | 0.05 |
| 37 | 1.16 | 0.04 |
| Z-183 | 1.06 | 0.08 |
| 28 | 0.02 | 0.01 |

Figure 47:
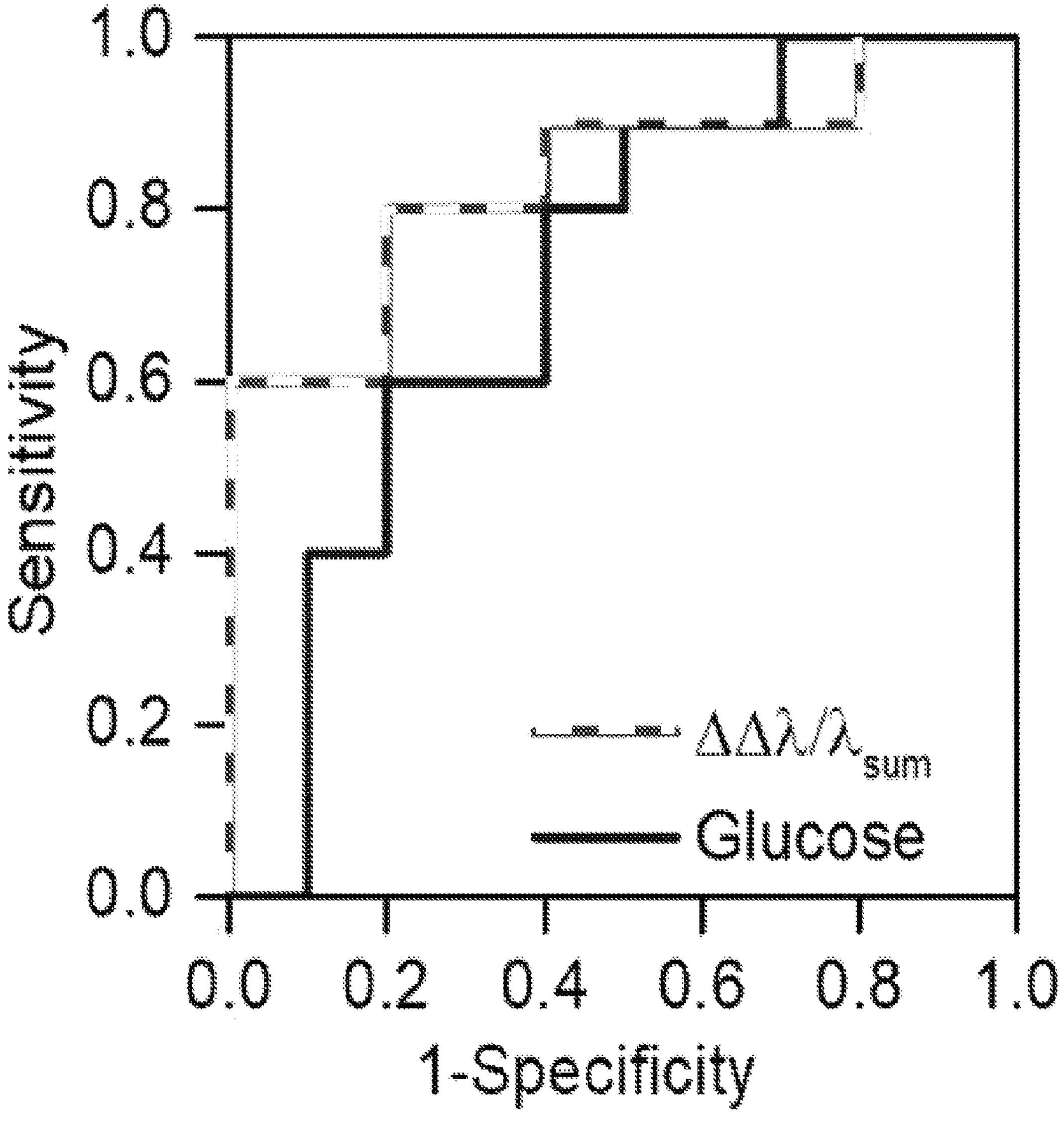
FIG. 47 is the receiver operating characteristic curves (ROC) of $\Delta\Delta\lambda/\lambda_{sum}$ and glucose concentration. The bubble concentration time for the urine solutions is 5 s.

Receiver operating characteristic (ROC) analysis was further conducted by calculating the area under the curve (AUC) values to determine the diagnostic accuracy. The AUC value obtained using the accumulation-assisted plasmonic chiral sensor based on $\Delta\Delta\lambda/\lambda_{sm}$ is 84%, as shown in FIG. 47, demonstrating the potential of this technique in noninvasive diagnostic applications. In comparison, the AUC value is 72% in the same cohort for enzyme tests of glucose in urine, which is a standard biomarker for conventional diabetes examination. The higher AUC value of the accumulation-assisted plasmonic chiral sensor approach shows that the existence of abnormal chirality in urine metabolites, which reflects the overall chiral changes of metabolic molecules, could be more accurate as markers than elevated glucose concentration in urine for the screening of diabetes and diabetes-related complications. The higher AUC value from the chirality analysis than that from the glucose concentration test indicates the possible abnormal changes of other chiral metabolic molecules (i.e. carboxylic acids and amino acids) besides glucose in diabetic human urine.

Figure 48:
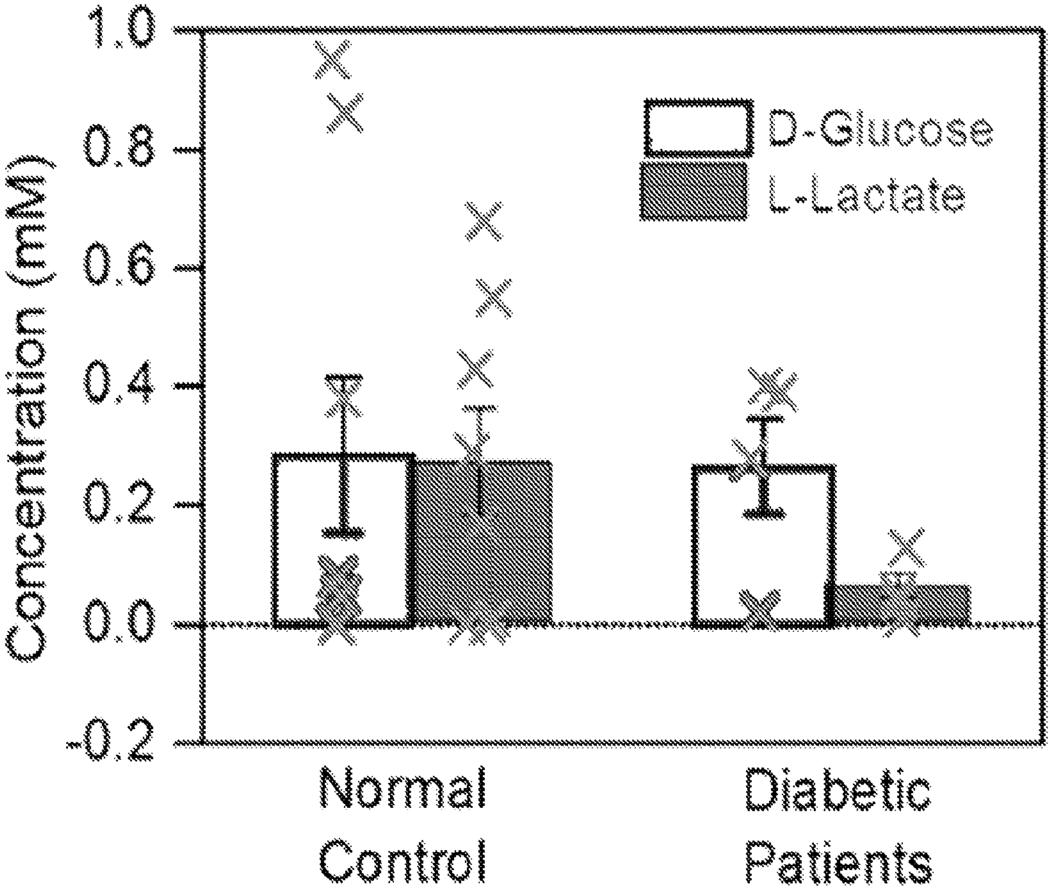
FIG. 48 is the concentration of D-glucose and L-lactate between normal control and diabetic patients in the selected group. Error bars indicate mean±S.D.

Urine solutions with D-glucoses level less than 1 mM from for normal (non-diabetic) control and diabetic patients were selected and the concentration of both D-glucose and L-lactate levels in these samples were then compared. As shown in FIG. 48, the diabetic patients in this group have lower urinary L-lactate concentrations than the normal controls. Considering the well-studied increase of D-lactate in diabetes patients (Talasniemi et al. *Clinical biochemistry* 2008, 41, 1099-1103; Christopher et al. *Metabolism* 1995, 44, 287-290; Chou et al. *Journal of pharmaceutical and biomedical analysis* 2015, 116, 65-70; Kondoh et al. *Research in experimental medicine* 1992, 192, 407-414), it can be hypothesize that the abnormal changes of D- to L-lactate ratio could contribute to the more dextrorotary values in total chirality in diabetic patients over normal controls in this study. Therefore, the diagnostic accuracy is improved using the accumulation-assisted plasmonic chiral sensor than using glucose enzymes, especially when controls and diabetics have similar glucose levels. The abnormal levels of chiral amino acids in diabetics, which have been observed in plasma and nails but less studied in urine, could also contribute to the changes in total chirality (Kimura et al. *Scientific reports* 2016, 6, 26137; Lorenzo et al. *Journal of pharmaceutical and biomedical analysis* 2015, 107, 480-487; Min et al. *Journal of Chromatography B* 2011, 879, 3220-3228). These results point out the need for more studies on correlations between diabetes and abnormal chiral changes of other metabolic molecules besides glucose in urine, which may be useful for better understanding and noninvasive diagnosis of diabetes and its complications (Sasabe et al. *The Keio journal of medicine* 2018; Hamase et al. *Journal of chromatography B* 2002, 781, 73-91).

DISCUSSION

In summary, an accumulation-assisted plasmonic chiral sensing was developed to achieve ultra-sensitive, rapid, and label-free chirality detection of diabetes-related metabolic molecules. The optothermally generated microbubbles create strong Marangoni convection, enabling large drag forces on metabolic molecules with small molar masses towards the plasmonic chiral metamaterial substrates. The dense occupation of accumulated molecules at the plasmonic hot spots of the metamaterials enables label-free chiral detection of glucose down to 100 pM. The detection and monitoring of ratio-dependent chirality changes in mixtures of various metabolic molecules with high sensitivity and accuracy, while requiring three orders less sample consumption (~10 μL) than commercial chiroptical techniques, was also achieved. Benefiting from the ultra-high sensitivity and low sample consumption, the accumulation-assisted plasmonic chiral sensing has revealed the typically hidden diabetes-induced abnormal chirality of metabolites in urine samples collected from mice and humans. The ROC analysis of the accumulation-assisted plasmonic chiral sensing technique further shows a higher diagnostic accuracy of 84% in comparison with 72% from enzyme tests of glucose level for human urine samples. These results reveal the crucial roles of abnormal chirality of urine metabolites in both fundamental and diagnostic studies of diabetes in the future. With the high cost-effectiveness and short characterization time (<1 min), the accumulation-assisted plasmonic chiral sensing shows great potential in development of point-of-care devices for first-line noninvasive screening and prognosis of early-stage pre-diabetes or diabetes and its complications. More detailed chiral analysis can be enabled using the accumulation-assisted plasmonic chiral sensing technique by enhancing the specificity via improved filtering or integration of microfluidic-based separation techniques. As chiral molecules have been found to be altered in several cancers as well (Bitbol et al. *Proceedings of the National Academy of Sciences* 1988, 85, 6783-6787), a routine chiral detection that is sensitive and non-invasive could also be used for detecting occult malignancies based on human urine testing.

Example 2

Circular dichroism refers to the differential absorption of left and right circularly polarized light and is exhibited in the absorption bands of optically active chiral molecules. As used herein, a chiral molecule is any molecule that has a non-superposable mirror image. The symmetry of a molecule (or any other object) determines whether it is chiral. The two mirror images of a chiral molecule are called enantiomers, or optical isomers. Human hands are perhaps one of the most recognized examples of chirality: the left hand is a non-superposable mirror image of the right hand. Indeed, the term "chirality" is derived from the Greek word for hand, and pairs of enantiomers are often designated by their "handedness" (e.g., right-handed or left-handed). Enantiomers, a pair of chiral isomers with opposite handedness, often exhibit similar physical and chemical properties due to their identical functional groups and composition. However, enantiomers behave different in the presence of other chiral molecules or objects, such as circularly polarized light.

An enantiomer can be named by the direction which it rotates the plane of polarized light. If the enantiomer rotates the light clockwise (as seen by a viewer towards whom the light is traveling), that enantiomer is labeled (+). Its mirror-image is labeled (−) and rotates the light counterclockwise.

Many naturally occurring biomolecules, such as nucleotides, sugars, and amino acids, are chiral. Their enantiomers often exhibit similar physical and chemical properties due to their identical functional groups and composition, yet they can show different pharmacological effects, such as different potency and toxicity, since they bind differently to the receptors of various biological organisms. In the case of chiral drugs, in some examples only one enantiomer produces the desired pharmacological effect, while the other enantiomer can be less active or merely inactive. In some cases, the other enantiomer can produce unwanted side effects. The most famous example of the difference in pharmacological effect of different enantiomers of chiral drugs is thalidomide. Detecting enantiomers of different chirality in small quantities can play an important role in drug development, for example to eliminate unwanted side effects.

Further, abnormal concentration of chiral molecules has been observed in human bodies with increasing age and various chronic diseases such as Alzheimer's disease, chronic kidney disease, and diabetes, indicating the potential of applying chiral biomarkers as health indicators for diagnostic and prognostic applications.

For example, the case fatality rate of subjects with COVID-19 was higher for subjects with underlying health conditions, such as cardiovascular disease, diabetes, chronic respiratory disease, hypertension, and cancer. Thus, detecting the presence of these underlying health conditions is useful for the prognosis of a patient with COVID-19.

Further, as of 2010, 25.8 million children and adults in the US have diabetes (8.3% of the population). Of these 25.8 million, it is estimated that 7.0 million are thus far undiagnosed as diabetic. It is further estimated that 79 million children and adults in the US are prediabetic. In 2010, 1.9 million new cases of diabetes were diagnosed in people aged 20 years and older.

Humans with diabetes show abnormal levels of chirality for various components. In particular, elevated levels of many D-type metabolic molecules in urine have shown strong correlation with diabetic mellitus. For example, the levels of D-glucose, D-Alanine, D-Proline, D-Valine, D-Isoleucine, D-Leucine, D-Asparagine, S-Serine, and D-Lactate have been found to be elevated in human subjects with diabetes (Handbook of optical sensing of glucose in biological fluids and tissues, 2008, 12; Journal of Chromatography V, 2011, 879, 3220-3228; Anal. Chem. 2019, 91 (19), 11569-11575; Anal. Bioanal. Chem. 2015, 407(3), 1003-14).

Conventional methods for chiroptical detection include circular dichroism spectroscopy, polarimetry, chiral liquid/gas chromatography, and fluorometric assay kits. These conventional methods suffer from one or more of the following limitations: high sample volume required, high analyte concentration required, tedious preparation steps required (e.g., chiral derivatizing agents or chital stationary phase), long detection/analysis times, and expensive, complicated, and/or cumbersome equipment.

Various plasmonic chiral sensors have been developed for chiroptical detection, including metallic metasurfaces and self-assembled nanoparticles, and (Nat. Nano. 2010, 5, 783-787; Science, 2019, 365(6460), 1475-1478). State-of-the-art chiral sensors are described, for example, in ACS Photonics 2020, 7(1), 36-42. An advantage of plasmonic chiral sensors for chiroptical detection is that they can significantly reduce the sample volume and analyte quantity required (e.g., single molecule or few molecule detection limit). The concentration of analytes before these measurements can be high (>1 mM). Many of these plasmonic chiral sensors have been developed as proof-of-concept devices, and could be used in various life science applications.

Bubble pen lithography has been previously described for printing polystyrene beads (~5 μm), quantum dots (~30 nm), and metallic ions (~1 nm) (Nano Lett. 2016, 16, 701-708; Matter 2019, 1(6), 1606-1617). The bubble generated in these systems significantly impacts the convection present in the liquid sample (FIG. 18 vs. FIG. 19). It is hypothesized herein that bubble pen lithography can be further adapted to print and concentrate biomolecules for biosensing.

Figure 49:
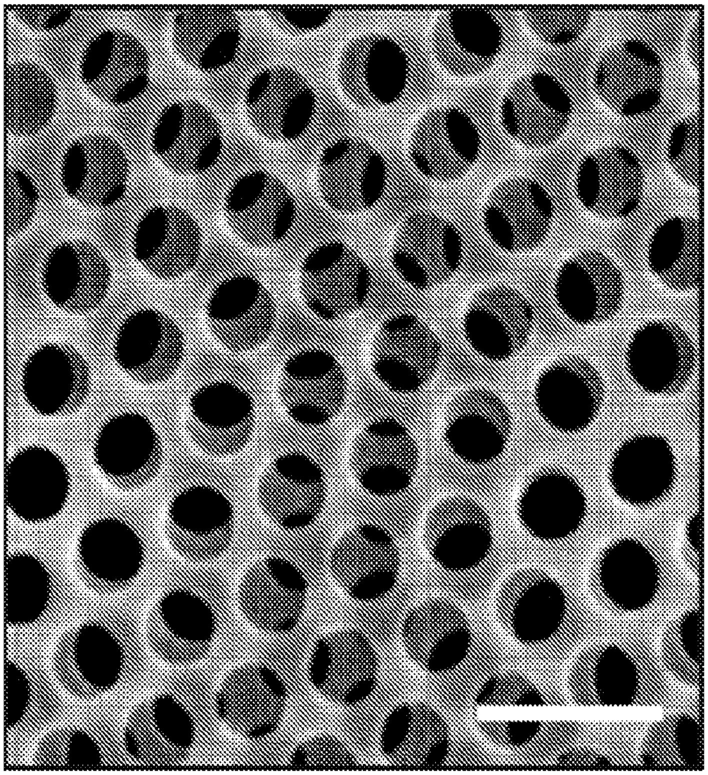
FIG. 49 is a scanning electron microscopy image of an example left-handed moiré chiral metamaterial.
Figure 50:
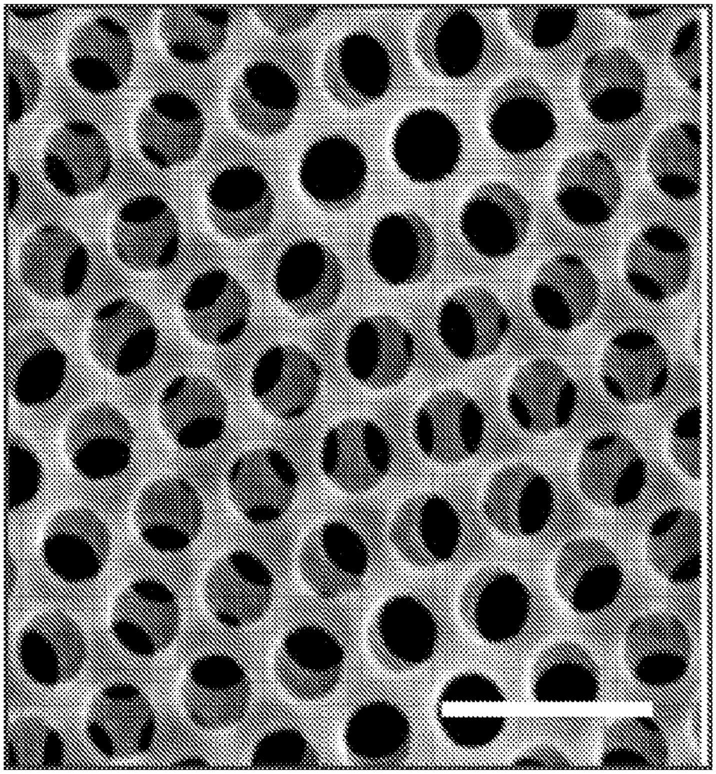
FIG. 50 is a scanning electron microscopy images of an example right-handed moiré chiral metamaterial.

Accordingly, microbubble-assisted concentration of biomolecules using plasmonic chiral metamaterials was investigated. FIG. 17 is a schematic illustration of the collection and purification of urine samples, and the microbubble-enabled accumulation of chiral metabolic molecules on moiré chiral metamaterials for enhanced chiral sensing and diabetic detection via asymmetric spectral shifts. As shown in FIG. 17, the irradiation of a focused laser on to the moiré chiral metamaterials induced plasmon-enhanced optical heating at the laser focus point, vaporizing the solution above the substrate and generating a microbubble. The microbubble-induced Marangoni convection can effectively drag biomolecules in the solution towards the laser spot (FIG. 19). Scanning electron microscopy images of an example left-handed moiré chiral metamaterial and an example right-handed moiré chiral metamaterial are shown in FIG. 49 and FIG. 50, respectively. The superchiral fields of the moiré chiral metamaterials under left-handed circularly polarized excitation and right-handed circularly polarized excitation (FIG. 23 and FIG. 24 respectively) are comparable to state-of the art plasmonic chiral sensors.

The microbubble-induced accumulation method using the moiré chiral metamaterials was used to determine the chirality of ultrasmall metabolites (FIG. 29 and FIG. 30). The microbubble-induced accumulation method shows ~$10^7$ times enhancement in sensitivity compared to state-of-the-art plasmonic chiral sensors (FIG. 33 and FIG. 34). The microbubble-induced accumulation method shows results that match well with traditional polarimeter measurements while having a three order of magnitude improvement in sample consumption (FIG. 38 and FIG. 39).

The microbubble-induced accumulation method using the moiré chiral metamaterials was used to detect diabetes-induced abnormal chirality; the results indicated that diabetic patients shows more dextrorotatory properties and the method had a diagnostic accuracy of 84% (FIG. 45-FIG. 47).

Accordingly, the microbubble-assisted concentration of chiral metabolites using plasmonic chiral metamaterials was demonstrated, which exhibited 7 orders of magnitude enhancement in sensitivity. Diabetes-induced abnormal chirality of metabolites in human urine was observed with a detection accuracy of 84%. These results and devices can benefit the development of point-of-care devices for non-invasive screening of diabetes.

Example 3

Described herein are point-of-care devices, which, for example, can be used for rapid label-free analysis of chiral metabolite biomarkers in human urine for early disease diagnosis.

Described herein is a point-of-care device that can provide detailed information on chemical composition and chirality of metabolite biomarkers in urine. With the microbubble-assisted concentration technique integrated with chiroptical spectroscopy on a chip, label-free enantiodiscrimination of biomolecules at picomolar level was achieved, corresponding to ~$\mathbf{10}^7$ enhancement in comparison with state-of-the-art sensitivity, which is important for the point-of-care applications.

This technique includes rapid molecular preconcentration and label-free chiral detection for metabolite biomarkers in human urines. The rapid preconcentration of the analytes before the measurement enhances the detection throughput and sensitivity.

In contrast, conventional technologies, rely on diffusion-based molecular interactions with chiral plasmonic sensor, which limits the plasmon-enhanced chiral sensing for samples with low concentration and racemic composition, hindering the ultrasensitive determination of chiral purity for stereochemistry study. When the molecule is closer to the substrate, interaction such as electrostatic, van Der Waals, and depletion forces between different molecule and substrate dominate, which will affect the amount of molecule near the substrate. Besides diffusion-based sensing, conventional preconcentration-assisted sensing methods, including thermoelectric, thermophoretic, and/or electrothermoplasmonic assisted sensing, have been demonstrated for applications in cells, DNA, and protein. However, it is challenging to achieve preconcentration for metabolites and small molecules due to their relatively small size and polar properties.

Herein, a bubble preconcentration method is used to concentrate multiple urine carbohydrates ultrametabolites to electrical field/local super chiral field hot spots for chiral molecule sensing. The stagnation area of Marangoni convection forces during the bubble formation can effectively print the molecules into micro-size areas on the substrate with high binding affinities, therefore breaking the limitation of traditional preconcentration methods. It is shown that this method can detect and differentiate 100 pM D/L pure glucose solution within 1 minute, which shows $10^7$ times greater sensitivity than the state-of-the-art chiral sensing techniques. Furthermore, by mixing different D-glucose/L-lactate and mimicking artificial urine solutions, their enantiomeric excess was successfully differentiated, which matches well with standard polarimeter measurement.

The devices described herein solves the problem of analyzing chirality of metabolite biomarkers in urine in a label-free and rapid manner, enabling its use for point-of-care disease diagnosis. The devices can enable use of ultralow concentrations because of the ultrafast preconcentration for label-free enantiodiscrimination of chiral molecules. Moreover, the enantiodiscriminative study of human urine solution with ultralow specific rotation was achieved, benefiting studies and rapid diagnosis of diseases such as type-II diabetes and diabetic complications, such as diabetic kidney disease.

The systems, devices, and methods described herein exhibit much quicker and more sensitive chiral sensing for biomarkers in urine for practical point-of-care applications. The first-ever label free enantiomeric excess measurement was conducted in human urine solution using the systems, devices, and methods using chiral plasmonic metamaterials described herein, which is challenging to detect using current techniques due to ultra-small optical rotation.

The microbubble-assisted concentration can generate highly localized temperature near the laser spot. This requires that the molecule should withstand these temperatures without denaturalizing, which might limit its application for complex biopsies such as DNA, protein and cells. However, this limitation can be overcome by reducing the boiling temperature of the solvent for wide applications, for example by controlling the chamber pressure or replacing the solvent with lower boiling temperature without losing Marangoni convection.

The point-of-care devices described herein can also be applied to blood and sweat for the chiral analysis of biomarkers for variable disease diagnosis and human wellness monitoring. In addition, the microbubble-assisted rapid concentration with ultrahigh sensitivity can detect chiral purity of solution, which might help pharmaceutical companies rapidly determine the chiral purity of drug-related molecules with low sample consumption.

Example 4

Conventional diagnosis of diabetes is conducted by testing D-glucose concentration in plasma or urine. However, recent studies show that many more chiral urine metabolites are also important clinical biomarkers for the disease. High L-lactate concentration in urine contributes to a large insulin resistant status and therefore promotes progression. Furthermore, an elevated D-lactate level in human urine is a sign of short bowel syndrome or diabetic ketoacidosis. Therefore, it is can be important to monitor both chemical composition and chirality of biomarkers for clinical purposes. However, current methods to achieve such clinical detection are either time-consuming or require large amounts of body fluids. The complexity and high cost of existing devices also hinder point-of-care clinical monitoring.

Accurate clinical sensing for human urine requires the detection of both chemical composition and molecular chirality of biomarkers. The three common sensing methods in clinical applications include: chiral mass-spectrometry chromatography, Chiral spectrometry/polarimetry, and fluorometric assays, Chiral mass-spectrometry chromatography allows for the separation of biomarkers based on molecular compositions or structural chirality. However, the chromatography requires specific chiral derivatization reagent for each chiral biomarker to achieve enantioselective separation, resulting in time-consuming and expensive processes to develop reagents, which should be avoided in point-of-care clinical applications.

Chiral spectrometry/polarimetry spectroscopic techniques do not require reagents, enabling cost-effective chiral detection. However, conventional spectroscopic techniques require high volume and high concentration of clinical samples. Furthermore, extra steps are required to determine the composition of the biomarkers.

Sensing is achieved in fluorometric assay kits by chirality- and composition-dependent reactions of biomarkers with specific enzymes. The major challenge for this technique is the lack of enzymes for some crucial biomarkers. It is also time-consuming and requires high volumes of analytes.

The sensors described herein can solve the current limitations by offering convenient, ultra-fast (<1 min) and ultra-sensitive (~100 pM) sensing of biomarkers on both composition and chirality.

Plasmonic chiral metamaterials with strong superchiral fields have proven to be promising to enhance light-matter interactions of chiral molecules for chirality determination. However, the extreme localization of superchiral fields and the diffusion-based molecular interactions with chiral hot spots have limited the plasmon-enhanced chiral sensing for samples with low concentration and racemic composition, hindering the ultrasensitive determination of chiral purity for stereochemistry study.

Herein, the microbubble-assisted concentration of analytes towards chiral hot spots in plasmonic metamaterials is demonstrated, enabling the label-free enantiodiscrimination of biomolecules at picomolar level, which is ~$10^7$ enhancement in comparison with state-of-the-art sensitivity. The ultrasensitive enantiodiscrimination allows the rapid determination of chiral purity of racemic solution with low concentration. Furthermore, the enantiodiscriminative study of human urine solution with ultralow specific rotation was achieved, benefiting studies and rapid diagnosis of diseases such as type-II diabetes and diabetic complications The systems, devices, and methods described herein can be used for label-free rapid enantiodiscrimination of metabolite biomarkers in urine with ultra-high sensitivity. The systems, devices, and methods described herein can exhibit ~$10^7$ enhancement in comparison with state-of-the-art sensitivity.

The systems, devices, and methods described herein are workable for small-quantity analytes; can be used for point-of-care devices for portable and home use; and can be used for early disease diagnosis, including diabetes diagnosis.

The systems, devices, and methods described herein can be used in applications of interest in hospitals and clinics. The systems, devices, and methods described herein can be used in applications of interest by doctors, patients, and pharmaceutical companies.

Example 5

Figure 51:
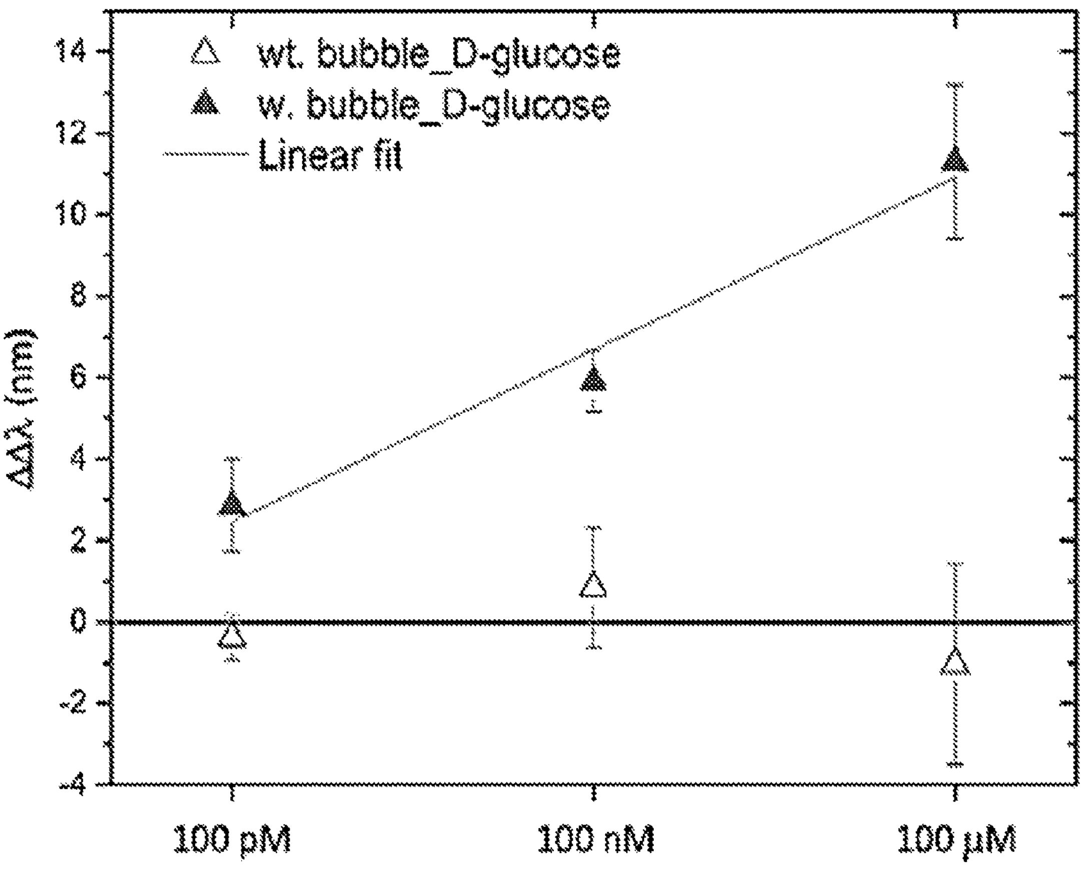
FIG. 51 is a plot of the measured ΔΔλ values of D-glucose aqueous solutions using moiré chiral metamaterials (MCMs) with and without microbubble-assisted accumulation. Sensing cannot be achieved without microbubble in the 100 μM to 100 mM regime. In contrast, sensing can be achieved with microbubble in the same concentration regime.

FIG. 51 is a plot of the measured $\Delta\Delta\lambda$ values of D-glucose aqueous solutions using moiré chiral metamaterials (MCMs) with and without microbubble-assisted accumulation. Sensing cannot be achieved without microbubble in the 100 μM to 100 mM regime. In contrast, sensing can be achieved with microbubble in the same concentration regime.

Figure 52:
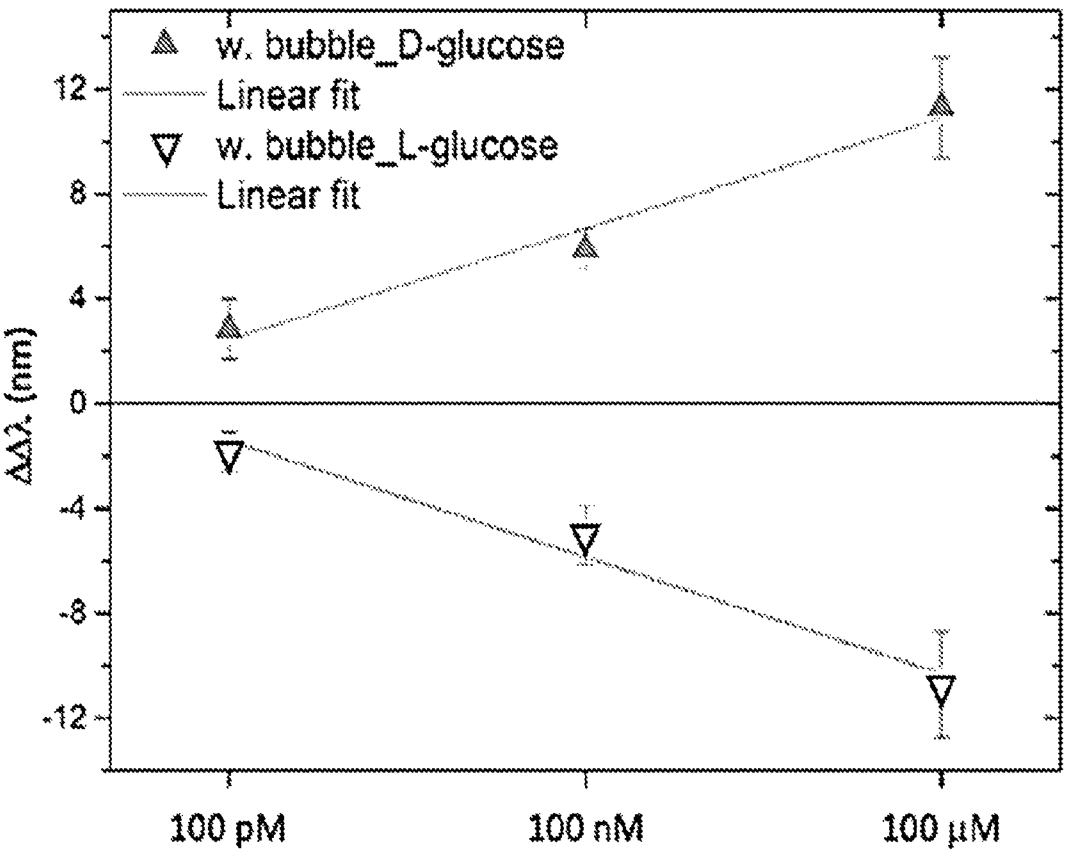
FIG. 52 is a plot of the measured ΔΔλ values of D-glucose and L-glucose aqueous solutions using moiré chiral metamaterials (MCMs) with microbubble-assisted accumulation. The corresponding linear fitting parameters are shown in Table 4.

FIG. 52 is a plot of the measured $\Delta\Delta\lambda$ values of D-glucose and L-glucose aqueous solutions using moiré chiral metamaterials (MCMs) with microbubble-assisted accumulation. The corresponding linear fitting parameters are shown in Table 4.

TABLE 4

Linear fitting parameters for FIG. 52.

| | Intercept | | Slope | | Statistics |
|---|---|---|---|---|---|
| | Value | Standard Error | Value | Standard Error | Adj. R-square |
| D-glucose | 1.05 | 1.06064 | 1.40833 | 0.22613 | 0.94973 |
| L-glucose | 0.07667 | 1.15091 | −1.48167 | 0.24537 | 0.94661 |

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method comprising:

illuminating a first location of a chiral plasmonic substrate with electromagnetic radiation;

wherein the electromagnetic radiation comprises a wavelength that overlaps with at least a portion of the plasmon resonance energy of the chiral plasmonic substrate such that the chiral plasmonic substrate converts at least a portion of the electromagnetic radiation into thermal energy; and wherein the chiral plasmonic substrate is in thermal contact with a liquid sample comprising a plurality of chiral analytes;

thereby:

generating a bubble at a location in the liquid sample proximate to the first location of the chiral plasmonic substrate via plasmon-enhanced photothermal effects, the bubble having a gas-liquid interface with the liquid sample and a gas-solid interface with the chiral plasmonic substrate;

trapping at least a portion of the plurality of chiral analytes at the gas-liquid interface of the bubble and the liquid sample, said portion of the plurality of chiral analytes trapped at the gas-liquid interface being a trapped portion of the plurality of chiral analytes; and depositing at least a portion of the trapped portion of the plurality of chiral analytes on the chiral plasmonic substrate proximate to the gas-solid interface of the bubble and the chiral plasmonic substrate, said portion of the trapped portion of the plurality of chiral analytes deposited on the chiral plasmonic substrate being a deposited portion of the plurality of chiral analytes; and illuminating at least a portion of the deposited portion of the plurality of chiral analytes and at least the portion of the chiral plasmonic substrate at which the deposited portion of the plurality of chiral analytes is located with circularly polarized electromagnetic radiation, said portion of the deposited portion of the plurality of chiral analytes illuminated with the circularly polarized electromagnetic radiation being an illuminated portion of the deposited portion of the plurality of chiral analytes and said portion of the chiral plasmonic substrate at which the deposited portion of the plurality of chiral analytes is located illuminated with the circularly polarized electromagnetic radiation being an illuminated portion of the chiral plasmonic substrate;

capturing an electromagnetic signal from: the illuminated portion of the deposited portion of the plurality of chiral analytes, the illuminated portion of the chiral plasmonic substrate, or a combination thereof, wherein the circularly polarized electromagnetic radiation passes through both the illuminated portion of the deposited portion of the plurality of chiral analytes and the illuminated portion of the chiral plasmonic substrate before being captured; and processing the electromagnetic signal to determine a property of the liquid sample.

2. The method of claim 1, wherein the chiral plasmonic substrate comprises:

a first nanostructured layer comprising a first layer of a first plasmonic material permeated by a first plurality of spaced-apart holes, each hole being defined by an edge, wherein the first plurality of spaced apart holes comprise a first array defined by a first unit cell, the first unit cell having:

a first principle axis and a second principle axis with a first included angle between the first principle axis and the second principle axis;

wherein the first principle axis has a first length, the first length being measured from nearest edge to nearest edge between adjacent holes in the first array along the first principle axis;

wherein the second principle axis has a second length, the second length being measured from nearest edge to nearest edge between adjacent holes in the first array along the second principle axis;

a second nanostructured layer comprising a second layer of a second plasmonic material permeated by a second plurality of spaced-apart holes, each hole being defined by an edge, wherein the second plurality of spaced apart holes comprise a second array defined by a second unit cell, the second unit cell having:

a third principle axis and a fourth principle axis with a second included angle between the third principle axis and the fourth principle axis;

wherein the third principle axis has a third length, the third length being measured from the nearest edge to the nearest edge between adjacent holes the second array along the third principle axis;

wherein the fourth principle axis has a fourth length, the fourth length being measured from the nearest edge to the nearest edge between adjacent holes in the second array along the fourth principle axis;

wherein the first principle axis of the first array is rotated at a rotation angle compared to the third principle axis of the second array;

wherein the first nanostructured layer is achiral;

wherein the second nanostructured layer is achiral;

wherein the nanostructured plasmonic material is a moiré chiral metamaterial; and wherein:

the second nanostructured layer is disposed on the first nanostructured layer; or the nanostructured plasmonic material further comprises a third layer located between the first nanostructured layer and the second nanostructured layer and in contact with the first nanostructured layer and the second nanostructured layer.

3. The method of claim 1, wherein the liquid sample further comprises a solvent.

4. The method of claim 1, wherein the liquid sample comprises a bodily fluid.

5. The method of claim 4, wherein the bodily fluid comprises urine, plasma, blood, or a combination thereof.

6. The method of claim 1, wherein the plurality of chiral analytes comprise a biomolecule, a macromolecule, a pathogen, a drug, a biomarker, a metabolite, or a combination thereof.

7. The method of claim 1, wherein the plurality of chiral analytes comprise glucose, lactate, or a combination thereof.

8. The method of claim 1, wherein the plurality of chiral analytes have a concentration of from 1 picomolar (pM) to 100 millimolar (mM) in the liquid sample.

9. The method of claim 1, wherein liquid sample has a volume of 1 milliliter (mL) or less.

10. The method of claim 1, wherein the method further comprises depositing the liquid sample on the chiral plasmonic substrate.

11. The method of claim 10, wherein the method further comprises collecting the liquid sample.

12. The method of claim 1, wherein the trapped portion of the plurality of chiral analytes are not damaged during the trapping, wherein the deposited portion of the plurality of chiral analytes are not damaged during the deposition, or a combination thereof.

13. The method of claim 1, further comprising removing the illumination from the first location and allowing the bubble to collapse before illuminating with the circularly polarized light.

14. The method of claim 1, wherein the property of the liquid sample comprises the chirality of the illuminated portion of the deposited portion of the plurality of chiral analytes, the presence of the plurality of chiral analytes, the circular dichroism of the liquid sample, the concentration of the plurality of chiral analytes in the liquid sample, or a combination thereof.

15. The method of claim 1, further comprising diagnosing and/or monitoring a disease in a subject based on the property of the liquid sample.

16. The method of claim 15, further comprising selecting a course of therapy for the subject based on the property of the liquid sample.

17. The method of claim 1, wherein the time elapsed from illuminating the first location of the chiral plasmonic substrate to determining the property of the liquid sample is 10 minutes or less.

18. The method of claim 1, further comprising illuminating a second location of the chiral plasmonic substrate thereby:

generating a second bubble at a location in the liquid sample proximate to the second location of the chiral plasmonic substrate, the second bubble having a gas-liquid interface with the liquid sample and a gas-solid interface with the chiral plasmonic substrate;

trapping at least a second portion of the plurality of chiral analytes at the gas-liquid interface of the second bubble and the liquid sample, said second portion of the plurality of chiral analytes trapped at the gas-liquid interface being a second trapped portion of the plurality of chiral analytes; and depositing at least a portion of the second trapped portion of the plurality of chiral analytes on the chiral plasmonic substrate proximate to the gas-solid interface of the second bubble and the chiral plasmonic substrate, said portion of the second trapped portion of the plurality of chiral analytes deposited on the chiral plasmonic substrate being a second deposited portion of the plurality of chiral analytes.

19. The method of claim 18, wherein the first location and the second location are different and the method further comprises:

illuminating at least a portion of the second deposited portion of the plurality of chiral analytes and at least the portion of the chiral plasmonic substrate at which the second deposited portion of the plurality of chiral analytes is located with circularly polarized electromagnetic radiation, said portion of the second deposited portion of the plurality of chiral analytes illuminated with the circularly polarized electromagnetic radiation being an illuminated portion of the second deposited portion of the plurality of chiral analytes and said portion of the chiral plasmonic substrate at which the second deposited portion of the plurality of chiral analytes is located illuminated with the circularly polarized electromagnetic radiation being a second illuminated portion of the chiral plasmonic substrate;

capturing an electromagnetic signal from: the illuminated portion of the second deposited portion of the plurality of chiral analytes, the second illuminated portion of the chiral plasmonic substrate, or a combination thereof, wherein the circularly polarized electromagnetic radiation passes through both the illuminated portion of the second deposited portion of the plurality of chiral analytes and the second illuminated portion of the chiral plasmonic substrate before being captured; and processing the electromagnetic signal to determine a second property of the liquid sample.

20. The method of claim 18, wherein the first location and the second location are substantially the same.

21. A system comprising:

a chiral plasmonic substrate;

a liquid sample comprising a plurality of chiral analytes, the liquid sample being in thermal contact with the chiral plasmonic substrate;

a first light source configured to illuminate a first location of the chiral plasmonic substrate with electromagnetic radiation;

wherein electromagnetic radiation comprises a wavelength that overlaps with at least a portion of the plasmon resonance energy of the chiral plasmonic substrate such that the chiral plasmonic substrate converts at least a portion of the electromagnetic radiation into thermal energy;

thereby:

generating a bubble at a location in the liquid sample proximate to the first location of the chiral plasmonic substrate via plasmon-enhanced photothermal effects, the bubble having a gas-liquid interface with the liquid sample and a gas-solid interface with the chiral plasmonic substrate;

trapping at least a portion of the plurality of chiral analytes at the gas-liquid interface of the bubble and the liquid sample, said portion of the plurality of chiral analytes trapped at the gas-liquid interface being a trapped portion of the plurality of chiral analytes; and depositing at least a portion of the trapped portion of the plurality of chiral analytes on the chiral plasmonic substrate proximate to the gas-solid interface of the bubble and the chiral plasmonic substrate, said portion of the trapped portion of the plurality of chiral analytes deposited on the chiral plasmonic substrate being a deposited portion of the plurality of chiral analytes; and a second light source configured to illuminate at least a portion of the deposited portion of the plurality of chiral analytes and at least the portion of the chiral plasmonic substrate at which the deposited portion of the plurality of chiral analytes is located with circularly polarized electromagnetic radiation, said portion of the deposited portion of the plurality of chiral analytes illuminated with the circularly polarized electromagnetic radiation being an illuminated portion of the deposited portion of the plurality of chiral analytes and said portion of the chiral plasmonic substrate at which the deposited portion of the plurality of chiral analytes is located illuminated with the circularly polarized electromagnetic radiation being an illuminated portion of the chiral plasmonic substrate;

an instrument configured to capture an electromagnetic signal from: the illuminated portion of the deposited portion of the plurality of chiral analytes, the illuminated portion of the chiral plasmonic substrate, or a combination thereof, wherein the circularly polarized electromagnetic radiation passes through both the illuminated portion of the deposited portion of the plurality of chiral analytes and the illuminated portion of the chiral plasmonic substrate before being captured; and the instrument being further configured to process the electromagnetic signal to determine a property of the liquid sample.

* * * * *